US008834891B2

(12) United States Patent
Kroll et al.

(10) Patent No.: US 8,834,891 B2
(45) Date of Patent: Sep. 16, 2014

(54) **IMMUNOGENIC COMPOSITIONS COMPRISING *LAWSONIA INTRACELLULARIS***

(75) Inventors: Jeremy Kroll, Urbandale, IA (US); Mike Roof, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 275 days.

(21) Appl. No.: 11/374,350

(22) Filed: Mar. 13, 2006

(65) Prior Publication Data

US 2006/0204522 A1 Sep. 14, 2006

Related U.S. Application Data

(60) Provisional application No. 60/661,352, filed on Mar. 14, 2005.

(51) Int. Cl.
| | | |
|---|---|---|
| A61K 39/116 | (2006.01) | |
| A61K 39/00 | (2006.01) | |
| A61K 45/00 | (2006.01) | |
| A61K 39/112 | (2006.01) | |
| A01N 63/00 | (2006.01) | |
| A01N 65/00 | (2009.01) | |
| A61K 39/02 | (2006.01) | |

(52) U.S. Cl.
CPC ............ *A61K 39/105* (2013.01); *Y10S 424/825* (2013.01)
USPC .................. 424/203.1; 424/184.1; 424/278.1; 424/258.1; 424/282.1; 424/93.4; 424/93.1; 424/825

(58) Field of Classification Search
USPC ................................ 424/203.1, 278.1, 184.1
See application file for complete search history.

(56) References Cited

U.S. PATENT DOCUMENTS

| | | |
|---|---|---|
| 3,479,430 A | 11/1969 | Welter |
| 3,907,987 A | 9/1975 | Wilson |
| 4,132,597 A | 1/1979 | Kvanta |
| 4,237,218 A | 12/1980 | Monthony et al. |
| 4,880,739 A | 11/1989 | Yamada et al. |
| 4,904,597 A | 2/1990 | Inoue et al. |
| 4,920,048 A | 4/1990 | Diderichsen |
| 5,126,265 A | 6/1992 | Cidaria et al. |
| 5,192,679 A | 3/1993 | Dawson et al. |
| 5,230,912 A | 7/1993 | Yajima et al. |
| 5,296,221 A | 3/1994 | Mitsuoka et al. |
| 5,318,908 A | 6/1994 | Seki et al. |
| 5,338,670 A | 8/1994 | Sekura et al. |
| 5,380,657 A | 1/1995 | Schaefer et al. |
| 5,436,001 A | 7/1995 | Kramer |
| 5,610,059 A | 3/1997 | Joens et al. |
| 5,714,375 A | 2/1998 | Knittel et al. |
| 5,885,823 A | 3/1999 | Knittel et al. |
| 6,414,036 B1 | 7/2002 | Ninkov |
| 6,605,696 B1 * | 8/2003 | Rosey ........................... 530/300 |
| 6,649,660 B2 | 11/2003 | Ninkov |
| 6,921,536 B2 | 7/2005 | Jacobs et al. |
| 6,982,314 B2 | 1/2006 | Rosey |
| 7,022,328 B1 | 4/2006 | Panaccio et al. |
| 7,052,697 B1 | 5/2006 | Hasse et al. |
| 7,312,065 B2 * | 12/2007 | Roof et al. ................. 435/252.1 |
| 7,550,270 B2 | 6/2009 | Kroll et al. |
| 7,758,870 B2 | 7/2010 | Roof et al. |
| 8,398,970 B2 | 3/2013 | Deitmer et al. |
| 2002/0103261 A1 | 8/2002 | Ninkov |
| 2003/0021802 A1 | 1/2003 | Rosey |
| 2003/0087421 A1 | 5/2003 | Gebhart et al. |
| 2003/0157120 A1 | 8/2003 | Panaccio et al. |
| 2005/0031647 A1 * | 2/2005 | Roof et al. ................. 424/234.1 |
| 2005/0069559 A1 | 3/2005 | Jacobs et al. |
| 2005/0143561 A1 * | 6/2005 | Rosey ........................... 530/350 |
| 2006/0024696 A1 | 2/2006 | Kapur et al. |
| 2006/0171960 A1 * | 8/2006 | Chu et al. ................... 424/202.1 |
| 2006/0204522 A1 | 9/2006 | Kroll et al. |
| 2006/0286118 A1 | 12/2006 | Vermeij |
| 2007/0014815 A1 | 1/2007 | Kroll et al. |
| 2007/0212373 A1 | 9/2007 | Vermeij |
| 2008/0063648 A1 | 3/2008 | Kroll |
| 2008/0112980 A1 * | 5/2008 | Roof et al. ................. 424/234.1 |
| 2008/0226669 A1 | 9/2008 | Roof et al. |

(Continued)

FOREIGN PATENT DOCUMENTS

| | | |
|---|---|---|
| EP | 1094070 A2 | 4/2001 |
| EP | 1219711 A2 | 7/2002 |

(Continued)

OTHER PUBLICATIONS

Kroll et al. (AJVR, 2004; 65(4): 559-65).*

(Continued)

*Primary Examiner* — Gary Nickol
*Assistant Examiner* — Lakia Tongue
(74) *Attorney, Agent, or Firm* — Michael P. Morris; Joyce L. Morrison

(57) ABSTRACT

The present invention provides combination vaccines that comprise an immunological agent effective for reducing the incidence of or lessening the severity of PPE caused by *L. intracellularis*, and one or more immunological active components effective in treatment and/or prophylaxis of at least one further disease-causing organism for swine. Moreover, the present invention also relates to a kit that comprises an immunological agent effective for reducing the incidence of or lessening the severity of PPE caused by *L. intracellularis*, and one or more immunological active components effective in treatment and/or prophylaxis of at least one further disease-causing organism for swine.

21 Claims, No Drawings

(56) References Cited

U.S. PATENT DOCUMENTS

| | | |
|---|---|---|
| 2008/0241190 A1 | 10/2008 | Kroll et al. |
| 2008/0279893 A1 | 11/2008 | Vaughn et al. |
| 2009/0215698 A1 | 8/2009 | Schaeffer et al. |
| 2010/0062021 A1 | 3/2010 | Winkelman |
| 2010/0266637 A1 | 10/2010 | Deitmer et al. |

FOREIGN PATENT DOCUMENTS

| | | |
|---|---|---|
| EP | 1403643 A1 | 3/2004 |
| EP | 1586646 A2 | 10/2005 |
| WO | 9407531 A1 | 4/1994 |
| WO | 9639629 A1 | 12/1996 |
| WO | 9720050 A1 | 6/1997 |
| WO | 0069903 A1 | 11/2000 |
| WO | 0069904 A1 | 11/2000 |
| WO | 0069905 A1 | 11/2000 |
| WO | 0069906 A1 | 11/2000 |
| WO | 0189559 A2 | 11/2001 |
| WO | 0226250 A2 | 4/2002 |
| WO | 0238594 A1 | 5/2002 |
| WO | 03003335 A1 | 1/2003 |
| WO | 03006665 A1 | 1/2003 |
| WO | 2004033631 A2 | 4/2004 |
| WO | 2005011731 A1 | 2/2005 |
| WO | 2005026200 A2 | 3/2005 |
| WO | 2005070958 A2 | 8/2005 |
| WO | 2006020730 A2 | 2/2006 |
| WO | 2006099561 A1 | 9/2006 |
| WO | 2006113782 A2 | 10/2006 |
| WO | 2006116763 A2 | 11/2006 |
| WO | 2007011993 A1 | 1/2007 |
| WO | 2007140244 A2 | 12/2007 |
| WO | 2008063959 A1 | 5/2008 |
| WO | 2009037262 A2 | 3/2009 |

OTHER PUBLICATIONS

Marsteller et al., "Monitoring the prevalence of Lawsonia intracellularis IgG antibodies using serial sampling in growing and breeding swine herds". Journal of Swine Health and Production, Bol. 11, No. 3, 2003, pp. 127-130.

Mauch et al., "Effect of sow parity on the transmission of Lawsonia intracellularis to piglets". Veterinary Record, vol. 155, 2004, p. 532.

Stege et al., "Infection dynamics of Lawsonia intracellularis in pig herds". Veterinary Microbiology, vol. 104, 2004, pp. 197-206.

"Multicomponent Vaccine Development". NIH Guide, Vol. 22, No. 28, Aug. 1993, Retrieved from URL: http://grants.nih.gov/grants/guide/rfa-files/RFA-AI-93-017.html, Retrieved on Nov. 20, 2006, 9 pages.

"Vaccination Guidelines for Swine". Vido Swine Technical Group, Jun. 2004, (obtained on Jan. 6, 2009 from http://www.vido.org/pdf/vstg_pubs/Vaccination%20Guidelines_SWINE_.june18.2004-t11.pdf).

Alderton et al., "Experimental Reproduction of Porcine Proliferative Enteritis". Journal of Comparative Pathology, vol. 106, 1992, pp. 159-167.

Armbruster et al., "Evaluation of Enterisol® LI Ileitis Vaccine and Tylan® Premix Efficacy Against Porcine Proliferative Enteropathy in a Challenge Model". Proceedings of the 18th International Pig Veterinary Society Congress, vol. 2, Hamburg, Germany, 2004, p. 579.

Barna et al., "Effect of gilt seropositivity to Lawsonia intracellularis (LI) on their offspring's seropositivity to LI and on diarrhoea after a pure-culture challenge". Preventive Veterinary Medicine, vol. 61, No. 1, Sep. 2003, pp. 71-78.

Birch et al., "Suspension Culture of Mammalian Cells". Large-Scale Mammalian Cell Culture, Marcel Dekker, Inc., New York and Basel, 1990, pp. 258-270.

Boesen et al., "Development, characterization and diagnostic application of a monoclonal antibody specific for a proteinase K resistant Lawsonia intracellularis antigen". Veterinary Microbiology, vol. 105, 2006, pp. 199-206.

Boesen et al., "Evaluation of a novel enzyme-linked immunosorbent assay for serological diagnosis of porcine proliferative enteropathy". Veterinary Microbiology, vol. 109, 2005, pp. 105-112.

Boosinger et al., "Campylobacter sputorum subsp mucosalis and Campylobacter hyointestinalis infections in the intestine of gnotobiotic pigs". American Journal of Veterinary Research, vol. 46, No. 10, Oct. 1985, pp. 2152-2156.

Bornhorn, R., "Efficacy and economical impact of oral vaccination of partially infected piglets with Enterisol® Ileitis". Praktischer Tierarzt, vol. 88, No. 3, 2007, p. 172.

Bouma et al., "The influence of maternal immunity on the development of the in vitro lymphocyte proliferation response against pseudorabies virus in pigs". Research in Veterinary Science, vol. 64, 1998, pp. 167-171.

Brock et. al., "Immunization for Infectious Disease". Biology of Microorganisms, Ch. 16, PrenticeHall, Inc., 4th Ed., (19), 1984, pp. 557-558.

Chang et al., "Campylobacter hyointestinalis, a possible cause of proliferative enteritis in swine". Campylobacter II. Proceedings of the Second International Workshop on Campylobacter Infections, Brussels, Sep. 6-9, 1983, p. 131.

Chang et al., "Immunofluorescent demonstration of Campylobacter hyointestinalis and Campylobacter sputorum subsp mucosalis in swine intestines with lesions of proliferative enteritis". American Journal of Veterinary Research, vol. 45, No. 4, Apr. 1984, pp. 703-710.

Desrosiers, R., "Experiences with the Use of Enterisol® Ileitis in Canadian Breeding Animals". Ileitis Symposium, Hamburg, Germany, Jun. 28, 2004, (obtained on Jan. 6, 2009 from http://www.animal-health-online.de/drms/Vortrag_Desrosiers.pdf) pp. 1-4.

Fattom et al., "Epitopic overload at the site of injection may result in suppression of the immune response to combined capsular polysaccharide conjugate vaccines". Vaccine, vol. 17, 1999, pp. 126-133.

Finn, D.L., "Isolation and characterization of viral agents associated with porcine proliferative enteritis". A Thesis Submitted to the faculty of the Department of Microbiology and Immunology in Partial Fulfillment of the Requirements for the Degree of Master of Science with a Major in Microbiology, The University of Arizona, 1987, pp. 1-86.

Finter et al., "Large-Scale Mammalian Cell Culture: A Perspective". Large-Scale Mammalian Cell Culture, Marcel Dekker, Inc., New York and Basel, 1990, pp. 1-14.

Fox et al., "Campylobacter-like Omega Intracellular Antigen in Proliferative Colitis of Ferrets". Laboratory Animal Science, vol. 38, No. 1, Feb. 1988, pp. 34-36.

Frey et al., "Coiled bodies contain U7 small nuclear RNA and associate with specific DNA sequences in interphase human cells". Proceedings of the National Academy of Sciences of the United States of America, vol. 92, No. 13, Jun. 1995, pp. 5915-5919.

Gebhart et al., "Cloned DNA Probes Specific for the Intracellular Campylobacter-Like Organism of Porcine Proliferative Enteritis". Journal of Clinical Microbiology, vol. 29, No. 5, May 1991, pp. 1011-1015.

Gebhart et al., "Ileal Symbiont Intracellularis, an Obligate Intracellular Bacterium of Porcine Intestines Showing a Relationship to Desulfovibrio Species". International Journal of Systematic Bacteriology, vol. 43, No. 3, Jul. 1993, pp. 533-538.

Gebhart et al., "Species-specific DNA probes for Campylobacter species isolated from pigs with proliferative enteritis". Veterinary Microbiology, vol. 24, 1990, pp. 367-379.

Griffiths, B., "Scaling-up of Animal Cell Cultures". Animal Cell Culture-A Practical Approach, Chapter 3, IRL Press Limited, Oxford, England, 1986, pp. 33-69.

Guedes et al., "Validation of an immunoperoxidase monolayer assay as a serologic test for porcine proliferative enteropathy". Journal of Veterinary Diagnostic Investigation, vol. 14, 2002, pp. 528-530.

Hancock et al., Modern Microbiological Methods, Bacterial Cell Surface Techniques, A Wiley-Interscience Publication, John Wiley & Sons, Chichester, 1988, pp. 90-91.

Harvey, Stewart C., "Drug Absorption, Action and Disposition". Remington's Pharmaceutical Sciences, 18th Edition, (Ed) Gennaro AR, Mack Publishing Company, Easton, Pennsylvania, 1990, pp. 697-702.

(56) References Cited

OTHER PUBLICATIONS

Holyoake et al., "Enzyme-linked immunosorbent assay for measuring ileal symbiont intracellularis-specific immunoglobulin G response in sera of pigs". Journal of Clinical Microbiology, vol. 32, No. 8, 1994, pp. 1980-1985.
Horin et al., "Polymorphisms in equine immune response genes and their associations with infections". Mammalian Genome, vol. 15, 2004, pp. 843-850.
International Search Report and Written Opinion for PCT/US2006/09618 mailed Jul. 21, 2006.
Jasni et al., "Reproduction of proliferative enteritis in hamsters with a pure culture of porcine ileal symbiont intracellularis". Veterinary Microbiology, vol. 41, 1994, pp. 1-9.
Jones et al., "Enhanced Detection of Intracellular Organism of Swine Proliferative Enteritis, Ileal Symbiont Intracellularis, in Feces by Polymerase Chain Reaction". Journal of Clinical Microbiology, vol. 31, No. 10, Oct. 1993, pp. 2611-2615.
Jones, Gary F., "The Diagnosis and Cause of Swine Proliferative Enteritis"., A Thesis Submitted to the Faculty of the Graduate School of the University of Minnesota, Minneapolis, MN, Jun. 1993, pp. 1-190.
Kesl et al., "Tylan® Premix and Enterisole® LI Ileitis vaccine evaluations in a Lawsonia intracellularis challenge model". American Swine Association of Swine Veterinarians, 2004, pp. 139-142.
Knittel et al., "Evaluation of antemortem polymerase chain reaction and serologic methods for detection of Lawsonia intracellularis-exposed pigs". American Journal of Veterinary Research, vol. 59, No. 6, Jun. 1998, pp. 722-723, 725.
Koyama et al., "In Vitro Cultivation and Partial Characterization of Lawsonia Intracellularis from a Japanese Field Case of Porcine Proliferative Enteropathy". Proceedings of the 18th IPVS Congress, vol. 1, Hamburg, Germany, 2004, p. 307.
Kroll et al., "Efficacy of an Avirulent Lawsonia intracellularis Vaccine in Swine". Abstracts of the General Meeting of the American Society for Microbiology, vol. 101, Session No. 236/Z, Abstract Z-40, American Society for Microbiology 101st General Meeting, Orlando, FL, May 23, 2001, p. 747.
Kroll et al., "Lipopolysaccharide-Based Enzyme-Linked Immunosorbent Assay for Experimental Use in Detection of Antibodies to Lawsonia intracellularis in Pigs". Clinical and Diagnostic Laboratory Immunology, vol. 12, No. 6, Jun. 2005, pp. 693-699.
Kroll et al., "Maternal Immunity Associated with Lawsonia Intracellularis Exposure and Vaccination". Proceedings of the 18th IPVS Congress, Hamburg, Germany, vol. I, 2004, p. 255.
Kuan et al., "Production of Monoclonal Antibody That Recognizes the Lipopolysaccharide of a Campylobacter-Like Organism". Microbiology and Immunology, vol. 36, No. 8, 1992, pp. 791-801.
Lavoie et al., "Equine proliferative enteropathy: a cause of weight loss, colic, diarrhoea and hypoproteinaemia in foals on three breeding farms in Canada". Equine Veterinary Journal, vol. 32, No. 5, Sept. 200, pp. 418-425, Abstract Only, 2000.
Lawson et al., "Attempts to Cultivate the Campylobacter-like Organism of the Proliferative Enteropathies". Association of Vet. Teachers and Research Workers, Apr. 1990, Abstract C50.
Lawson et al., "Infection of cultured rat enterocytes by Ileal symbiont intracellularis depends on host cell function and actin polymerisation". Veterinary Microbiology, vol. 45, 1995, pp. 339-350.
Lawson et al., "Intestinal Adenomatosis in the Pig: A Bacteriological Study"., Research Journal of Veterinary Sciences, vol. 37, 1974, pp. 331-336.
Lawson et al., "Intracellular Bacteria of Porcine Proliferative Enteropathy: Cultivation and Maintenance in Vitro". Journal of Clinical Microbiology, vol. 31, No. 5, May 1993, pp. 1136-1142.
Lawson et al., "Proliferative Haemorrhagic enteropathy". Research in Veterinary Science, vol. 27, 1979, pp. 46-51.
Lawson et al., "Review: Proliferative Enteropathy". Journal of Comparative Pathology, vol. 122, 2000, pp. 77-100.
Lomax et al., "Experimentally induced porcine proliferative enteritis in specific-pathogen-free pigs". American Journal of Veterinary Research, vol. 43, No. 9, Sep. 1982, pp. 1615-1621.
Lomax, L.G., "Porcine proliferative enteritis-characterization of the naturally occurring and experimental disease". A Dissertation Submitted to the Graduate Faculty in Partial Fulfillment of the Requirements for the Degree of Doctor of Philosophy. Iowa State Univeristy, Ames, Iowa, 1981, pp. 1-206.
Love et al., "Pathology of Proliferative Haemorrhagic Enteropathy in Pigs". Veterinary Pathology, vol. 16, 1979, pp. 41-48.
Wattanaphansak et al., "In vitro antimicrobial activity against 10 North American and European Lawsonia intracellularis isolates". Veterinary Microbiology, vol. 134, 2009, pp. 305-310.
Knittel et al., "Efficacy of an Avirulent Lawsonia Intracellularis Vaccine in Swine". The 16th International Pig Veterinary Society Congress, Melbourne, Australia, Sep. 17-20, 2000, p. 24.
Joens et al., "Induction of gross and microscopic lesions of porcine proliferative enteritis by Lawsonia intracellaris". American Journal of Veterinary Research, vol. 58, No. 10, 1997, pp. 1125-1131.
Chouet et al., "Patterns of exposure to Lawsonia intracellularis infection on European pig farms". Veterinary Record, vol. 152, 2003, pp. 14-17.
Knittel et al., "United States isolates of Lawsonia intracellularis from porcine proliferative enteropathy resemble European isolates". Sine Health and Production, vol. 4, No. 3, 1996, pp. 119-122.
Biksi et al., "Detection of Lawsonia intracellularis in Hungarian swine herds by polymerase chain reaction". Acta Veterinaria Hungarica, vol. 46, No. 4, pp. 415-420, 1998.
Mcorist et al., "Monitored control programme for proliferative enteropathy on British pig farms". Veterinary Records, vol. 144, No. 8, 1999, pp. 202-204.
Tomanová et al., "Lawsonia intracellularis in Wild Mammals in the Slovak Carpathians". Journal of Wildlife Diseases, vol. 39, No. 2, Apr. 2003, pp. 407-411.
McCluskey et al., "LsaA, an Antigen Involved in Cell Attachment and Invasion, Is Expressed by Lawsonia intracellularis during Infection In Vitro and In Vivo". Infection and Immunity, vol. 70, No. 6, Jun. 2002, pp. 2899-2907.
Mcorist et al., "Antimicrobial Susceptibility of Ileal Symbiont Intracellularis Isolated from Pigs with Proliferative Enteropathy". Journal of Clinical Microbiology, vol. 33, No. 5, May 1995, pp. 1314-1317.
Mcorist et al., "Characterization of Lawsonia intracellularis gen. nov., sp. nov., the Obligately Intracellular Bacterium of Porcine Proliferative Enteropathy". International Journal of Systematic Bacteriology, vol. 45, No. 4, Oct. 1995, pp. 820-825.
Mcorist et al., "Control of porcine proliferative enteropathy by oral administration of chlortetracycline". The Veterinary Record, vol. 144, Jan. 1999, pp. 48-49.
Mcorist et al., "Early Lesions of Proliferative Enteritis in Pigs and Hamsters". Veterinary Pathology, vol. 26, No. 3, May 1989, pp. 260-264.
Mcorist et al., "Entry of the bacterium ileal symbiont intracellularis into cultured enterocytes and its subsequent release". Research in Veterinary Science, vol. 59, 1995, pp. 255-260.
Mcorist et al., "In Vitro and In-Life Studies of Efficacy of Valnemulin for Proliferative Enteropathy (ILEITIS)". Proceedings of the 15th IPVS Congress, Birmingham, England, Jul. 1998, p. 114.
Mcorist et al., "In vitro testing of antimicrobial agents for proliferative enteropathy (ILEITIS)". Swine Health and Production, vol. 3, No. 4, Jul and Aug. 1995, pp. 146-149.
Mcorist et al., "Monoclonal antibodies to intracellular campylobacter-like organisms of the porcine proliferative enteropathies". The Veterinary Record, vol. 121, No. 18, Oct. 1987, pp. 421-422.
Mcorist et al., "Oral administration of tylosin phosphate for treatment and prevention of proliferative enteropathy in pigs". Advanced Journal of Veterinary Research, vol. 58, No. 2, Feb. 1997, pp. 136-139.
Mcorist et al., "Polymerase chain reaction for diagnosis of porcine proliferative enteropathy". Veterinary Microbiology, vol. 41, No. 3, 1994, pp. 205-212.
Mcorist et al., "Porcine Proliferative Enteropathy". The Veterinary Record, vol. 132, No. 14, Apr. 1993, p. 368.
Mcorist et al., "Reproduction of Porcine Proliferative Enteropathy with Pure Cultures of Ileal Symbiont Intracellularis". Infection and Immunity, vol. 61, No. 10, Oct. 1993, pp. 4286-4292.

(56) References Cited

OTHER PUBLICATIONS

Mcorist et al., "Synergism of ileal symbiont intracellularis and gut bacteria in the reproduction of porcine proliferative enteropathy". The Veterinary Record, vol. 134, No. 13, Mar. 1994, pp. 331-332.
Mcorist et al., "The Treatment of Induced Porcine Proliferative Enteropathy (ILEITIS) with Tylosin Tartrate (Tylan® Soluble, Elanco) Administered Via Drinking Water". Proceedings of the 15th IPVS Congress, Birmingham, England, Jul. 1998, p. 118.
Mcorist et al., "Treatment and prevention of porcine proliferative enteropathy with oral tiamulin". The Veterinary Record, vol. 139, Dec. 1996, pp. 615-618.
Nelson, J.B., "The Maternal Transmission of vaccinial Immunity in Swine". The Journal of Experimental Medicine, vol. 56, 1932, pp. 835-840.
Nelson, J.B., "The Maternal Transmission of Vaccinial Immunity in Swine". The Journal of Experimental Medicine, vol. 60, 1934, pp. 287-291.
Nielsen et al., ":The serological response to Salmonella serovars typhimurium and infantis in experimentally infected pigs. The time course followed with an indirect anti-LPS ELISA and bacteriological examinations". Veterinary Microbiology, vol. 47, 1995, pp. 205-218.
Oka et al., "Large-Scale Animal Cell Culture: A Biological Perspective". Large-Scale Mammalian Cell Culture, Marcel Dekker, Inc., New York and Basel, 1990, pp. 71-73.
Peace et al., "Comparative Analysis of the 16S rRNA Gene Sequence of the Putative Agent of Proliferative Ileitis of Hamsters". International Journal of Systematic Bacteriology, vol. 44, No. 4, Oct. 1994, pp. 832-835.
Pensaert et al., "Viremia and effect of fetal infection with porcine viruses with special reference to porcine circovirus 2 infection". Veterinary Microbiology, vol. 98, 2004, pp. 175-183.
Pozo et al., "Study of Lawsonia Intracellularis Infection in Breeding Stock and Suckling Pigs". Proceedings of the 17th IPVS Congress, Ames, Iowa, 2002, vol. 2, p. 205.
Product Insert for Enterisol Ileitis®, Boehringer Ingelheim Vetmedica, Inc., Jan. 2005, 2 pages.
Product Insert for Enterisol® SC-54, Boehringer Ingelheim Vetmedica, Inc., May 2003, 2 pages.
Reuveny, S., "Microcarrier Culture Systems". Bioprocess Technology, vol. 10, 1990, pp. 271-341.
Reuveny, S., "Microcarriers in Cell Culture Structure and Applications". Advances in Cell Culture, vol. 4, 1985, pp. 213-247.
Rowland et al., "Intestinal Adenomatosis in the Pig: Occurrence of a Bacterium in Affected Cells". Nature, vol. 243, Jun. 1973, p. 417.
Rowland et al., Porcine intestinal adenomatosis: A possible relationship with necrotic enteritis, regional ileitis and proliferative haemorrhagic enteropathy. Veterinary Records, vol. 97, 1975, pp. 178-180.
Schoeb et al., "Enterococcolitis Associated with Intraepithelial Campylobacter-like Bacteria in Rabbits (Oryctolagus cuniculus)". Veterinary Pathology, vol. 27, 1990, pp. 73-80.
Schultheiss, P.C., "A Study of the Pathogenicity of Campylobacter Species in Swine". A Thesis Submitted to the Faculty of the Graduate School of the University of Minnesota, Jun. 1987, pp. 1-287.
Senk et al., "Proliferative typhlocolitis—the fifth form of the porcine intestinal adenomatosis complex". Proceedings, International Pig Veterinary Society, 11th Congress, Jul. 1-5, 1990, Lausanne, Switzerlandk, 1990, p. 113.
Spier et al., "Trypsinization of BHK 21 Monolayer Cells Grown in Two Large-Scale Unit Process Systems". Biotechnology and Bioengineering, vol. XIX, 1977, pp. 1735-1738.
Starek et al., "Sows Seropositive to Lawsonia intracellularis (LI) Influence Performance and Li Seropositivity of their Offspring". ACTA Veterinaria BRNO, vol. 73, No. 3, 2004, pp. 341-345.
Stills, H.F., "Isolation of an Intracellular Bacterium from Hamsters (Mesocricetus auratus) with Proliferative Ileitis and Reproduction of the Disease with a Pure Culture". Infection and Immunity, vol. 59, No. 9, Sep. 1991, pp. 3227-3236.
Tam et al., "Eukaryotic Cells Grown on Microcarrier Beads Offer a Cost-Efficient Way to Propagate Chlamydia trachomatis". BioTechniques, vol. 13, No. 3, 1992, pp. 374-378.
Thacker, E., "Vaccines How They Work, Why They Fail". National Hog Farmer, Apr. 15, 2003. Retrieved online Jun. 16, 2008, 6 pages. http://www.nationalhogfarmer.com/mag/farming_vaccines_work_why/index.html.
Tseneva et al., "Invasiveness and cytotoxicity as criteria in assessing Yersinia attenuation". Zhurnal Mikrobiologii, Epidemiologii, i Immunobiologii, vol. 10, No. 6, Sep. 1988, pp. 10-16, Abstract Only.
Walter et al., "Serologic profiling and vaccination timing for Lawsonia intracellularis". Journal of Swine Health and Production, vol. 12, No. 6, 2004, pp. 310-313.
Ward et al., "Diagnosing, treating, and controlling proliferative enteritis in swine". Veterinary Medicine, Food-Animal Practice, Mar. 1990, pp. 312-318.
Ward et al., "Reproduction of proliferative enteritis in pigs fed embryonated eggs inoculated with proliferative enteritis tissues". Proceedings, International Pig Veterinary Society, 11th Congress, Jul. 1-5, 1990, Lausanne, Switzerland, p. 116.
Wittmann et al., "Colostral Immunity in Piglets From Sows Vaccinated With Inactivated Aujeszky Disease Virus Vaccine". Archives of Virology, vol. 60, 1979, pp. 33-42.
Wiuff et al., "Immunochemical analyses of serum antibodies from pig herds in a Salmonella non-endemic region". Veterinary Microbiology, vol. 85, 2002, pp. 69-82.
Yates et al., "Proliferative Hemorrhagic Enteropathy in Swine: An Outbreak and Review of Literature". Canadian Veterinary Journal, vol. 20, Oct. 1979, pp. 261-268.

\* cited by examiner

IMMUNOGENIC COMPOSITIONS COMPRISING *LAWSONIA INTRACELLULARIS*

RELATED APPLICATION

This application claims benefit to U.S. Provisional Application Ser. No. 60/661,352 of Mar. 14, 2005, the disclosure of which is incorporated by reference in its entirety.

BACKGROUND

The present invention relates to combination vaccines or multivalent vaccines comprising *Lawsonia intracellularis* (*L. intracellularis*) antigen and at least one further antigen of one or more swine pathogens other than *L. intracellularis*. More particularly, the present invention provides immunogenic compositions effective at inducing an immune response against infection by *L. intracellularis* and at least one other disease-causing organism for swine.

*L. intracellularis*, the causative agent of porcine proliferative enteropathy ("PPE"), affects virtually all animals, including: rabbits, ferrets, hamsters, fox, horses, and other animals as diverse as ostriches and emus. PPE is a common diarrheal disease of growing-finishing and young breeding pigs characterized by hyperplasia and inflammation of the ileum and colon. It often is mild and self-limiting but sometimes causes persistent diarrhea, severe necrotic enteritis, or hemorrhagic enteritis with high mortality.

The bacteria associated with PPE have been referred to as "Campylobacter-like organisms." S. McOrist et al., Vet. Pathol., Vol. 26, 260-264 (1989). Subsequently, the causative bacteria have been identified as a novel taxonomic genus and species, vernacularly referred to as *Ileal symbiont* (IS) intracellularis. C. Gebhart et al., Int'l. J. of Systemic Bacteriology, Vol. 43, No. 3, 533-538 (1993). More recently, these novel bacteria have been given the taxonomic name *Lawsonia* (*L.*) *intracellularis*. S. McOrist et al., Int'l. J. of Systemic Bacteriology, Vol. 45, No. 4, 820-825 (1995). These three names have been used interchangeably to refer to the same organism as further identified and described herein. Koch's postulates have been fulfilled by inoculation of pure cultures of *L intracellularis* into conventionally reared pigs; typical lesions of the disease were produced, and *L intracellularis* was reisolated from the lesions. The more common, nonhemorrhagic form of the disease often affects 18- to 36-kg pigs and is characterized by sudden onset of diarrhea. The feces are watery to pasty, brownish, or faintly blood stained. After ~2 days, pigs may pass yellow fibrinonecrotic casts that have formed in the ileum. Most affected pigs recover spontaneously, but a significant number develop chronic necrotic enteritis with progressive emaciation. The hemorrhagic form is characterized by cutaneous pallor, weakness, and passage of hemorrhagic or black, tarry feces. Pregnant gilts may abort. Lesions may occur anywhere in the lower half of the small intestine, cecum, or colon but are most frequent and obvious in the ileum. The wall of the intestine is thickened, and the mesentery may be edematous. The mesenteric lymph nodes are enlarged. The intestinal mucosa appears thickened and rugose, may be covered with a brownish or yellow fibrinonecrotic membrane, and sometimes has petechial hemorrhages. Yellow necrotic casts may be found in the ileum or passing through the colon. Diffuse, complete mucosal necrosis in chronic cases causes the intestine to be rigid, resembling a garden hose. Proliferative mucosal lesions often are in the colon but are detected only by careful inspection at necropsy. In the profusely hemorrhagic form, there are red or black, tarry feces in the colon and clotted blood in the ileum. Altogether, *L. intracellularis* is a particularly great cause of losses in swine herds in Europe as well as in the United States.

*L. intracellularis* is an obligate, intracellular bacterium which cannot be cultured by normal bacteriological methods on conventional cell-free media and has been thought to require cells for growth. S. McOrist et al., Infection and Immunity, Vol. 61, No. 19, 4286-4292 (1993) and G. Lawson et al., J. of Clinical Microbiology, Vol. 31, No. 5, 1136-1142 (1993) discuss cultivation of *L. intracellularis* using IEC-18 rat intestinal epithelial cell monolayers in conventional tissue culture flasks. In U.S. Pat. Nos. 5,714,375 and 5,885,823, both of which patents are herein incorporated by reference in their entireties, cultivation of *L. intracellularis* in suspended host cells was described.

Pathogenic and non-pathogenic attenuated bacteria strains of *L. intracellularis* are well known in state of the art. For example, WO 96/39629 and WO 05/011731 describe non-pathogenic attenuated strains of *L. intracellularis*. Further attenuated bacteria strains of *L. intracellularis* are known from WO 02/26250 and WO 03/00665.

*Actinobacillus pleuropneumonia*, also known as APP and *Haemophilus pleuropneumonia*, is caused by the *Actinobacillus pleuopneumonia* bacteria. There are currently 15 serovars described and the severity of the clinical signs differ between the different serovirus and the presence of other factors. Serovirus 1, 5, 9, 10, and 11 are considered to be more virulent. Additionally, serovirus 1, 9, and 11; 2, 6, and 8; and 4 and 7 may cross-react. Pigs of all ages are susceptible. Clinical signs are a sudden illness that results in animals lying down a lot and presenting a high rectal temperature of 41.5° Celsius. Animals are generally anorexic and do not drink, their extremities become cyanotic and cold to the touch. Cyanosis can spread to the whole body and severe breathing difficulties, often with mouth breathing, develop before death. Blood-stained froth can be seen at the mouth and nostrils and death generally occurs within 24-48 hours. Acute clinical signs include a high percentage of animals in a group being depressed and lying down, high rectal temperatures of 40.5-41° Celsius, anorexia, lack of drinking, severe respiratory distress, coughing, mouth breathing, cyanosis, vomiting, and abortion. Sub-acute clinical signs include intermittent coughing in a group of pigs, a general loss of appetite, and a reduction in growth. Cyrovar type 3 presents with arthritis, endocarditis, and abscesses. In chronically effected herds, daily weight gain may not be effected, but an intermittent cough may be heard.

*Bordetella bronchiseptica* Infection: Asymptomatic pigs may harbor this gram-negative, nonsporeforming rod in the nasal cavity and trachea. Subclinical infections are more common in colonies, but epizootic outbreaks can occur rapidly with high morbidity and mortality. Transmission is by aerosol or, in its genital form, through sexual contact. Genital infection may cause infertility, stillbirths, and abortions. Several other species may be asymptomatic upper respiratory carriers, including dogs, cats, rabbits, rats, and mice. Contact with these potential hosts should be avoided. Necropsy may reveal lung consolidation and mucopurulent exudate in the bronchi, trachea, and middle ear.

Spirochaetal colitis is caused by the *Brachyspira pilosicoli* bacteria. This infection generally affects 10-20 week old growers/finishers. It is characterized by a non-fatal wasting diarrhea of growing pigs that results in an increased number of days needed to finish. The diarrhea also results in reduction in feed efficiency and produces watery diarrhea or loose stools. About half of the pigs may show transient to persistent, to watery to mucoid green to brownish diarrhea, without blood. The clinical signs are more common 10-14 days after mixing and changing of the feed. Swine dysentery is caused by the bacteria *Brachyspira hyodysenteriae*. There are twelve known sero-types at this time. Clinical signs in established herd include diarrhea, a rapid loss of condition in some pigs, a hairy appearance, dehydration, painful abdomen, and the death of one or two pigs before other pigs show any signs. In a key outbreak in naive herds, all age groups from suckling piglets to adult sows can be effected.

Brucellosis is caused by bacteria of the genus *Brucella* and is characterized by abortion, retained placenta, infertility, orchitis in boars and severe metritis in sows. In piglets, the disease is characterized by posterior paralysis and lameness. The disease in pigs is caused almost exclusively by *Brucella suis* biovars 1, 2, and 3. A number of other mammals can carry and transmit *Brucella suis* to pigs. Infection spreads rapidly and causes many abortions in unvaccinated herds. Transmission occurs mainly by contact with another pig, although venereal transmission is possible. Serological diagnosis can be difficult due to a relatively common organism, *Yersinia enterocolitica* O:9 which shares a common antigen with *Brucella* and often causes false positive results. Post-mortem lesions usually include metritis and orchitis, and can include abscessation, sometimes with necorsis foci in the liver.

Porcine Epidemic Diarrhea (PED) is caused by a coronavirus somewhat similar to that which causes TGE. This virus is widespread in Europe. The virus damages the villi in the gut thus reducing the absorptive surface, with attendant loss of fluid and dehydration. After introduction of the virus into a susceptible breeding herd, a strong immunity develops over two to three weeks. The colostral immunity then protects the piglets. The virus usually disappears spontaneously from breeding herds particularly small ones (<300 sows). Acute outbreaks of diarrhea occur when the virus is first introduced into a susceptible population. In such cases up to 100% of sows may be affected, showing a mild to very watery diarrhea. Two clinical pictures are recognized: PED Type I only affects growing pigs whereas PED Type II affects all ages including sucking pigs and mature sows. The incubation period is approximately 2 days and diarrhea lasts for 7 to 14 days. In sucking pigs the disease can be mild or severe with mortalities up to 40%. In large breeding herds, particularly if kept extensively, not all the females may become infected the first time around and there may be recrudescence. This only occurs in piglets suckling from sows with no maternal antibodies and is therefore sporadic.

*Clostridium* is a ubiquitous gram-positive bacteria, of the family clostridiaceae, usually found in the soil, but which also occurs naturally in the gut of most animals. *C. difficile* infections in swine are characterized by severe mesocolonic edema, diarrhea, and edema in other tissues such as the hydrothorax. Clostridium enteritis in swine is caused by *C. perfringens*, and is characterized by chronic enteritis, which is accompanied by diarrhea, weight loss and fever. Infection with *C perfringens* types A, B and C causes severe enteritis, dysentery, toxemia, and high mortality in young calves. Types B and C both produce the highly necrotizing and lethal β toxin that is responsible for the severe intestinal damage. This toxin is sensitive to proteolytic enzymes, and disease is associated with inhibition of proteolysis in the intestine. Sow colostrum, which contains a trypsin inhibitor, has been suggested as a factor in the susceptibility of young piglets. The disease can cause sudden death in piglets less than one week old, and is most common within 3 days of birth. In older piglets, Clostridium enteritis causes a thickening of the small intestine making absorption of food and nutrients difficult. Piglets usually die as a result of a combination of the infection and lack of nutrients. Death may occur in a few hours, but less severe cases survive for a few days, and recovery over a period of several days is possible. Hemorrhagic enteritis with ulceration of the mucosa is the major lesion in all species. Grossly, the affected portion of the intestine is deep blue-purple and appears at first glance to be an infarction associated with mesenteric torsion. Smears of intestinal contents can be examined for large numbers of gram-positive, rod-shaped bacteria, and filtrates made for detection of toxin and subsequent identification by neutralization with specific antiserum. *Clostridium novyi* has been suspected but not yet confirmed as a cause of sudden death in cattle and pigs fed high-level grain diets, and in which pre-existing lesions of the liver were not detectable. The lethal and necrotizing toxins (primarily a toxin) damage hepatic parenchyma, thereby permitting the bacteria to multiply and produce a lethal amount of toxin. Usually, death is sudden with no well-defined signs. Affected animals tend to lag behind the herd, assume sternal recumbency, and die within a few hours. Most cases occur in the summer and early fall when liver fluke infection is at its height. The disease is most prevalent in 1- to 4-yr-old sheep and is limited to animals infected with liver flukes. Differentiation from acute fascioliasis may be difficult, but peracute deaths of animals that show typical lesions on necropsy should arouse suspicion of infectious necrotic hepatitis. The most characteristic lesions are the grayish yellow necrotic foci in the liver that often follow the migratory tracks of the young flukes. Other common findings are an enlarged pericardial sac filled with straw-colored fluid, and excess fluid in the peritoneal and thoracic cavities. Usually, there is extensive rupture of the capillaries in the subcutaneous tissue, which causes the adjacent skin to turn black (hence the common name, black disease). *Clostridium septicum* is found in soil and intestinal contents of animals (including man) throughout the world. Infection ordinarily occurs through contamination of wounds containing devitalized tissue, soil, or some other tissue-debilitant. Wounds caused by accident, castration, docking, insanitary vaccination, and parturition may become infected. General signs, such as anorexia, intoxication, and high fever, as well as local lesions, develop within a few hours to a few days after predisposing injury. The local lesions are soft swellings that pit on pressure and extend rapidly because of the formation of large quantities of exudate that infiltrates the subcutaneous and intramuscular connective tissue of the affected areas. Accumulations of gas are uncommon. Malignant edema associated with lacerations is characterized by marked edema, severe toxemia, and death in 24-48 hr. Tetanus toxemia is caused by a specific neurotoxin produced by *Clostridium tetani* in necrotic tissue. Almost all mammals, including swine, are susceptible to this disease. Although tetanus is worldwide in distribution, there are some areas, such as the northern Rocky Mountain section of the USA, where the organism is rarely found in the soil and where tetanus is almost unknown. In general, the occurrence of *C tetani* in the soil and the incidence of tetanus in man is higher in the warmer parts of the various continents. *Clostridium tetani*, an anaerobe with terminal, spherical spores, is found in soil and intestinal tracts. In most cases, it is introduced into the tissues through wounds, particularly deep puncture wounds, that provide a suitable anaerobic environment.

*Escherichia coli* is a bacteria of the enterbacteriaceae family and is one of the main types of bacteria naturally occurring in the small intestines of all mammals. Although usually harmless, some *E coli* strains can produce a number of exo- and endotoxins that cause infection and disease. Heat-labile (LT) and heat-stable (ST) exotoxins are actively produced by some strains and are responsible for causing scour. Shigelalike toxin type II variant (SLT-IIe), Stx2e and verotoxin edema disease act on the wall of the small arteries resulting in oedema. Endotoxins, such as Lipid A, play a role in mastitis and urinary tract infections. *E. coli* infection is characterized by a number of different symptoms depending on the particular strain involved, including diarrhea, sunken eyes, unthriftiness, visible weight loss, stunted growth, depression, bowel edema, mastitis, cystitis, pyelonephritis and death. *E. coli* can be classified and coded by their cell wall (O antigens) and fimbriae (F antigens). For example, scour is often associated with *E. coli* Abbotstown: 0147, F4, F5, whereas bowel edema is associated with F18 fimbriae. Correctly identifying the code is essential to the selection of the correct vaccine. *E. coli* infections compromise a pig's immune system and deaths are often the result of secondary infections and disease.

*Encephalomyocarditis*, or EMC, infects and causes disease in a wide range of vertebrate animals but pigs appear to be the most susceptible of farm animal species. The virus, *Encephalomyocarditis* virus is world-wide but differs in pathogenicity and virulence in different countries and regions. In most countries of Europe, particularly those in the EU, it tends to be relatively mild or non-pathogenic and disease in pigs is rarely diagnosed. In Australia the strains appear to be much more virulent for pigs than those in New Zealand. Virulent strains in Florida, the Caribbean and probably Central America damage the heart and cause death whereas those in the Mid West of the US tend to cause reproductive problems. Clinical disease in pigs tends to occur when rat numbers increase to plague levels. Pigs can be infected from rats or from rat-contaminated feed or water. It does not seem to spread very readily between pigs. In affected herds there are usually no clinical signs in weaned and growing pigs.

*Eperythrozoonosis* is a Rickettsial (haemotrophic) disease caused by *Eperythrozoon suis*, an extracellular bacterial organism that adheres to pig erythrocyte membranes, inducing its deformation and damage. The disease is characterized by anemia and icterus (yellow discoloration of mucous membranes, sclera and inner ears). It can lead to poor conception rates, other vague reproduction problems and even death.

Swine erysipelas is caused by a bacterium, *Erysipelothrix rhusiopathiae* that is found in most if not all pig farms. Up to 50% of animals may carry it in their tonsils. It is always present in either the pig or in the environment because it is excreted via saliva, feces or urine. It is also found in many other species, including birds and sheep and can survive outside the pig for a few weeks and longer in light soils. Thus it is impossible to eliminate it from a herd. Infected feces are probably the main source of infection, particularly in growing and finishing pens. The bacterium alone can cause the disease but concurrent virus infections, such as PRRS or influenza, may trigger off outbreaks. Disease is relatively uncommon in pigs under 8-12 weeks of age due to protection provided by maternal antibodies from the sow via the colostrum. The most susceptible animals are growing pigs, non vaccinated gilts and up to 4th parity sows. The organism multiplies in the body, and invades the bloodstream to produce a septicaemia. The rapidity of multiplication and the level of immunity in the pig then determines the clinical symptoms.

Glassers Disease is caused by the bacterium *Haemophilus parasuis* (Hps), of which there are at least fifteen different types. It is found throughout the world and organisms are present even in high health herds. If such herds are set up using SPF or MEW techniques and are free from Hps it can be devastating when they first become contaminated, producing an anthrax-like disease with high mortality in sows. In the majority of herds in which the bacterium is endemic, sows produce a strong maternal immunity which normally persists in their offspring until 8 to 12 weeks of age. As a result, the effects of the infection in weaners are usually nil or minimal. Disease may however be seen in suckling pigs. Pigs usually become sub-clinically infected when still protected by maternal antibody and then stimulate their own immune response. If however, the maternal immunity wears off before they become infected they may develop severe disease. This is usually sometime after weaning. It can also act as a secondary pathogen to other major diseases particularly enzootic pneumonia (EP) (Mycoplasma hyopneumoniae). Outbreaks of disease are sometimes experienced in sucking pigs, particularly in gilt herds. Hps attacks the smooth surfaces of the joints, coverings of the intestine, lungs, heart and brain, causing pneumonia, heart sac infection, peritonitis and pleurisy. It is respiratory spread. Disease caused by Hps is rare in sows unless the dry sow is naive. Lameness or stiffness, slight swellings over the joints and tendons, and rarely meningitis, are occasionally seen in gilts. In piglets, acute disease presents with rapidly depressed pigs with elevated temperature, inappetence, and a reluctance to rise. One characteristic feature is a short cough of 2-3 episodes. Sudden death in good sucking piglets is not uncommon. Hps is also known to cause individual cases of arthritis and lameness with fever and inappetence. Chronic disease is characterized by pale and poor growing pigs. Sudden death may also occur. For weaners and growers, pigs with Glassers Disease become rapidly depressed or may be just found dead. Other symptoms include elevated temperature, anorexia, a reluctance to rise, nervous signs such as fits and convulsions including meningitis, and poor pigs, that are wasting and hairy often result. In young growing pigs, the following symptoms are most common: fever, mild meningitis, arthritis, lameness, pneumonia, heart sac infection, peritonitis and pleurisy. Again, a characteristic feature is a short cough of only 2-3 episodes.

Leptospirosis is a contagious disease of animals, including man, caused by various immunologically distinct leptospiral serovars, most of which are regarded as subgroups of *Leptospira interrogans*. There are five serovars and groups which are important in swine: *pomona, australis, tarassovi, canicola, icterohaemorrhagicae*, and *grippotyphosa*. Infections may be asymptomatic or cause various signs, including anorexia, pyrexia, listlessness, jaundice, abortions, still births and other vague reproductive problems, and death. After acute infection, leptospires frequently localize in the kidneys or reproductive organs consisting of scattered small grey foci of a focal interstitial nephritis, and are shed in the urine, sometimes in large numbers for months or years. Because the organisms survive in surface waters for extended periods, the disease is often waterborne. In the USA, the disease is primarily due to the serovars *Leptospira hardjo, Leptospira Pomona*, and *Leptospira grippotyphosa*. Diagnosis can be difficult because antibody titers can be transient, lasting less than a month. Further, Leptospira can also be found in healthy animals. *L. australis* serovar bratislava is most commonly associated with reproductive problems. Chronically infected herds display abortions, still births and weak piglets.

Tuberculosis affects mammals, including people, birds, and swine. The causal organism, *Mycobacteritim tuberculosis*, is sub-classified into types, human, bovine and avian. The avian type is referred to as *M. avium* or more often the avian/intracellilare complex because it is not a uniform species. *M. avium* itself infects mainly birds but is also found in the environment along with *M. intracellilare* which is predominantly saprophytic or free living. Pigs are rarely infected by the human or bovine types but are commonly infected by the avian/intracellulare complex. The avian/intracellulare complex also causes sub-clinical non-progressive infection in healthy people. The main concern is that it could cause more serious disease in immuno-suppressed people and people with AIDS. In most countries if lesions are found in the neck at slaughter the whole head is condemned and if they are found in the mesenteric lymph nodes which drain the intestines the offals are condemned. If they are more widespread in the body, which is rare, the whole carcass may be condemned or cooked. If small lesions are missed by the meat inspector normal kitchen cooking destroys the organism. In all pigs, infection causes small nodules in the lymph nodes of the neck and those that drain the small intestine. In the great majority of cases the lesions are non-progressive, they do not spread through the body, do not make the pig ill and are not excreted. There are no clinical symptoms and there is no difference in performance between infected and non-infected pigs.

*Mycoplasma hyopneumoniae* (*M hyo*) is a small bacterium (400-1200 nm) classified in the mycoplasmataceae family. *M hyo* is associated with Enzootic Pneumonia, a swine respiratory disease commonly seen in growing and finishing pigs. *M hyo* attacks the cilia of epithelial cells of the windpipe and lungs, causing the cilia to stop beating (ciliostasis) and eventually causing areas of the lungs to collapse. Depending on the extent of the disease, daily live weight gain of infected swine can be reduced by up to 17%. Enzootic Pneumonia is widespread in swine populations and present in almost every swine herd. *M hyo* is considered to be a primary pathogen that facilitates entry of PRRSV and other respiratory pathogens into the lungs. Three separate strains, 232, J & 7448 have had their genomes sequenced (Minion et al., J. Bacteriol. 186: 7123-33, 2004; Vasconcelos et al., J. Bacteriol. 187: 5568-77, 2005).

*Parvovirus* is a disease characterized by reproductive problems in pigs. The causal agent is a small DNA non-enveloped virus. Fetuses are the only affected group and the effect on the fetus depends upon the age at which it becomes infected. At 10-30 days of age, infection results in death and reabsorbtion of the fetus. Between 30-70 days of age, infection results in death and mummification. And from 70 days to term, infection results in the birth of weak piglets and mummification. The disease is able to cross the placenta and then move to each fetus along the uterus. In the sow, the clinical signs are still births, mummified piglets, embryonic deaths, infertility, and the production of a significantly reduced number of live-born offspring. Abortion is not a characteristic feature of parvovirus infection.

*Pneumonic pasteurellosis* is caused by *Pasteurella multocida*. Infection by the causal agent generally represents the final stage of the post-weaning respiratory syndrome. Clinical signs appear in three forms, the acute form is most commonly associated with *P. multocida* serotype B. Animals present with dyspnoea, labored breathing, thumping, high fever (42.2 Celsius), prostration, and finally death. In some cases the abdomen becomes purple with discoloration. A second form is a sub-acute form characterized by pleuritis, coughing, and difficulty in breathing. Pigs can lose significant amounts of weight and may have poor or no growth with serious consequences in pig flow. The chronic form presents with the occasional cough, thumping, and little or no fever. This form generally affects pigs from 10-16 weeks of age.

Porcine circovirus is a small (17-22 nm in diameter), icosahedral, non-enveloped DNA virus, which contains a single-stranded circular genome. Porcine circovirus type 2 PCV2 shares approximately 80% sequence identity with porcine circovirus type 1 (PCV1). However, in contrast with PCV1, which is generally non-virulent, swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In some affected swine, a combination of all symptoms will be apparent while other swine will only have one or two of these symptoms. During necropsy, microscopic and macroscopic lesions also appear on multiple tissues and organs, with lymphoid organs being the most common site for lesions. A strong correlation has been observed between the amount of PCV2 nucleic acid or antigen and the severity of microscopic lymphoid lesions. Mortality rates for swine infected with PCV2 can approach 80%.

Porcine Reproductive and Respiratory Syndrome (PRRS) is caused by a virus which was first isolated and classified as an arterivirus as recently as 1991. The disease syndrome had been first recognized in the USA in the mid 1980's and was called "mystery swine disease". It has also been called blue ear disease. The name porcine arterivirus has been proposed recently. The virus of PRRS has a particular affinity for the macrophages particularly those found in the lung. Macrophages are part of the body defenses. Those present in the lung are called alveolar macrophages. They ingest and remove invading bacteria and viruses, but not in the case of the PRRS virus. Instead, the virus multiplies inside them producing more virus and killing the macrophages. Once it has entered a herd it tends to remain present and active indefinitely. Up to 40% of the macrophages are destroyed which removes a major part of the bodies defense mechanism and allows bacteria and other viruses to proliferate and do damage. A common example of this is the noticeable increase in severity of enzootic pneumonia in grower/finisher units when they become infected with PRRS virus. It may take up to a year for all breeding stock, particularly in large herds, to become infected for the first time and although the virus appears to spread rapidly in a herd it may be some 4-5 months before at least 90% of the sows have become sero-positive. Some sows remain naive. Furthermore, it is not uncommon for sow herds 1-2 years after infection to contain less than 20% of serological positive animals. This does not however necessarily mean they are not still immune nor does it mean that they have stopped passing on immunity to their offspring. Adult animals shed virus for much shorter periods of time (14 days) compared to growing pigs which can excrete for 1-2 months. The clinical picture can vary tremendously from one herd to another. As a guide, for every three herds that are exposed to PRRS for the first time, one will show no recognizable disease, the second would show mild disease and the third, moderate to severe disease. The reasons for this are not clearly understood. However the higher the health status of the herd, the less severe are the disease effects. It may be that the virus is mutating as it multiplies, throwing up some strains that are highly virulent and some that are not. PRRS infects all types of herds including ones with high or ordinary health status and both indoor and outdoor units, irrespective of size.

*Pseudorabies*, also known as porcine rabies virus, or Suid herpes virus in which the causal agent is an enveloped herpes DNA virus. In naive herds, neonatal pigs present with a range of severe central nervous signs from fitting to severe in coordination. Posterior paralysis may result in piglets sitting in a manner that resembles dogs. Additionally, mortality is high. In weaned pigs, the central nervous signs may be reduced, but may be accompanied by an increase in respiratory signs. Oftentimes, respiratory diseases are associated with secondary infections. Weaned pigs can waste and suffer ill thrift and are often stunted. In growing pigs, the central nervous signs continue to reduce while the respiratory signs increase. The degree of respiratory disease depends on the presence and severity of secondary infections. In adults, reproductive signs predominate. Sows may abort and animals infected close to term are likely to give birth to stillborn or weak piglets. In established herds, there may be few clinical signs.

Rotavinis infection is a virus infection that is widespread in pig populations. It is present in most if not all pig herds with virtually a 100% sero-conversion in adult stock. A further epidemiological feature is its persistence outside the pig where it is resistant to environmental changes and many disinfectants. Maternal antibodies persist for 3-6 weeks after which pigs become susceptible to infection but exposure does not necessarily result in disease. It is estimated that only 10-15% of diarrheas in pigs are initiated by a primary rotavirus infection. In a mature herd disease appears after piglets are 7 to 10 days of age. It becomes progressively less important with age. However if pathogenic strains of E. coli are present, severe disease can occur with heavy mortality.

Infection with Salmonella spp can produce diarrhea in animals of all ages, especially those that are stressed, closely stocked, or exposed to a heavily contaminated feed or water supply. Salmonellosis is caused by many species of salmonellae and characterized clinically by one or more of three major syndromes—septicemia, acute enteritis, and chronic enteritis. The incidence has increased with the intensification of livestock production. Although various types of Salmonella can cause infections in pigs, the classic salmonellas found in swine are S. choleraesuis and S. typhimurium. Their resulting clinical patterns of most salmonella are not distinct and different species of salmonellae tend to differ in their epidemiology. Plasmid profile and drug-resistance patterns are sometimes useful markers for epidemiologic studies. Septicemic salmonellosis is often associated with S choleraesuis. Infected piglets demonstrate a reluctance to move, anorexia, a high fever of 40.5C -41.6C, and may have a shallow cough. Piglets may also be found dead with cyanotic extremities. S choleraesuis is one of the rare diseases that can cause both pneumonia and diarrhea and mortality of infected piglets is often high. Enterocolitis is generally associated with the more common S typhimurium. Infections are characterized by yellow or watery diarrhea that may contain blood or mucus as the infection progresses. Mortality is low and often associated with dehydration and potassium deficiency from the diarrhea. Feces of infected animals can contaminate feed and water, fresh and processed meats from abattoirs, plant and animal products used as fertilizers or feedstuffs, pasture and rangeland, and many inert materials. Although S choleraesuis is rarely found in feed. It can also be passed directly from contact with an infected animal. Salmonella can survive for months in wet, warm areas such as in feeder pig barns or in water dugouts. Rodents and wild birds also are sources of infection. The prevalence of infection varies among species and countries and is much higher than the incidence of clinical disease, which is commonly precipitated by stressful situations such as sudden deprivation of feed, transportation, drought, crowding, parturition, and the administration of some drugs.

Exudative epidermitis is caused by the bacterium Staphylococcus hyicus which lives normally on the skin without causing disease. It is not known why sometimes it flares up and causes a dermatitis which oozes greasy fluid. It produces toxins which are absorbed into the system and damage the liver and kidneys. In the sucking piglet disease, is usually confined to individual animals, but it can be a major problem in new gilt herds and weaned pigs. During the days immediately preceding farrowing, the bacterium multiples profusely in the sow's vagina so that piglets are infected during the birth process or soon after. Symptoms in sows include uncommon but localized lesions that may be seen particularly behind the face and eyes. Severely affected piglets will die. In piglets, symptoms include localized lesions on the flanks and behind ears. Lesions usually commence with small, dark, localized areas of infection around the face or on the legs. The skin along the flanks the belly and between the legs changes to a brown color gradually involving the whole of the body. The skin becomes wrinkled with flaking of large areas and it has a greasy feel. In severe cases the skin turns black due to necrosis and the piglets die. A more localized picture is seen if the sow has passed some immunity to the piglet, with small circumscribed lesions approximately 5-10 mm in diameter that do not spread. For weaners and growers, symptoms usually commence about 3 days after weaning with localized, brown areas of infection or dermatitis around the face or on the legs, where the skin has been damaged. It may ulcerate. The skin along the flanks the belly and between the legs changes to a brown color gradually involving the whole of the body. The skin becomes wrinkled with flaking of large areas and progresses to a dark greasy texture and in severe cases turns black. Such cases usually die due to the toxins produced by the staphylococci organisms. In nurseries, up to 15% of the population may be involved and dehydration is common.

Streptococcal meningitis causes inflammation of the meninges which are the membranes covering the brain. In the sucking piglet, it is usually caused by bacteria of Streptococcus spp, e.g. Streptococcus suis, Haemophilus parasuis, or sometimes bacteria such as E. coli and other streptococci. S. suis has many serotypes. In most countries, S. suis type 1 is the main one in sucking piglets, but this may not be true in other countries. For example, in Denmark it is type 7. S. suis also causes joint problems particularly types 1 and 14. S. suis is carried for long periods in the tonsils and may be transmitted to the sucking piglet from the sow or from other piglets. The sow also provides a variable level of immunity in the colostrum. Streptococcal meningitis in sucking piglets is sporadic in individual piglets. Streptococcal meningitis may be worse in sucking pigs when the organism has been introduced into the herd for the first time, or where it is secondary to infection with PRRS.

Aujeszky's disease, or AD, is an important disease of pigs caused by swine herpes virus. The virus can remain hidden in nerves of the pig in a carrier state for long periods of time and then be reactivated. Once introduced into a herd the virus usually remains there and it can continually affect reproductive performance at varying levels. The virus can survive for up to three weeks outside the pig. Acute outbreaks of disease occur when virulent strains of the virus first infect an unvaccinated susceptible herd. The virus crosses the uterus and placenta and infects the fetuses. The pig is the main host. However, dogs and cattle may also become infected, show nervous signs, and die.

Swine Influenza Virus causes swine flu and belongs to the influenza Type A virus group. In naive herds, clinical signs may present in explosive outbreaks with all or many animals becoming ill at the same time. Animals may present with inactivity, depression, huddling/pilling and anorexia. The animals are often mouth-breathing and breathing is labored. Coughing may ensue upon movement. Other clinical signs include a nasal discharge and puffy eyes with rectal temperatures between 40.5-41.5° Celsius. The high temperatures in a breeding stock can result in abortions, infertility, production of small weak litters, and increased still births. In established herds, annual reinfection appears.

Swine Pox is a disease which causes skin lesions, paules, pustules and scabs. It is caused by Swine pox virus.

Swine Vesicular Disease (SVD) is a different virus from the virus that causes foot and mouth disease (FMD). However, it produces a disease in pigs that is clinically indistinguishable from FMD. This disease should always be considered if sudden widespread lameness appears with vesicles or blisters on the snout, tongue and tops of the claws.

Transmissible gastroenteritis (TGE) is a disease of the intestines caused by a coronavirus (Transmissible gastroenteritis virus). It is in the same family as Porcine respiratory coronavirus, epidemic diarrhea virus, and Hemagglutinating encephalomyelitis virus. Initial clinical signs are watery diarrhea, vomiting, and anorexia. Piglets less than 21 days of age generally die, weaners become unthrifty, while growers, finishers, and adults are generally mildly affected and will survive if provided with adequate water.

DESCRIPTION OF THE INVENTION

The present invention provides combination vaccines which comprise i) an immunological agent effective for reducing the incidence of or lessening the severity of PPE caused by *L. intracelhilaris*, and ii) one or more immunological active components effective in treatment and/or prophylaxis of at least one further disease-causing organism for swine. In particular, the immunological agent effective for reducing the incidence of or lessening the severity of PPE is *L. intracellularis*.

As used herein, the term "*L. intracellularis*" means the intracellular, curved gram-negative bacteria described in detail by C. Gebhart et al., Int'l. J. of Systemic Bacteriology, Vol. 43, No. 3, 533-538 (1993) and S. McOrist et al., Int'l. J. of Systemic Bacteriology, Vol. 45, No. 4, 820-825 (1995), each of which is incorporated herein by reference in their entireties, and includes but is not limited to the isolates described in WO 96/39629 and WO 05/011731. In particular, the term "*L. intracellularis*" also means, but is not limited to the isolates deposited under the Budapest Treaty with the American Type Culture Collection, 10801 University Boulevard, Manassas, Va. 20110-2209 and assigned ATCC accession number PTA 4926 or ATCC accession number 55783. Both isolates are described in WO 96/39629 and WO 05/011731, respectively. The term "*L. intracellularis*"also means, but is not limited to any other *L. intracellularis* bacteria strain or isolate preferably having the immunogenic properties of at least one of the *L. intracellularis* strains described in WO 96/39629 and WO 05/011731, in particular having the immunogenic properties of at least one of the isolates deposited under the Budapest Treaty with the American Type Culture Collection, 10801 University Boulevard, Manassas, Va. 20110-2209 and assigned ATCC accession numbers PTA 4926 or ATCC accession number 55783.

A strain or isolate has the "immunogenic properties" of at least one of the *L. intracellularis* strains described in WO 96/39629 and WO 05/011731, in particular, of the isolates deposited as ATCC accession number PTA 4926 or ATCC accession number 55783, when it is detectable at least with one of the anti-*L. intracellularis* specific antibodies, described in WO06/01294, in a detection assay that is also described in WO06/01294. Preferably those antibodies are selected from the antibodies having the reference numbers 301:39, 287:6, 268:29, 110:9, 113:2 and 268:18. Preferably, the detection assay is a sandwich ELISA as described in Examples 2 and 3 of WO06/12949, whereas antibody 110:9 is used as an capture antibody and antibody 268:29 is used as conjugated antibody. All antibodies disclosed in WO06/12949 are produced by hybridoma cells, which are deposited at the Centre for Applied Microbiology and Research (CAMR) and European Collection of Cell Cultures (ECACC) ", Salisbury, Wiltshire SP4 OJG, UK, as a patent deposit according to the Budapest Treaty. The date of deposit was May 11, 2004. HYBRIDOMA CELL LINE 110:9 is successfully deposited under ECACC Acc. No. 04092204. HYBRIDOMA CELL LINE 113:2 is successfully deposited under ECACC Acc. No. 04092201. HYBRIDOMA CELL LINE 268:18 is successfully deposited under ECACC Acc. No. 04092202. HYBRIDOMA CELL LINE 268:29 is successfully deposited under ECACC Acc. No. 04092206. HYBRIDOMA CELL LINE 287:6 is successfully deposited under ECACC Acc. No. 04092203. HYBRIDOMA CELL LINE 301:39 is successfully deposited under ECACC Acc. No. 04092205.

Moreover, the term "*L intracellularis*" also means any *L. intracellularis* antigen. The term "*L. intracellularis* antigen" as used herein means, but is not limited to any composition of matter, that comprises at least one antigen that can induce, stimulate or enhance the immune response against a *L. intracellularis*-caused infection, when administered to a pig. Preferably, said *L. intracellularis* antigen is a complete *L. intracellularis* bacterium, in particular in an inactivated form (a so called killed bacterium), a modified live or attenuated *L. intracellularis* bacterium (a so called MLB), a chimeric vector that comprises at least an immunogenic amino acid sequence of *L. intracellularis*, or any other polypeptide or component, that comprises at least an immunogenic amino acid sequence of *L. intracellularis*. The terms "immunogenic protein", "immunogenic polypeptide" or "immunogenic amino acid sequence" as used herein refer to any amino acid sequence which elicits an immune response in a host against a pathogen comprising said immunogenic protein, immunogenic polypeptide or immunogenic amino acid sequence. In particular, an "immunogenic protein", "immunogenic polypeptide" or "immunogenic amino acid sequence" of *L. intracellularis* means any amino acid sequence that codes for an antigen which elicits an immunological response against *L. intracellularis* in a host to which said "immunogenic protein", "immunogenic polypeptide" or "immunogenic amino acid sequence" is administered.

An "immunogenic protein", "immunogenic polypeptide" or "immunogenic amino acid sequence" as used herein, includes but is not limited to the full-length sequence of any proteins, analogs thereof, or immunogenic fragments thereof. The term "immunogenic fragment" means a fragment of a protein which includes one or more epitopes and thus elicits the immunological response against the relevant pathogen. Such fragments can be identified using any number of epitope mapping techniques that are well known in the art. See, e.g., Epitope Mapping Protocols in Methods in Molecular Biology, Vol. 66 (Glenn E. Morris, Ed., 1996) Humana Press, Totowa, N.J. (The teachings and content of which are incorporated by reference herein.) For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. (The teachings and content of which are incorporated by reference herein.) Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, June 28-Jul. 3, 1998. (The teachings and content of which are incorporated by reference herein.)

An "immunological or immune response" to a composition or vaccine is the development in the host of a cellular and/or antibody-mediated immune response to the composition or vaccine of interest. Usually, an "immune response" includes but is not limited to one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of the symptoms associated with host infections as described above.

Suitable *L. intracellularis* antigens include, but are not limited to those described in EP 1219711; U.S. Pat. No. 6,605,696; WO 96/39629; WO97/20050; WO 00/69903; WO 00/69904; WO 00/69905; WO 00/69906; WO 02/38594; WO 02/26250; WO 03/006665; WO 04/033631; WO 05/026200; WO 05/011731.

As described above, the present invention relates to combination vaccines which comprise i) an immunological agent effective for reducing the incidence of or lessening the severity of PPE caused by *L. intracellularis*, and ii) one or more immunological active components effective in the treatment and/or prophylaxis of at least one further disease-causing organism for swine. Preferably the further disease-causing organism for swine is selected from the group consisting of: enteric pathogens which include *Salmonella* spp. (1), in particular *S. typhimurium* (1a), *S. choleraesuis* (1b); Astroviruses (2); Rotavirus (3); Transmissible gastroenteritis virus (4); *Brachyspira* spp (5)., in particular B. hyodysenteriae (5a), *B. pilosicoli* (5b); *Clostridium* spp. (6), in particular *C. difficile* (6a), *C. perfringens* types A, B and C (6b), *C. novyi* (6c), *C. septicum* (6d), *C. tetani* (6e); Porcine enteric picomaviruses (7); Porcine enteric caliciviruses (8);respiratory pathogens, which include: *Actinobacillus pleuropneumonia* (9); *Bordetella bronchiseptica* (10); *Erysipelothrix rhsiopathiae* (11); *Haemophilus parasuis* (12), in particular subtypes 1, 7 and 14; *Pasteurella* spp. (13), in particular *P. multocida* (13a); *Mycoplasma* spp. (14), in particular *M. hyopneumoniae* (14a), *M. hyorhinis* (14b); Swine influenza virus (15); PRRS virus (16); Porcine circovirus (17); Porcine parvovirus (18); Pseudorabies virus (19); *Eperythrozoonosis suis* (20) *Mycobacterium* spp. (21), in particular *M. avium* (21a), *M. intracellulare* (21b), *M. bovis* (21c); Porcine respiratory corona virus (22); *Arcanobacterium pyogenes* (23); Porcine adenovirus (24); Clasical swine fever (25); Porcine cytomegalovirus (26); African swine fever (27); or other pathogens, which include *Escherichia coli* (28), *Streptococcus* spp. (29), in particular *S. suis* (29a), *S. porcinus* (29b), *S. dysgalactiae* (29c), preferably subsp. *equisimilis* (29c1); *Brucella suis* (30), in particular biovars 1, 2 and 3; *Leptospira* spp. (31), in particular *L. australis* (31a), *L. canicola* (31b), *L. grippotyphosa* (31c), *L. pomona* (31d), *L. icterohaemorrhagicae* (31e), *L. interrogans* (31f), *L. tarassovi* (31g), *L. hardjo* (31h), L. sejroe (31i); Encephalomyocarditis virus (32); Hemagglutinating encephalomyelitis virus (33); Japanese encephalitis virus (34); West Nile virus (35); Reovirus (36); Rubulavirus (37); Menangle virus (38); Nipah virus (39); Vesicular stomatitis virus (40); Virus of vesicular exanthema of swine (41); Swine pox virus (42); Swine herpes virus (43); and *Staphylococcus hyicus* (44).

Any reference made in the following to one or more of the swine pathogens listed-above is made either by naming the pathogen, for example *M hyopneumoniae*, or by making reference to the number that is put in parentheses behind the pathogen, e.g. (*M. hyopneumoniae*=(14a)).

Thus, the present invention relates to a combination vaccine for the treatment and/or prophylaxis of swine, that comprises i) an immunological agent effective for reducing the incidence of or lessening the severity of an *L. intracellularis* infection, preferably a *L. intracelluluaris* antigen, and ii) one or more immunological active component(s) effective for the treatment and/or prophylaxis of infections caused by one or more of the swine pathogens selected from the group consisting of: (1), (1a), (1b), (2), (3), (4), (5), (5a), (5b), (6), (6a), (6b), (6c), (6d), (6e), (7), (8), (9), (10), (11), (12), (13), (13a), (14), (14a), (14b), (15), (16), (17), (18), (19), (20), (21), (21a), (21b), (21c), (22), (23), (24), (25), (26), (27), (28), (29), (29a), (29b), (29c), (29c1), (30), (31) (31a), (31b), (31c), (31d), (31e), (31f), (31g), (31h), (31i), (32), (33), (34), (35), (36), (37), (38), (39), (40), (41), (42), (43) and (44). Preferably the immunological active component of said combination vaccine comprises or consists of one or more modified live microorganisms, one or more killed-microorganisms, or one or more immunological active part(s) of one or more microorganisms selected from the group consisting of (1), (1a), (1b), (2), (3), (4), (5), (5a), (5b), (6), (6a), (6b), (6c), (6d), (6e), (7), (8), (9), (10), (11), (12), (13), (13a), (14), (14a), (14b), (15), (16), (17), (18), (19), (20), (21), (21a), (21b), (21c), (22), (23), (24), (25), (26), (27), (28), (28), (29), (29a), (29b), (29c), (29c1), (30), (31) (31a), (31b), (31c), (31d), (31e), (31f), (31g), (31h), (31i), (32), (33), (34), (35), (36), (37), (38), (39), (40), (41), (42), (43) and (44). [combo 1].

An "immunological active component" as used herein means a component that induces or stimulates the immune response in an animal to which said component is administered. Preferably, the immune response is directed to said component or to an microorganism comprising said component. According to a further preferred embodiment, the immunological active component is an attenuated microorganism, including but not limited to a modified live virus or bacterium (MLV or MLB), a killed-microorganism or at least an immunological active part of a microorganism.

"Immunological active part of a microorganism" as used herein means a protein-, sugar-, and or glycoprotein containing fraction of a microorganism that comprises at least one antigen that induces or stimulates the immune response in an animal to which said component is administered. According to a preferred embodiment, said immune response is directed to said immunological active part of the microorganism or to the microorganism that comprises said immunological active part.

Preferably the immunological active component of [combo 1] is effective for the treatment and/or prophylaxis of infections caused by the swine pathogen (11) [combo 2], preferably said immunological active component comprises a live modified form, a killed form, or an immunological active part of said swine pathogen (11) [combo 3].

According to a further embodiment the immunological active component of [combo 1] is effective for the treatment and/or prophylaxis of infections caused by the swine pathogen (9) [combo 4], preferably said immunological active component comprises a live modified form, a killed form, or an immunological active part of said swine pathogen (9) [combo 5].

According to a further embodiment the immunological active component of [combo 1] is effective for the treatment and/or prophylaxis of infections caused by the swine pathogen (10) [combo 6], preferably said immunological active component comprises a live modified form, a killed form, or an immunological active part of said swine pathogen (10) [combo 7].

According to a further embodiment the immunological active component of [combo 1] is effective for the treatment and/or prophylaxis of infections caused by the swine pathogen (12) [combo 8], preferably said immunological active component comprises a live modified form, a killed form, or an immunological active part of said swine pathogen (12) [combo 9].

According to a further embodiment the immunological active component of [combo 1] is effective for the treatment and/or prophylaxis of infections caused by the swine pathogen (13), in particular (13a) [combo 10], preferably said immunological active component comprises a live modified form, a killed form, or an immunological active part of said swine pathogen (13), in particular (13a) [combo 11].

According to a further embodiment the immunological active component of [combo 1] is effective for the treatment and/or prophylaxis of infections caused by the swine pathogen (14), in particular (14a) and/or (14b) [combo 12], preferably said immunological active component comprises a live modified form, a killed form, or an immunological active part of said swine pathogen (14), in particular (14a) and/or (14b) [combo 13].

According to a further embodiment the immunological active component of [combo 1] is effective for the treatment and/or prophylaxis of infections caused by the swine pathogen (15) [combo 14], preferably said immunological active component comprises a live modified form, a killed form, or an immunological active part of said swine pathogen (15) [combo 15].

According to a further embodiment the immunological active component of [combo 1] is effective for the treatment and/or prophylaxis of infections caused by the swine pathogen (16) [combo 16], preferably said immunological active component comprises a live modified form, a killed form, or an immunological active part of said swine pathogen (16) [combo 17].

According to a further embodiment the immunological active component of [combo 1] is effective for the treatment and/or prophylaxis of infections caused by the swine pathogen (17) [combo 18], preferably said immunological active component comprises a live modified form, a killed form, or an immunological active part of said swine pathogen (17) [combo 19].

According to a further embodiment the immunological active component of [combo 1] is effective for the treatment and/or prophylaxis of infections caused by the swine pathogen (18) [combo 20], preferably said immunological active component comprises a live modified form, a killed form, or an immunological active part of said swine pathogen (18) [combo 21].

According to a further embodiment the immunological active component of [combo 1] is effective for the treatment and/or prophylaxis of infections caused by the swine pathogen (19) [combo 22], preferably said immunological active component comprises a live modified form, a killed form, or an immunological active part of said swine pathogen (19) [combo 23].

According to a further embodiment the immunological active component of [combo 1] is effective for the treatment and/or prophylaxis of infections caused by the swine pathogen (29), in particular (29a) [combo 24], preferably said immunological active component comprises a live modified form, a killed form, or an immunological active part of said swine pathogen (29), in particular (29a) [combo 25].

According to a further embodiment the immunological active component of [combo 1] is effective for the treatment and/or prophylaxis of infections caused by the swine pathogens (1), in particular (1a) and/or (1b); and (9) [combo 26], preferably said immunological active component comprises a live modified form, a killed form, or an immunological active part of said swine pathogen (9) [combo 27].

According to a further embodiment the immunological active component of [combo 1] is effective for the treatment and/or prophylaxis of infections caused by the swine pathogens (1), in particular (1a) and/or (1b); and (10) [combo 28], preferably said immunological active component comprises a live modified form, a killed form, or an immunological active part of said swine pathogens (1), in particular (1a) and/or (1b); and (10) [combo 29].

According to a further embodiment the immunological active component of [combo 1] is effective for the treatment and/or prophylaxis of infections caused by the swine pathogens (1), in particular (1a) and/or (1b); and (11) [combo 30], preferably said immunological active component comprises a live modified form, a killed form, or an immunological active part of said swine pathogens (1), in particular (1a) and/or (1b); and (11) [combo 31].

According to a further embodiment the immunological active component of [combo 1] is effective for the treatment and/or prophylaxis of infections caused by the swine pathogens (1), in particular (1a) and/or (1b); and (12) [combo 32], preferably said immunological active component comprises a live modified form, a killed form, or an immunological active part of said swine pathogens (1), in particular (1a) and/or (1b); and (12) [combo 33].

According to a further embodiment the immunological active component of [combo 1] is effective for the treatment and/or prophylaxis of infections caused by the swine pathogens (1), in particular (1a) and/or (1b); and (13), in particular (13a) [combo 34], preferably said immunological active component comprises a live modified form, a killed form, or an immunological active part of said swine pathogens (1), in particular (1a) and/or (1b); and (13), in particular (13a) [combo 35].

According to a further embodiment the immunological active component of [combo 1] is effective for the treatment and/or prophylaxis of infections caused by the swine pathogens (1), in particular (1a) and/or (1b); and (14), in particular (14a) and/or (14b) [combo 36], preferably said immunological active component comprises a live modified form, a killed form, or an immunological active part of said swine pathogens (1), in particular (1a) and/or (1b); and (14), in particular (14a) and/or (14b) [combo 37].

According to a further embodiment the immunological active component of [combo 1] is effective for the treatment and/or prophylaxis of infections caused by the swine pathogens (1), in particular (1a) and/or (1b); and (15) [combo 38], preferably said immunological active component comprises a live modified form, a killed form, or an immunological active part of said swine pathogens (1), in particular (1a) and/or (1b); and (15) [combo 39].

According to a further embodiment the immunological active component of [combo 1] is effective for the treatment and/or prophylaxis of infections caused by the swine pathogens (1), in particular (1a) and/or (1b); and (16) [combo 40], preferably said immunological active component comprises a live modified form, a killed form, or an 20 immunological active part of said swine pathogens (1), in particular (1a) and/or (1b); and (16) [combo 41].

According to a further embodiment the immunological active component of [combo 1] is effective for the treatment and/or prophylaxis of infections caused by the swine pathogens (1), in particular (1a) and/or (1b); and (17) [combo 42], preferably said immunological active component comprises a live modified form, a killed form, or an immunological active part of said swine pathogens (1), in particular (1a) and/or (1b); and (17) [combo 43].

According to a further embodiment the immunological active component of [combo 1] is effective for the treatment and/or prophylaxis of infections caused by the swine pathogens (1), in particular (1a) and/or (1b); and (18) [combo 44], preferably said immunological active component comprises a live modified form, a killed form, or an immunological active part of said swine pathogens (1), in particular (1a) and/or (1b); and (18) [combo 45].

According to a further embodiment the immunological active component of [combo 1] is effective for the treatment and/or prophylaxis of infections caused by the swine pathogens (1), in particular (1a) and/or (1b); and (19) [combo 46], preferably said immunological active component comprises a live modified form, a killed form, or an immunological active part of said swine pathogens (1), in particular (1a) and/or (1b); and (19) [combo 47].

According to a further embodiment the immunological active component of [combo 1] is effective for the treatment and/or prophylaxis of infections caused by the swine pathogens (1), in particular (1a) and/or (1b); and (29), in particular (29a) [combo 48], preferably said immunological active component comprises a live modified form, a killed form, or an immunological active part of said swine pathogens (1), in particular (1a) and/or (1b); and (29), in particular (29a) [combo 49].

According to a further embodiment the immunological active component of [combo 1] is effective for the treatment and/or prophylaxis of infections caused by the swine pathogens (9); and (10) [combo 50], preferably said immunological active component comprises a live modified form, a killed form, or an immunological active part of said swine pathogens (9); and (10) [combo 51].

According to a further embodiment the immunological active component of [combo 1] is effective for the treatment and/or prophylaxis of infections caused by the swine pathogens (9); and (11) [combo 52], preferably said immunological active component comprises a live modified form, a killed form, or an immunological active part of said swine pathogens (9); and (11) [combo 53]. According to a more preferred embodiment, the immunological active component of [combo 1] is ENTERISOL®SC-54 (*Salmonella choleraesius*, Boehringer Ingelheim Vetmedica Inc., St. Joseph, Mo., U.S.) and INGELVAC® ERY-ALC (*Erysipelothrix rhusiopathiae*, Boehringer Ingelheim Vetmedica Inc., St. Joseph, Mo., U.S.) [combo 54]. According to a further embodiment, the *L. intracellularis* antigen of combo 54 is ENTERISOL® Ileitis FF (Boehringer Ingelheim Vetmedica Inc., St. Joseph, Mo., U.S.) [combo 55] or ENTERISOL® Ileitis Lyophilized (Boehringer Ingelheim Vetmedica GmbH, Ingelheim am Rhein, Germany) [combo 56].

According to a further embodiment the immunological active component of [combo 1] is effective for the treatment and/or prophylaxis of infections caused by the swine pathogens (9); and (12) [combo 57], preferably said immunological active component comprises a live modified form, a killed form, or an immunological active part of said swine pathogens (9); and (12) [combo 58].

According to a further embodiment the immunological active component of [combo 1] is effective for the treatment and/or prophylaxis of infections caused by the swine pathogens (9); and (13), in particular (13a) [combo 59], preferably said immunological active component comprises a live modified form, a killed form, or an immunological active part of said swine pathogens (9); and (13), in particular (13a) [combo 60].

According to a further embodiment the immunological active component of [combo 1] is effective for the treatment and/or prophylaxis of infections caused by the swine pathogens (9); and (14), in particular (14a) and/or (14b) [combo 61], preferably said immunological active component comprises a live modified form, a killed form, or an immunological active part of said swine pathogens (9); and (14), in particular (14a) and/or (14b) [combo 62].

According to a further embodiment the immunological active component of [combo 1] is effective for the treatment and/or prophylaxis of infections caused by the swine pathogens (9); and (15) [combo 63], preferably said immunological active component comprises a live modified form, a killed form, or an immunological active part of said swine pathogens (9); and (15) [combo 64].

According to a further embodiment the immunological active component of [combo 1] is effective for the treatment and/or prophylaxis of infections caused by the swine pathogens (9); and (16) [combo 65], preferably said immunological active component comprises a live modified form, a killed form, or an immunological active part of said swine pathogens (9); and (16) [combo 66].

According to a further embodiment the immunological active component of [combo 1] is effective for the treatment and/or prophylaxis of infections caused by the swine pathogens (9); and (17) [combo 67],. preferably said immunological active component comprises a live modified form, a killed form, or an immunological active part of said swine pathogens (9); and (17) [combo 68].

According to a further embodiment the immunological active component of [combo 1] is effective for the treatment and/or prophylaxis of infections caused by the swine pathogens (9); and (18) [combo 69], preferably said immunological active component comprises a live modified form, a killed form, or an immunological active part of said swine pathogens (9); and (18) [combo 70].

According to a further embodiment the immunological active component of [combo 1] is effective for the treatment and/or prophylaxis of infections caused by the swine pathogens (9); and (19) [combo 71], preferably said immunological active component comprises a live modified form, a killed form, or an immunological active part of said swine pathogens (9); and (19) [combo 72].

According to a further embodiment the immunological active component of [combo 1] is effective for the treatment and/or prophylaxis of infections caused by the swine pathogens (9); and (29), in particular (29a) [combo 73], preferably said immunological active component comprises a live modified form, a killed form, or an immunological active part of said swine pathogens (9); and (29), in particular (29a) [combo 74].

According to a further embodiment the immunological active component of [combo 1] is effective for the treatment and/or prophylaxis of infections caused by the swine pathogens (10); and (11) [combo 75], preferably said immunological active component comprises a live modified form, a killed form, or an immunological active part of said swine pathogens (10); and (I 1) [combo 76].

According to a further embodiment the immunological active component of [combo 1] is effective for the treatment and/or prophylaxis of infections caused by the swine pathogens (10); and (12) [combo 77], preferably said immunological active component comprises a live modified form, a killed form, or an immunological active part of said swine pathogens (10); and (12) [combo 78].

According to a further embodiment the immunological active component of [combo 1] is effective for the treatment and/or prophylaxis of infections caused by the swine pathogens (10); and (13), in particular (13a) [combo 79], preferably said immunological active component comprises a live modified form, a killed form, or an immunological active part of said swine pathogens (10); and (13), in particular (13a) [combo 80].

According to a further embodiment the immunological active component of [combo 1] is effective for the treatment and/or prophylaxis of infections caused by the swine pathogens (10); and (14), in particular (14a) and/or (14b) [combo 81], preferably said immunological active component comprises a live modified form, a killed form, or an immunological active part of said swine pathogens (10); and (14), in particular (14a) and/or (14b) [combo 82].

According to a further embodiment the immunological active component of [combo 1] is effective for the treatment and/or prophylaxis of infections caused by the swine pathogens (10); and (15) [combo 83], preferably said immunological active component comprises a live modified form, a killed form, or an immunological active part of said swine pathogens (10); and (15) [combo 84].

According to a further embodiment the immunological active component of [combo 1] is effective for the treatment and/or prophylaxis of infections caused by the swine pathogens (10); and (16) [combo 85], preferably said immunological active component comprises a live modified form, a killed form, or an immunological active part of said swine pathogens (10); and (16) [combo 86].

According to a further embodiment the immunological active component of [combo 1] is effective for the treatment and/or prophylaxis of infections caused by the swine pathogens (10); and (17) [combo 87], preferably said immunological active component comprises a live modified form, a killed form, or an immunological active part of said swine pathogens (10); and (17) [combo 88].

According to a further embodiment the immunological active component of [combo 1] is effective for the treatment and/or prophylaxis of infections caused by the swine pathogens (10); and (18) [combo 89], preferably said immunological active component comprises a live modified form, a killed form, or an immunological active part of said swine pathogens (10); and (18) [combo 90].

According to a further embodiment the immunological active component of [combo 1] is effective for the treatment and/or prophylaxis of infections caused by the swine pathogens (10); and (19) [combo 91], preferably said immunological active component comprises a live modified form, a killed form, or an immunological active part of said swine pathogens (10); and (19) [combo 92].

According to a further embodiment the immunological active component of [combo 1] is effective for the treatment and/or prophylaxis of infections caused by the swine pathogens (10); and (29), in particular (29a) [combo 93], preferably said immunological active component comprises a live modified form, a killed form, or an immunological active part of said swine pathogens (10); and (29), in particular (29a) [combo 94].

According to a further embodiment the immunological active component of [combo 1] is effective for the treatment and/or prophylaxis of infections caused by the swine pathogens (11); and (12) [combo 95], preferably said immunological active component comprises a live modified form, a killed form, or an immunological active part of said swine pathogens (11); and (12) [combo 96].

According to a further embodiment the immunological active component of [combo 1] is effective for the treatment and/or prophylaxis of infections caused by the swine pathogens (11); and (13), in particular (13a) [combo 97], preferably said immunological active component comprises a live modified form, a killed form, or an immunological active part of said swine pathogens (11); and (13), in particular (13a) [combo 98].

According to a further embodiment the immunological active component of [combo 1] is effective for the treatment and/or prophylaxis of infections caused by the swine pathogens (11); and (14), in particular (14a) and/or (14b) [combo 99], preferably said immunological active component comprises a live modified form, a killed form, or an immunological active part of said swine pathogens (11); and (14), in particular (14a) and/or (14b) [combo 100].

According to a further embodiment the immunological active component of [combo 1] is effective for the treatment and/or prophylaxis of infections caused by the swine pathogens (11); and (15) [combo 101], preferably said immunological active component comprises a live modified form, a killed form, or an immunological active part of said swine pathogens (11); and (15) [combo 102].

According to a further embodiment the immunological active component of [combo 1] is effective for the treatment and/or prophylaxis of infections caused by the swine pathogens (11); and (16) [combo 103], preferably said immunological active component comprises a live modified form, a killed form, or an immunological active part of said swine pathogens (11); and (16) [combo 104].

According to a further embodiment the immunological active component of [combo 1] is effective for the treatment and/or prophylaxis of infections caused by the swine pathogens (11); and (17) [combo 105], preferably said immunological active component comprises a live modified form, a killed form, or an immunological active part of said swine pathogens (11); and (17) [combo 106].

According to a further embodiment the immunological active component of [combo 1] is effective for the treatment and/or prophylaxis of infections caused by the swine pathogens (11); and (18) [combo 107], preferably said immunological active component comprises a live modified form, a killed form, or an immunological active part of said swine pathogens (11); and (18) [combo 108].

According to a further embodiment the immunological active component of [combo 1] is effective for the treatment and/or prophylaxis of infections caused by the swine pathogens (11); and (19) [combo 109], preferably said immunological active component comprises a live modified form, a killed form, or an immunological active part of said swine pathogens (11); and (19) [combo 110].

According to a further embodiment the immunological active component of [combo 1] is effective for the treatment and/or prophylaxis of infections caused by the swine pathogens (11); and (29), in particular (29a) [combo 111], preferably said immunological active component comprises a live modified form, a killed form, or an immunological active part of said swine pathogens (11); and (29), in particular (29a) [combo 112].

According to a further embodiment the immunological active component of [combo 1] is effective for the treatment and/or prophylaxis of infections caused by the swine pathogens (12); and (13), in particular (13a) [combo 113], preferably said immunological active component comprises a live modified form, a killed form, or an immunological active part of said swine pathogens (12); and (13), in particular (13a) [combo 114].

According to a further embodiment the immunological active component of [combo 1] is effective for the treatment and/or prophylaxis of infections caused by the swine pathogens (12); and (14), in particular (14a) and/or (14b) [combo 115], preferably said immunological active component comprises a live modified form, a killed form, or an immunological active part of said swine pathogens (12); and (14), in particular (14a) and/or (14b) [combo 116].

According to a further embodiment the immunological active component of [combo 1] is effective for the treatment and/or prophylaxis of infections caused by the swine pathogens (12); and (15) [combo 117], preferably said immunological active component comprises a live modified form, a killed form, or an immunological active part of said swine pathogens (12); and (15) [combo 118].

According to a further embodiment the immunological active component of [combo 1] is effective for the treatment and/or prophylaxis of infections caused by the swine pathogens (12); and (16) [combo 119], preferably said immunological active component comprises a live modified form, a killed form, or an immunological active part of said swine pathogens (12); and (16) [combo 120].

According to a further embodiment the immunological active component of [combo 1] is effective for the treatment and/or prophylaxis of infections caused by the swine pathogens (12); and (17) [combo 121], preferably said immunological active component comprises a live modified form, a killed form, or an immunological active part of said swine pathogens (12); and (17) [combo 122].

According to a further embodiment the immunological active component of [combo 1] is effective for the treatment and/or prophylaxis of infections caused by the swine pathogens (12); and (18) [combo 123], preferably said immunological active component comprises a live modified form, a killed form, or an immunological active part of said swine pathogens (12); and (18) [combo 124].

According to a further embodiment the immunological active component of [combo 1] is effective for the treatment and/or prophylaxis of infections caused by the swine pathogens (12); and (19) [combo 125], preferably said immunological active component comprises a live modified form, a killed form, or an immunological active part of said swine pathogens (12); and (19) [combo 126].

According to a further embodiment the immunological active component of [combo 1] is effective for the treatment and/or prophylaxis of infections caused by the swine pathogens (12); and (29), in particular (29a) [combo 127], preferably said immunological active component comprises a live modified form, a killed form, or an immunological active part of said swine pathogens (12); and (29), in particular (29a) [combo 128].

According to a further embodiment the immunological active component of [combo 1] is effective for the treatment and/or prophylaxis of infections caused by the swine pathogens (13), in particular (13a); and (14), in particular (14a) and/or (14b) [combo 129], preferably said immunological active component comprises a live modified form, a killed form, or an immunological active part of said swine pathogens (13), in particular (13a); and (14), in particular (14a) and/or (14b) [combo 130].

According to a further embodiment the immunological active component of [combo 1] is effective for the treatment and/or prophylaxis of infections caused by the swine pathogens (13), in particular (13a); and (15) [combo 131], preferably said immunological active component comprises a live modified form, a killed form, or an immunological active part of said swine pathogens (13), in particular (13a); and (15) [combo 132].

According to a further embodiment the immunological active component of [combo 1] is effective for the treatment and/or prophylaxis of infections caused by the swine pathogens (13), in particular (13a); and (16) [combo 133], preferably said immunological active component comprises a live modified form, a killed form, or an immunological active part of said swine pathogens (13), in particular (13a); and (16) [combo 134].

According to a further embodiment the immunological active component of [combo 1] is effective for the treatment and/or prophylaxis of infections caused by the swine pathogens (13), in particular (13a); and (17) [combo 135], preferably said immunological active component comprises a live modified form, a killed form, or an immunological active part of said swine pathogens (13), in particular (13a); and (17) [combo 136].

According to a further embodiment the immunological active component of [combo 1] is effective for the treatment and/or prophylaxis of infections caused by the swine pathogens (13), in particular (13a); and (18) [combo 137], preferably said immunological active component comprises a live modified form, a killed form, or an immunological active part of said swine pathogens (13), in particular (13a); and (18) [combo 138].

According to a further embodiment the immunological active component of [combo 1] is effective for the treatment and/or prophylaxis of infections caused by the swine pathogens (13), in particular (13a); and (19) [combo 139], preferably said immunological active component comprises a live modified form, a killed form, or an immunological active part of said swine pathogens (13), in particular (13a); and (19) [combo 140].

According to a further embodiment the immunological active component of [combo 1] is effective for the treatment and/or prophylaxis of infections caused by the swine pathogens (13), in particular (13a); and (29), in particular (29a) [combo 141], preferably said immunological active component comprises a live modified form, a killed form, or an immunological active part of said swine pathogens (13), in particular (13a); and (29), in particular (29a) [combo 142].

According to a further embodiment the immunological active component of [combo 1] is effective for the treatment and/or prophylaxis of infections caused by the swine pathogens (14), in particular (14a); and (15) [combo 143], preferably said immunological active component comprises a live modified form, a killed form, or an immunological active part of said swine pathogens (14), in particular (14a); and (15) [combo 144].

According to a further embodiment the immunological active component of [combo 1] is effective for the treatment and/or prophylaxis of infections caused by the swine pathogens (14), in particular (14a); and (16) [combo 145], preferably said immunological active component comprises a live modified form, a killed form, or an immunological active part of said swine pathogens (14), in particular (14a); and (16) [combo 146].

According to a further embodiment the immunological active component of [combo 1] is effective for the treatment and/or prophylaxis of infections caused by the swine pathogens (14), in particular (14a); and (17) [combo 147], preferably said immunological active component comprises a live modified form, a killed form, or an immunological active part of said swine pathogens (14), in particular (14a); and (17) [combo 148].

According to a further embodiment the immunological active component of [combo 1] is effective for the treatment and/or prophylaxis of infections caused by the swine pathogens (14), in particular (14a); and (18) [combo 149], preferably said immunological active component comprises a live modified form, a killed form, or an immunological active part of said swine pathogens (14), in particular (14a); and (18) [combo 150].

According to a further embodiment the immunological active component of [combo 1] is effective for the treatment and/or prophylaxis of infections caused by the swine pathogens (14), in particular (14a); and (19) [combo 151], preferably said immunological active component comprises a live modified form, a killed form, or an immunological active part of said swine pathogens (14), in particular (14a); and (19) [combo 152].

According to a further embodiment the immunological active component of [combo 1] is effective for the treatment and/or prophylaxis of infections caused by the swine pathogens (14), in particular (14a); and (29), in particular (29a) [combo 153], preferably said immunological active component comprises a live modified form, a killed form, or an immunological active part of said swine pathogens (14), in particular (14a); and (29), in particular (29a) [combo 154].

According to a further embodiment the immunological active component of [combo 1] is effective for the treatment and/or prophylaxis of infections caused by the swine pathogens (15); and (16) [combo 155], preferably said immunological active component comprises a live modified form, a killed form, or an immunological active part of said swine pathogens (15); and (16) [combo 156].

According to a further embodiment the immunological active component of [combo 1] is effective for the treatment and/or prophylaxis of infections caused by the swine pathogens (15); and (17) [combo 157], preferably said immunological active component comprises a live modified form, a killed form, or an immunological active part of said swine pathogens (15); and (17) [combo 158].

According to a further embodiment the immunological active component of [combo 1] is effective for the treatment and/or prophylaxis of infections caused by the swine pathogens (15); and (18) [combo 159], preferably said immunological active component comprises a live modified form, a killed form, or an immunological active part of said swine pathogens (15); and (18) [combo 160].

According to a further embodiment the immunological active component of [combo 1] is effective for the treatment and/or prophylaxis of infections caused by the swine pathogens (15); and (19) [combo 161], preferably said immunological active component comprises a live modified form, a killed form, or an immunological active part of said swine pathogens (15); and (19) [combo 162].

According to a further embodiment the immunological active component of [combo 1] is effective for the treatment and/or prophylaxis of infections caused by the swine pathogens (15); and (29), in particular (29a) [combo 163], preferably said immunological active component comprises a live modified form, a killed form, or an immunological active part of said swine pathogens (15); and (29), in particular (29a) [combo 164].

According to a further embodiment the immunological active component of [combo 1] is effective for the treatment and/or prophylaxis of infections caused by the swine pathogens (16); and (17) [combo 165], preferably said immunological active component comprises a live modified form, a killed form, or an immunological active part of said swine pathogens (16); and (17) [combo 166].

According to a further embodiment the immunological active component of [combo 1] is effective for the treatment and/or prophylaxis of infections caused by the swine pathogens (16); and (18) [combo 167], preferably said immunological active component comprises a live modified form, a killed form, or an immunological active part of said swine pathogens (16); and (18) [combo 168].

According to a further embodiment the immunological active component of [combo 1] is effective for the treatment and/or prophylaxis of infections caused by the swine pathogens (16); and (19) [combo 169], preferably said immunological active component comprises a live modified form, a killed form, or an immunological active part of said swine pathogens (16); and (19) [combo 170].

According to a further embodiment the immunological active component of [combo 1] is effective for the treatment and/or prophylaxis of infections caused by the swine pathogens (16); and (29), in particular (29a) [combo 171], preferably said immunological active component comprises a live modified form, a killed form, or an immunological active part of said swine pathogens (16); and (29), in particular (29a) [combo 172].

According to a further embodiment the immunological active component of [combo 1] is effective for the treatment and/or prophylaxis of infections caused by the swine pathogens (17); and (18) [combo 173], preferably said immunological active component comprises a live modified form, a killed form, or an immunological active part of said swine pathogens (17); and (18) [combo 174].

According to a further embodiment the immunological active component of [combo 1] is effective for the treatment and/or prophylaxis of infections caused by the swine pathogens (17); and (19) [combo 175], preferably said immunological active component comprises a live modified form, a killed form, or an immunological active part of said swine pathogens (17); and (19) [combo 176].

According to a further embodiment the immunological active component of [combo 1] is effective for the treatment and/or prophylaxis of infections caused by the swine pathogens (17); and (29), in particular (29a) [combo 177], preferably said immunological active component comprises a live modified form, a killed form, or an immunological active part of said swine pathogens (17); and (29), in particular (29a) [combo 178].

According to a further embodiment the immunological active component of [combo 1] is effective for the treatment and/or prophylaxis of infections caused by the swine pathogens (18); and (19) [combo 179], preferably said immunological active component comprises a live modified form, a killed form, or an immunological active part of said swine pathogens (18); and (19) [combo 180].

According to a further embodiment the immunological active component of [combo 1] is effective for the treatment and/or prophylaxis of infections caused by the swine pathogens (18); and (29), in particular (29a) [combo 181], preferably said immunological active component comprises a live modified form, a killed form, or an immunological active part of said swine pathogens (18); and (29), in particular (29a) [combo 182].

According to a further embodiment the immunological active component of [combo 1] is effective for the treatment and/or prophylaxis of infections caused by the swine pathogens (19); and (29), in particular (29a) [combo 183], preferably said immunological active component comprises a live modified form, a killed form, or an immunological active part of said swine pathogens (19); and (29), in particular (29a) [combo 184].

According to a further embodiment the immunological active component of [combo 1] is effective for the treatment and/or prophylaxis of infections caused by the swine pathogens (1), in particular (1a) and/or (1b); (9); and (10) [combo 185], preferably said immunological active component comprises a live modified form, a killed form, or an immunological active part of said swine pathogens (1), in particular (1a) and/or (1b); (9); and (10) [combo 186].

According to a further embodiment the immunological active component of [combo 1] is effective for the treatment and/or prophylaxis of infections caused by the swine pathogens (1), in particular (1a) and/or (1b); (9); and (11) [combo 187], preferably said immunological active component comprises a live modified form, a killed form, or an immunological active part of said swine pathogens (1), in particular (1a) and/or (1b); (9); and (11) [combo 188].

According to a further embodiment the immunological active component of [combo 1] is effective for the treatment and/or prophylaxis of infections caused by the swine pathogens (1), in particular (1a) and/or (1b); (9); and (12) [combo 189], preferably said immunological active component comprises a live modified form, a killed form, or an immunological active part of said swine pathogens (1), in particular (1a) and/or (1b); (9); and (12) [combo 190].

According to a further embodiment the immunological active component of [combo 1] is effective for the treatment and/or prophylaxis of infections caused by the swine pathogens (1), in particular (1a) and/or. (1b); (9); and (13), in particular (13a) [combo 191], preferably said immunological active component comprises a live modified form, a killed form, or an immunological active part of said swine pathogens (1), in particular (1a) and/or (1b); (9); and (13), in particular (13a) [combo 192].

According to a further embodiment the immunological active component of [combo 1] is effective for the treatment and/or prophylaxis of infections caused by the swine pathogens (1), in particular (1a) and/or (1b); (9); and (14), in particular (14a) and/or (14b) [combo 193], preferably said immunological active component comprises a live modified form, a killed form, or an immunological active part of said swine pathogens (1), in particular (1a) and/or (1b); (9); and (14), in particular (14a) and/or (14b) [combo 194].

According to a further embodiment the immunological active component of [combo 1] is effective for the treatment and/or prophylaxis of infections caused by the swine pathogens (1), in particular (1a) and/or (1b); (9); and (15) [combo 195], preferably said immunological active component comprises a live modified form, a killed form, or an immunological active part of said swine pathogens (1), in particular (1a) and/or (1b); (9); and (15) [combo 196].

According to a further embodiment the immunological active component of [combo 1] is effective for the treatment and/or prophylaxis of infections caused by the swine pathogens (1), in particular (1a) and/or (1b); (9); and (16) [combo 197], preferably said immunological active component comprises a live modified form, a killed form, or an immunological active part of said swine pathogens (1), in particular (1a) and/or (1b); (9); and (16) [combo 198].

According to a further embodiment the immunological active component of [combo 1] is effective for the treatment and/or prophylaxis of infections caused by the swine pathogens (1), in particular (1a) and/or (1b); (9); and (17) [combo 199], preferably said immunological active component comprises a live modified form, a killed form, or an immunological active part of said swine pathogens (1), in particular (1a) and/or (1b); (9); and (17) [combo 200].

According to a further embodiment the immunological active component of [combo 1] is effective for the treatment and/or prophylaxis of infections caused by the swine pathogens (1), in particular (1a) and/or (1b); (9); and (18) [combo 201], preferably said immunological active component comprises a live modified form, a killed form, or an immunological active part of said swine pathogens (1), in particular (1a) and/or (1b); (9); and (18) [combo 202].

According to a further embodiment the immunological active component of [combo 1] is effective for the treatment and/or prophylaxis of infections caused by the swine pathogens (1), in particular (1a) and/or (1b); (9); and (19) [combo 203], preferably said immunological active component comprises a live modified form, a killed form, or an immunological active part of said swine pathogens (1), in particular (1a) and/or (1b); (9); and (19) [combo 204].

According to a further embodiment the immunological active component of [combo 1] is effective for the treatment and/or prophylaxis of infections caused by the swine pathogens (1), in particular (1a) and/or (1b); (9); and (29), in particular (29a) [combo 205], preferably said immunological active component comprises a live modified form, a killed form, or an immunological active part of said swine pathogens (1), in particular (1a) and/or (1b); (9); and (29), in particular (29a) [combo 206].

According to a further embodiment the immunological active component of [combo 1] is effective for the treatment and/or prophylaxis of infections caused by the swine pathogens (1), in particular (1a) and/or (1b); (10); and (11) [combo 207], preferably said immunological active component comprises a live modified form, a killed form, or an immunological active part of said swine pathogens (1), in particular (1a) and/or (1b); (10); and (11) [combo 208].

According to a further embodiment the immunological active component of [combo 1] is effective for the treatment and/or prophylaxis of infections caused by the swine pathogens (1), in particular (1a) and/or (1b); (10); and (12) [combo 209], preferably said immunological active component comprises a live modified form, a killed form, or an immunological active part of said swine pathogens (1), in particular (1a) and/or (1b); (10); and (12) [combo 210].

According to a further embodiment the immunological active component of [combo 1] is effective for the treatment and/or prophylaxis of infections caused by the swine pathogens (1), in particular (1a) and/or (1b); (10); and (13), in particular (13a) [combo 211], preferably said immunological active component comprises a live modified form, a killed form, or an immunological active part of said swine pathogens (1), in particular (1a) and/or (1b); (10); and (13), in particular (13a) [combo 212].

According to a further embodiment the immunological active component of [combo 1] is effective for the treatment and/or prophylaxis of infections caused by the swine pathogens (1), in particular (1a) and/or (1b); (10); and (14), in particular (14a) and/or (14b) [combo 213], preferably said immunological active component comprises a live modified form, a killed form, or an immunological active part of said swine pathogens (1), in particular (1a) and/or (1b); (10); and (14), in particular (14a) and/or (14b) [combo 214].

According to a further embodiment the immunological active component of [combo 1] is effective for the treatment and/or prophylaxis of infections caused by the swine pathogens (1), in particular (1a) and/or (1b); (10); and (15) [combo 215], preferably said immunological active component comprises a live modified form, a killed form, or an immunological active part of said swine pathogens (1), in particular (1a) and/or (1b); (10); and (15) [combo 216].

According to a further embodiment the immunological active component of [combo 1] is effective for the treatment and/or prophylaxis of infections caused by the swine pathogens (1), in particular (1a) and/or (1b); (10); and (16) [combo 217], preferably said immunological active component comprises a live modified form, a killed form, or an immunological active part of said swine pathogens (1), in particular (1a) and/or (1b); (10); and (16) [combo 218].

According to a further embodiment the immunological active component of [combo 1] is effective for the treatment and/or prophylaxis of infections caused by the swine pathogens (1), in particular (1a) and/or (1b); (10); and (17) [combo 219], preferably said immunological active component comprises a live modified form, a killed form, or an immunological active part of said swine pathogens (1), in particular (1a) and/or (1b); (10); and (17) [combo 220].

According to a further embodiment the immunological active component of [combo 1] is effective for the treatment and/or prophylaxis of infections caused by the swine pathogens (1), in particular (1a) and/or (1b); (10); and (18) [combo 221], preferably said immunological active component comprises a live modified form, a killed form, or an immunological active part of said swine pathogens (1), in particular (1a) and/or (1b); (10); and (18) [combo 222].

According to a further embodiment the immunological active component of [combo 1] is effective for the treatment and/or prophylaxis of infections caused by the swine pathogens (1), in particular (1a) and/or (1b); (10); and (19) [combo 223], preferably said immunological active component comprises a live modified form, a killed form, or an immunological active part of said swine pathogens (1), in particular (1a) and/or (1b); (10); and (19) [combo 224].

According to a further embodiment the immunological active component of [combo 1] is effective for the treatment and/or prophylaxis of infections caused by the swine pathogens (1), in particular (1a) and/or (1b); (10); and (29), in particular (29a) [combo 225], preferably said immunological active component comprises a live modified form, a killed form, or an immunological active part of said swine pathogens (1), in particular (1a) and/or (1b); (10); and (29), in particular (29a) [combo 226].

According to a further embodiment the immunological active component of [combo 1] is effective for the treatment and/or prophylaxis of infections caused by the swine pathogens (1), in particular (1a) and/or (1b); (11); and (12) [combo 227], preferably said immunological active component comprises a live modified form, a killed form, or an immunological active part of said swine pathogens (1), in particular (1a) and/or (1b); (11); and (12) [combo 228].

According to a further embodiment the immunological active component of [combo 1] is effective for the treatment and/or prophylaxis of infections caused by the swine pathogens (1), in particular (1a) and/or (1b); (11); and (13), in particular (13a) [combo 229], preferably said immunological active component comprises a live modified form, a killed form, or an immunological active part of said swine pathogens (1), in particular (1a) and/or (1b); (11); and (13), in particular (13a) [combo 230].

According to a further embodiment the immunological active component of [combo 1] is effective for the treatment and/or prophylaxis of infections caused by the swine pathogens (1), in particular (1a) and/or (1b); (11); and (14), in particular (14a) and/or (14b) [combo 231], preferably said immunological active component comprises a live modified form, a killed form, or an immunological active part of said swine pathogens (1), in particular (1a) and/or (1b); (11); and (14), in particular (14a) and/or (14b) [combo 232].

According to a further embodiment the immunological active component of [combo 1] is effective for the treatment and/or prophylaxis of infections caused by the swine pathogens (1), in particular (1a) and/or (1b); (11); and (15) [combo 233], preferably said immunological active component comprises a live modified form, a killed form, or an immunological active part of said swine pathogen (1), in particular (1a) and/or (1b); (11); and (15) [combo 234].

According to a further embodiment the immunological active component of [combo 1] is effective for the treatment and/or prophylaxis of infections caused by the swine pathogens (1), in particular (1a) and/or (1b); (11); and (16) [combo 235], preferably said immunological active component comprises a live modified form, a killed form, or an immunological active part of said swine pathogens (1), in particular (1a) and/or (1b); (11); and (16) [combo 236].

According to a further embodiment the immunological active component of [combo 1] is effective for the treatment and/or prophylaxis of infections caused by the swine pathogens (1), in particular (1a) and/or (1b); (11); and (17) [combo 237], preferably said immunological active component comprises a live modified form, a killed form, or an immunological active part of said swine pathogens (1), in particular (1a) and/or (1b); (11); and (17) [combo 238].

According to a further embodiment the immunological active component of [combo 1] is effective for the treatment and/or prophylaxis of infections caused by the swine pathogens (1), in particular (1a) and/or (1b); (11); and (18) [combo 239], preferably said immunological active component comprises a live modified form, a killed form, or an immunological active part of said swine pathogens (1), in particular (1a) and/or (1b); (11); and (18) [combo 240].

According to a further embodiment the immunological active component of [combo 1] is effective for the treatment and/or prophylaxis of infections caused by the swine pathogens (1), in particular (1a) and/or (1b); (11); and (19) [combo 241], preferably said immunological active component comprises a live modified form, a killed form, or an immunological active part of said swine pathogens (1), in particular (1a) and/or (1b); (11); and (19) [combo 242].

According to a further embodiment the immunological active component of [combo 1] is effective for the treatment and/or prophylaxis of infections caused by the swine pathogens (1), in particular (1a) and/or (1b); (11); and (29), in particular (29a) [combo 243], preferably said immunological active component comprises a live modified form, a killed form, or an immunological active part of said swine pathogens (1), in particular (1a) and/or (1b); (11); and (29), in particular (29a) [combo 244].

According to a further embodiment the immunological active component of [combo 1] is effective for the treatment and/or prophylaxis of infections caused by the swine pathogens (1), in particular (1a) and/or (1b); (12); and (13), in particular (13a) [combo 245], preferably said immunological active component comprises a live modified form, a killed form, or an immunological active part of said swine pathogens (1), in particular (1a) and/or (1b); (12); and (13), in particular (13a) [combo 246].

According to a further embodiment the immunological active component of [combo 1] is effective for the treatment and/or prophylaxis of infections caused by the swine pathogens (1), in particular (1a) and/or (1b); (12); and (14), in particular (14a) and/or (14b) [combo 247], preferably said immunological active component comprises a live modified form, a killed form, or an immunological active part of said swine pathogens (1), in particular (1a) and/or (1b); (12); and (14), in particular (14a) and/or (14b) [combo 248].

According to a further embodiment the immunological active component of [combo 1] is effective for the treatment and/or prophylaxis of infections caused by the swine pathogens (1), in particular (1a) and/or (1b); (12); and (15) [combo 249], preferably said immunological active component comprises a live modified form, a killed form, or an immunological active part of said swine pathogen (1), in particular (1a) and/or (1b); (12); and (15) [combo 250].

According to a further embodiment the immunological active component of [combo 1] is effective for the treatment and/or prophylaxis of infections caused by the swine pathogens (1), in particular (1a) and/or (1b); (12); and (16) [combo 251], preferably said immunological active component comprises a live modified form, a killed form, or an immunological active part of said swine pathogens (1), in particular (1a) and/or (1b); (12); and (16) [combo 252].

According to a further embodiment the immunological active component of [combo 1] is effective for the treatment and/or prophylaxis of infections caused by the swine pathogens (1), in particular (1a) and/or (1b); (12); and (17) [combo 253], preferably said immunological active component comprises a live modified form, a killed form, or an immunological active part of said swine pathogens (1), in particular (1a) and/or (1b); (12); and (17) [combo 254].

According to a further embodiment the immunological active component of [combo 1] is effective for the treatment and/or prophylaxis of infections caused by the swine pathogens (1), in particular (1a) and/or (1b); (12); and (18) [combo 255], preferably said immunological active component comprises a live modified form, a killed form, or an immunological active part of said swine pathogens (1), in particular (1a) and/or (1b); (12); and (18) [combo 256].

According to a further embodiment the immunological active component of [combo 1] is effective for the treatment and/or prophylaxis of infections caused by the swine pathogens (1), in particular (1a) and/or (1b); (12); and (19) [combo 257], preferably said immunological active component comprises a live modified form, a killed form, or an immunological active part of said swine pathogens (1), in particular (1a) and/or (1b); (12); and (19) [combo 258].

According to a further embodiment the immunological active component of [combo 1] is effective for the treatment and/or prophylaxis of infections caused by the swine pathogens (1), in particular (1a) and/or (1b); (12); and (29), in particular (29a) [combo 259], preferably said immunological active component comprises a live modified form, a killed form, or an immunological active part of said swine pathogens (1), in particular (1a) and/or (1b); (12); and (29), in particular (29a) [combo 260].

According to a further embodiment the immunological active component of [combo 1] is effective for the treatment and/or prophylaxis of infections caused by the swine pathogens (1), in particular (1a) and/or (1b); (13), in particular (13a); and (14), in particular (14a) and/or (14b) [combo 261], preferably said immunological active component comprises a live modified form, a killed form, or an immunological active part of said swine pathogens (1), in particular (1a) and/or (1b); (13), in particular (13a); and (14), in particular (14a) and/or (14b) [combo 262].

According to a further embodiment the immunological active component of [combo 1] is effective for the treatment and/or prophylaxis of infections caused by the swine pathogens (1), in particular (1a) and/or (1b); (13), in particular (13a); and (15) [combo 263], preferably said immunological active component comprises a live modified form, a killed form, or an immunological active part of said swine pathogen (1), in particular (1a) and/or (1b); (13), in particular (13a); and (15) [combo 264].

According to a further embodiment the immunological active component of [combo 1] is effective for the treatment and/or prophylaxis of infections caused by the swine pathogens (1), in particular (1a) and/or (1b); (13), in particular (13a); and (16) [combo 265], preferably said immunological active component comprises a live modified form, a killed form, or an immunological active part of said swine pathogens (1), in particular (1a) and/or (1b); (13), in particular (13a); and (16) [combo 266].

According to a further embodiment the immunological active component of [combo 1] is effective for the treatment and/or prophylaxis of infections caused by the swine pathogens (1), in particular (1a) and/or (1b); (13), in particular (13a); and (17) [combo 267], preferably said immunological active component comprises a live modified form, a killed form, or an immunological active part of said swine pathogens (1), in particular (1a) and/or (1b); (13), in particular (13a); and (17) [combo 268].

According to a further embodiment the immunological active component of [combo 1] is effective for the treatment and/or prophylaxis of infections caused by the swine pathogens (1), in particular (1a) and/or (1b); (13), in particular (13a); and (18) [combo 269], preferably said immunological active component comprises a live modified form, a killed form, or an immunological active part of said swine pathogens (1), in particular (1a) and/or (1b); (13), in particular (13a); and (18) [combo 270].

According to a further embodiment the immunological active component of [combo 1] is effective for the treatment and/or prophylaxis of infections caused by the swine pathogens (1), in particular (1a) and/or (1b); (13), in particular (13a); and (19) [combo 271], preferably said immunological active component comprises a live modified form, a killed form, or an immunological active part of said swine pathogens (1), in particular (1a) and/or (1b); (13), in particular (13a); and (19) [combo 272].

According to a further embodiment the immunological active component of [combo 1] is effective for the treatment and/or prophylaxis of infections caused by the swine pathogens (1), in particular (1a) and/or (1b); (13), in particular (13a); and (29), in particular (29a) [combo 273], preferably said immunological active component comprises a live modified form, a killed form, or an immunological active part of said swine pathogens (1), in particular (1a) and/or (1b); (13), in particular (13a); and (29), in particular (29a) [combo 274].

According to a further embodiment the immunological active component of [combo 1] is effective for the treatment and/or prophylaxis of infections caused by the swine pathogens (1), in particular (1a) and/or (1b); (14), in particular (14a); and (15) [combo 275], preferably said immunological active component comprises a live modified form, a killed form, or an immunological active part of said swine pathogen (1), in particular (1a) and/or (1b); (14), in particular (14a); and (15) [combo 276].

According to a further embodiment the immunological active component of [combo 1] is effective for the treatment and/or prophylaxis of infections caused by the swine pathogens (1), in particular (1a) and/or (1b); (14), in particular (14a); and (16) [combo 277], preferably said immunological active component comprises a live modified form, a killed form, or an immunological active part of said swine pathogens (1), in particular (1a) and/or (1b); (14), in particular (14a); and (16) [combo 278].

According to a further embodiment the immunological active component of [combo 1] is effective for the treatment and/or prophylaxis of infections caused by the swine pathogens (1), in particular (1a) and/or (1b); (14), in particular (14a); and (17) [combo 279], preferably said immunological active component comprises a live modified form, a killed form, or an immunological active part of said swine pathogens (1), in particular (1a) and/or (1b); (14), in particular (14a); and (17) [combo 280].

According to a further embodiment the immunological active component of [combo 1] is effective for the treatment and/or prophylaxis of infections caused by the swine pathogens (1), in particular (1a) and/or (1b); (14), in particular (14a); and (18) [combo 281], preferably said immunological active component comprises a live modified form, a killed form, or an immunological active part of said swine pathogens (1), in particular (1a) and/or (1b); (14), in particular (14a); and (18) [combo 282].

According to a further embodiment the immunological active component of [combo 1] is effective for the treatment and/or prophylaxis of infections caused by the swine pathogens (1), in particular (1a) and/or (1b); (14), in particular (14a); and (19) [combo 283], preferably said immunological active component comprises a live modified form, a killed form, or an immunological active part of said swine pathogens (1), in particular (1a) and/or (1b); (14), in particular (14a); and (19) [combo 284].

According to a further embodiment the immunological active component of [combo 1] is effective for the treatment and/or prophylaxis of infections caused by the swine pathogens (1), in particular (1a) and/or (1b); (14), in particular (14a); and (29), in particular (29a) [combo 285], preferably said immunological active component comprises a live modified form, a killed form, or an immunological active part of said swine pathogens (1), in particular (1a) and/or (1b); (14), in particular (14a); and (29), in particular (29a) [combo 286].

According to a further embodiment the immunological active component of [combo 1] is effective for the treatment and/or prophylaxis of infections caused by the swine pathogens (1), in particular (1a) and/or (1b); (15); and (16) [combo 287], preferably said immunological active component comprises a live modified form, a killed form, or an immunological active part of said swine pathogens (1), in particular (1a) and/or (1b); (15); and (16) [combo 288].

According to a further embodiment the immunological active component of [combo 1] is effective for the treatment and/or prophylaxis of infections caused by the swine pathogens (1), in particular (1a) and/or (1b); (15); and (17) [combo 289], preferably said immunological active component comprises a live modified form, a killed form, or an immunological active part of said swine pathogens (1), in particular (1a) and/or (1b); (15); and (17) [combo 290].

According to a further embodiment the immunological active component of [combo 1] is effective for the treatment and/or prophylaxis of infections caused by the swine pathogens (1), in particular (1a) and/or (1b); (15); and (18) [combo 291], preferably said immunological active component comprises a live modified form, a killed form, or an immunological active part of said swine pathogens (1), in particular (1a) and/or (1b); (15); and (18) [combo 292].

According to a further embodiment the immunological active component of [combo 1] is effective for the treatment and/or prophylaxis of infections caused by the swine pathogens (1), in particular (1a) and/or (1b); (15); and (19) [combo 293], preferably said immunological active component comprises a live modified form, a killed form, or an immunological active part of said swine pathogens (1), in particular (1a) and/or (1b); (15); and (19) [combo 294].

According to a further embodiment the immunological active component of [combo 1] is effective for the treatment and/or prophylaxis of infections caused by the swine pathogens (1), in particular (1a) and/or (1b); (15); and (29), in particular (29a) [combo 295], preferably said immunological active component comprises a live modified form, a killed form, or an immunological active part of said swine pathogens (1), in particular (1a) and/or (1b); (15); and (29), in particular (29a) [combo 296].

According to a further embodiment the immunological active component of [combo 1] is effective for the treatment and/or prophylaxis of infections caused by the swine pathogens (1), in particular (1a) and/or (1b); (16); and (17) [combo 297], preferably said immunological active component comprises a live modified form, a killed form, or an immunological active part of said swine pathogens (1), in particular (1a) and/or (1b); (15); and (17) [combo 298].

According to a further embodiment the immunological active component of [combo 1] is effective for the treatment and/or prophylaxis of infections caused by the swine pathogens (1), in particular (1a) and/or (1b); (16); and (18) [combo 299], preferably said immunological active component comprises a live modified form, a killed form, or an immunological active part of said swine pathogens (1), in particular (1a) and/or (1b); (16); and (18) [combo 300].

According to a further embodiment the immunological active component of [combo 1] is effective for the treatment and/or prophylaxis of infections caused by the swine pathogens (1), in particular (1a) and/or (1b); (16); and (19) [combo 301], preferably said immunological active component comprises a live modified form, a killed form, or an immunological active part of said swine pathogens (1), in particular (1a) and/or (1b); (16); and (19) [combo 302].

According to a further embodiment the immunological active component of [combo 1] is effective for the treatment and/or prophylaxis of infections caused by the swine pathogens (1), in particular (1a) and/or (1b); (16); and (29), in particular (29a) [combo 303], preferably said immunological active component comprises a live modified form, a killed form, or an immunological active part of said swine pathogens (1), in particular (1a) and/or (1b); (16); and (29), in particular (29a) [combo 304].

According to a further embodiment the immunological active component of [combo 1] is effective for the treatment and/or prophylaxis of infections caused by the swine pathogens (1), in particular (1a) and/or (1b); (17); and (18) [combo 305], preferably said immunological active component comprises a live modified form, a killed form, or an immunological active part of said swine pathogens (1), in particular (1a) and/or (1b); (17); and (18) [combo 306].

According to a further embodiment the immunological active component of [combo 1] is effective for the treatment and/or prophylaxis of infections caused by the swine pathogens (1), in particular (1a) and/or (1b); (17); and (19) [combo 307], preferably said immunological active component comprises a live modified form, a killed form, or an immunological active part of said swine pathogens (1), in particular (1a) and/or (1b); (17); and (19) [combo 308].

According to a further embodiment the immunological active component of [combo 1] is effective for the treatment and/or prophylaxis of infections caused by the swine pathogens (1), in particular (1a) and/or (1b); (17); and (29), in particular (29a) [combo 309], preferably said immunological active component comprises a live modified form, a killed form, or an immunological active part of said swine pathogens (1), in particular (1a) and/or (1b); (17); and (29), in particular (29a) [combo 310].

According to a further embodiment the immunological active component of [combo 1] is effective for the treatment and/or prophylaxis of infections caused by the swine pathogens (1), in particular (1a) and/or (1b); (18); and (19) [combo 311], preferably said immunological active component comprises a live modified form, a killed form, or an immunological active part of said swine pathogens (1), in particular (1a) and/or (1b); (18); and (19) [combo 312].

According to a further embodiment the immunological active component of [combo 1] is effective for the treatment and/or prophylaxis of infections caused by the swine pathogens (1), in particular (1a) and/or (1b); (18); and (29), in particular (29a) [combo 313], preferably said immunological active component comprises a live modified form, a killed form, or an immunological active part of said swine pathogens (1), in particular (1a) and/or (1b); (18); and (29), in particular (29a) [combo 314].

According to a further embodiment the immunological active component of [combo 1] is effective for the treatment and/or prophylaxis of infections caused by the swine pathogens (1), in particular (1a) and/or (1b); (19); and (29), in particular (29a) [combo 315], preferably said immunological active component comprises a live modified form, a killed form, or an immunological active part of said swine pathogens (1), in particular (1a) and/or (1b); (19); and (29), in particular (29a) [combo 316].

According to a further embodiment the immunological active component of [combo 1] is effective for the treatment and/or prophylaxis of infections caused by the swine pathogens (9); (10); and (11) [combo 317], preferably said immunological active component comprises a live modified form, a killed form, or an immunological active part of said swine pathogens (9); (10); and (11) [combo 318].

According to a further embodiment the immunological active component of [combo 1] is effective for the treatment and/or prophylaxis of infections caused by the swine pathogens (9); (10); and (12) [combo 319], preferably said immunological active component comprises a live modified form, a killed form, or an immunological active part of said swine pathogens (9); (10); and (12) [combo 320].

According to a further embodiment the immunological active component of [combo 1] is effective for the treatment and/or prophylaxis of infections caused by the swine pathogens (9); (10); and (13), in particular (13a) [combo 321], preferably said immunological active component comprises a live modified form, a killed form, or an immunological active part of said swine pathogens (9); (10); and (13), in particular (13a) [combo 322].

According to a further embodiment the immunological active component of [combo 1] is effective for the treatment and/or prophylaxis of infections caused by the swine pathogens (9); (10); and (14), in particular (14a) and/or (14b) [combo 323], preferably said immunological active component comprises a live modified form, a killed form, or an immunological active part of said swine pathogens (9); (10); and (14), in particular (14a) and/or (14b) [combo 324].

According to a further embodiment the immunological active component of [combo 1] is effective for the treatment and/or prophylaxis of infections caused by the swine pathogens (9); (10); and (15) [combo 325], preferably said immunological active component comprises a live modified form, a killed form, or an immunological active part of said swine pathogens (9); (10); and (15) [combo 326].

According to a further embodiment the immunological active component of [combo 1] is effective for the treatment and/or prophylaxis of infections caused by the swine pathogens (9); (10); and (16) [combo 327], preferably said immunological active component comprises a live modified form, a killed form, or an immunological active part of said swine pathogens (9); (10); and (16) [combo 328].

According to a further embodiment the immunological active component of [combo 1] is effective for the treatment and/or prophylaxis of infections caused by the swine pathogens (9); (10); and (17) [combo 329], preferably said immunological active component comprises a live modified form, a killed form, or an immunological active part of said swine pathogens (9); (10); and (17) [combo 330].

According to a further embodiment the immunological active component of [combo 1] is effective for the treatment and/or prophylaxis of infections caused by the swine pathogens (9); (10); and (18) [combo 331], preferably said immunological active component comprises a live modified form, a killed form, or an immunological active part of said swine pathogens (9); (10); and (18) [combo 332].

According to a further embodiment the immunological active component of [combo 1] is effective for the treatment and/or prophylaxis of infections caused by the swine pathogens (9); (10); and (19) [combo 333], preferably said immunological active component comprises a live modified form, a killed form, or an immunological active part of said swine pathogens (9); (10); and (19) [combo 334].

According to a further embodiment the immunological active component of [combo 1] is effective for the treatment and/or prophylaxis of infections caused by the swine pathogens (9); (10); and (29), in particular (29a) [combo 335], preferably said immunological active component comprises a live modified form, a killed form, or an immunological active part of said swine pathogens (9); (10); and (29), in particular (29a) [combo 336].

According to a further embodiment the immunological active component of [combo 1] is effective for the treatment and/or prophylaxis of infections caused by the swine pathogens (9); (11); and (12) [combo 337], preferably said immunological active component comprises a live modified form, a killed form, or an immunological active part of said swine pathogens (9); (11); and (12) [combo 338].

According to a further embodiment the immunological active component of [combo 1] is effective for the treatment and/or prophylaxis of infections caused by the swine pathogens (1), in particular (1a) and/or (1b); (11); and (13), in particular (13a) [combo 339], preferably said immunological active component comprises a live modified form, a killed form, or an immunological active part of said swine pathogens (9); (11); and (13), in particular (13a) [combo 340].

According to a further embodiment the immunological active component of [combo 1] is effective for the treatment and/or prophylaxis of infections caused by the swine pathogens (9); (11); and (14), in particular (14a) and/or (14b) [combo 341], preferably said immunological active component comprises a live modified form, a killed form, or an immunological active part of said swine pathogens (9); (11); and (14), in particular (14a) and/or (14b) [combo 342].

According to a further embodiment the immunological active component of [combo 1] is effective for the treatment and/or prophylaxis of infections caused by the swine pathogens (9); (11); and (15) [combo 343], preferably said immunological active component comprises a live modified form, a killed form, or an immunological active part of said swine pathogen (9); (11); and (15) [combo 344].

According to a further embodiment the immunological active component of [combo 1] is effective for the treatment and/or prophylaxis of infections caused by the swine pathogens (9); (11); and (16) [combo 345], preferably said immunological active component comprises a live modified form, a killed form, or an immunological active part of said swine pathogens (9); (11); and (16) [combo 346].

According to a further embodiment the immunological active component of [combo 1] is effective for the treatment and/or prophylaxis of infections caused by the swine pathogens (9); (11); and (17) [combo 347], preferably said immunological active component comprises a live modified form, a killed form, or an immunological active part of said swine pathogens (9); (11); and (17) [combo 348].

According to a further embodiment the immunological active component of [combo 1] is effective for the treatment and/or prophylaxis of infections caused by the swine pathogens (9); (11); and (18) [combo 349], preferably said immunological active component comprises a live modified form, a killed form, or an immunological active part of said swine pathogens (9); (11); and (18) [combo 350].

According to a further embodiment the immunological active component of [combo 1] is effective for the treatment and/or prophylaxis of infections caused by the swine pathogens (9); (11); and (19) [combo 351], preferably said immunological active component comprises a live modified form, a killed form, or an immunological active part of said swine pathogens (9); (11); and (19) [combo 352].

According to a further embodiment the immunological active component of [combo 1] is effective for the treatment and/or prophylaxis of infections caused by the swine pathogens (9); (11); and (29), in particular (29a) [combo 353], preferably said immunological active component comprises a live modified form, a killed form, or an immunological active part of said swine pathogens (9); (11); and (29), in particular (29a) [combo 354].

According to a further embodiment the immunological active component of [combo 1] is effective for the treatment and/or prophylaxis of infections caused by the swine pathogens (9); (12); and (13), in particular (13a) [combo 355], preferably said immunological active component comprises a live modified form, a killed form, or an immunological active part of said swine pathogens (9); (12); and (13), in particular (13a) [combo 356].

According to a further embodiment the immunological active component of [combo 1] is effective for the treatment and/or prophylaxis of infections caused by the swine pathogens (9); (12); and (14), in particular (14a) and/or (14b) [combo 357], preferably said immunological active component comprises a live modified form, a killed form, or an immunological active part of said swine pathogens (9); (12); and (14), in particular (14a) and/or (14b) [combo 358].

According to a further embodiment the immunological active component of [combo 1] is effective for the treatment and/or prophylaxis of infections caused by the swine pathogens (9); (12); and (15) [combo 359], preferably said immunological active component comprises a live modified form, a killed form, or an immunological active part of said swine pathogen (9); (12); and (15) [combo 360].

According to a further embodiment the immunological active component of [combo 1] is effective for the treatment and/or prophylaxis of infections caused by the swine pathogens (9); (12); and (16) [combo 361], preferably said immunological active component comprises a live modified form, a killed form, or an immunological active part of said swine pathogens (9); (12); and (16) [combo 362].

According to a further embodiment the immunological active component of [combo 1] is effective for the treatment and/or prophylaxis of infections caused by the swine pathogens (9); (12); and (17) [combo 363], preferably said immunological active component comprises a live modified form, a killed form, or an immunological active part of said swine pathogens (9); (12); and (17) [combo 364].

According to a further embodiment the immunological active component of [combo 1] is effective for the treatment and/or prophylaxis of infections caused by the swine pathogens (9); (12); and (18) [combo 365], preferably said immunological active component comprises a live modified form, a killed form, or an immunological active part of said swine pathogens (9); (12); and (18) [combo 366].

According to a further embodiment the immunological active component of [combo 1] is effective for the treatment and/or prophylaxis of infections caused by the swine pathogens (9); (12); and (19) [combo 367], preferably said immunological active component comprises a live modified form, a killed form, or an immunological active part of said swine pathogens (9); (12); and (19) [combo 368].

According to a further embodiment the immunological active component of [combo 1] is effective for the treatment and/or prophylaxis of infections caused by the swine pathogens (9); (12); and (29), in particular (29a) [combo 369], preferably said immunological active component comprises a live modified form, a killed form, or an immunological active part of said swine pathogens (9); (12); and (29), in particular (29a) [combo 370].

According to a further embodiment the immunological active component of [combo 1] is effective for the treatment and/or prophylaxis of infections caused by the swine pathogens (9); (13), in particular (13a); and (14), in particular (14a) and/or (14b) [combo 371], preferably said immunological active component comprises a live modified form, a killed form, or an immunological active part of said swine pathogens (9); (13), in particular (13a); and (14), in particular (14a) and/or (14b) [combo 372].

According to a further embodiment the immunological active component of [combo 1] is effective for the treatment and/or prophylaxis of infections caused by the swine pathogens (9), (13), in particular (13a); and (15) [combo 373], preferably said immunological active component comprises a live modified form, a killed form, or an immunological active part of said swine pathogen (9); (13), in particular (13a); and (15) [combo 374].

According to a further embodiment the immunological active component of [combo 1] is effective for the treatment and/or prophylaxis of infections caused by the swine pathogens (9); (13), in particular (13a); and (16) [combo 375], preferably said immunological active component comprises a live modified form, a killed form, or an immunological active part of said swine pathogens (9); (13), in particular (13a); and (16) [combo 376].

According to a further embodiment the immunological active component of [combo 1] is effective for the treatment and/or prophylaxis of infections caused by the swine pathogens (9); (13), in particular (13a); and (17) [combo 377], preferably said immunological active component comprises a live modified form, a killed form, or an immunological active part of said swine pathogens (9); (13), in particular (13a); and (17) [combo 378].

According to a further embodiment the immunological active component of [combo 1] is effective for the treatment and/or prophylaxis of infections caused by the swine pathogens (9); (13), in particular (13a); and (18) [combo 379], preferably said immunological active component comprises a live modified form, a killed form, or an immunological active part of said swine pathogens (9); (13), in particular (13a); and (18) [combo 380].

According to a further embodiment the immunological active component of [combo 1] is effective for the treatment and/or prophylaxis of infections caused by the swine pathogens (9); (13), in particular (13a); and (19) [combo 381], preferably said immunological active component comprises a live modified form, a killed form, or an immunological active part of said swine pathogens (9); (13), in particular (13a); and (19) [combo 382].

According to a further embodiment the immunological active component of [combo 1] is effective for the treatment and/or prophylaxis of infections caused by the swine pathogens (9); (13), in particular (13a); and (29), in particular (29a) [combo 383], preferably said immunological active component comprises a live modified form, a killed form, or an immunological active part of said swine pathogens (9), in particular (13a); and (29), in particular (29a) [combo 384].

According to a further embodiment the immunological active component of [combo 1] is effective for the treatment and/or prophylaxis of infections caused by the swine pathogens (9); (14), in particular (14a); and (15) [combo 385], preferably said immunological active component comprises a live modified form, a killed form, or an immunological active part of said swine pathogen (9); (14), in particular (14a); and (15) [combo 386].

According to a further embodiment the immunological active component of [combo 1] is effective for the treatment and/or prophylaxis of infections caused by the swine pathogens (9); (14), in particular (14a); and (16) [combo 387], preferably said immunological active component comprises a live modified form, a killed form, or an immunological active part of said swine pathogens (9); (14), in particular (14a); and (16) [combo 388].

According to a further embodiment the immunological active component of [combo 1] is effective for the treatment and/or prophylaxis of infections caused by the swine pathogens (9); (14), in particular (14a); and (17) [combo 389], preferably said immunological active component comprises a live modified form, a killed form, or an immunological active part of said swine pathogens (9); (14), in particular (14a); and (17) [combo 390].

According to a further embodiment the immunological active component of [combo 1] is effective for the treatment and/or prophylaxis of infections caused by the swine pathogens (9); (14), in particular (14a); and (18) [combo 391], preferably said immunological active component comprises a live modified form, a killed form, or an immunological active part of said swine pathogens (9); (14), in particular (14a); and (18) [combo 392].

According to a further embodiment the immunological active component of [combo 1] is effective for the treatment and/or prophylaxis of infections caused by the swine pathogens (9); (14), in particular (14a); and (19) [combo 393], preferably said immunological active component comprises a live modified form, a killed form, or an immunological active part of said swine pathogens (9); (14), in particular (14a); and (19) [combo 394].

According to a further embodiment the immunological active component of [combo 1] is effective for the treatment and/or prophylaxis of infections caused by the swine pathogens (9); (14), in particular (14a); and (29), in particular (29a) [combo 395], preferably said immunological active component comprises a live modified form, a killed form, or an immunological active part of said swine pathogens (9); (14), in particular (14a); and (29), in particular (29a) [combo 396].

According to a further embodiment the immunological active component of [combo 1] is effective for the treatment and/or prophylaxis of infections caused by the swine pathogens (9); (15); and (16) [combo 397], preferably said immunological active component comprises a live modified form, a killed form, or an immunological active part of said swine pathogens (9); (15); and (16) [combo 398].

According to a further embodiment the immunological active component of [combo 1] is effective for the treatment and/or prophylaxis of infections caused by the swine pathogens (9); (15); and (17) [combo 399], preferably said immunological active component comprises a live modified form, a killed form, or an immunological active part of said swine pathogens (9); (15); and (17) [combo 400].

According to a further embodiment the immunological active component of [combo 1] is effective for the treatment and/or prophylaxis of infections caused by the swine pathogens (9); (15); and (18) [combo 401], preferably said immunological active component comprises a live modified form, a killed form, or an immunological active part of said swine pathogens (9); (1 5); and (18) [combo 402].

According to a further embodiment the immunological active component of [combo 1] is effective for the treatment and/or prophylaxis of infections caused by the swine pathogens (9); (15); and (19) [combo 403], preferably said immunological active component comprises a live modified form, a killed form, or an immunological active part of said swine pathogens (9); (15); and (19) [combo 404].

According to a further embodiment the immunological active component of [combo 1] is effective for the treatment and/or prophylaxis of infections caused by the swine pathogens (9); (15); and (29), in particular (29a) [combo 405], preferably said immunological active component comprises a live modified form, a killed form, or an immunological active part of said swine pathogens (9); (15); and (29), in particular (29a) [combo 406].

According to a further embodiment the immunological active component of [combo 1] is effective for the treatment and/or prophylaxis of infections caused by the swine pathogens (9); (16); and (17) [combo 407], preferably said immunological active component comprises a live modified form, a killed form, or an immunological active part of said swine pathogens (9); (15); and (17) [combo 408].

According to a further embodiment the immunological active component of [combo 1] is effective for the treatment and/or prophylaxis of infections caused by the swine pathogens (9); (16); and (18) [combo 409], preferably said immunological active component comprises a live modified form, a killed form, or an immunological active part of said swine pathogens (9); (16); and (18) [combo 410].

According to a further embodiment the immunological active component of [combo 1] is effective for the treatment and/or prophylaxis of infections caused by the swine pathogens (9); (16); and (19) [combo 411], preferably said immunological active component comprises a live modified form, a killed form, or an immunological active part of said swine pathogens (9); (16); and (19) [combo 412].

According to a further embodiment the immunological active component of [combo 1] is effective for the treatment and/or prophylaxis of infections caused by the swine pathogens (9); (16); and (29), in particular (29a) [combo 413], preferably said immunological active component comprises a live modified form, a killed form, or an immunological active part of said swine pathogens (9); (16); and (29), in particular (29a) [combo 412].

According to a further embodiment the immunological active component of [combo 1] is effective for the treatment and/or prophylaxis of infections caused by the swine pathogens (9); (17); and (18) [combo 413], preferably said immunological active component comprises a live modified form, a killed form, or an immunological active part of said swine pathogens (9); (17); and (18) [combo 414].

According to a further embodiment the immunological active component of [combo 1] is effective for the treatment and/or prophylaxis of infections caused by the swine pathogens (9); (17); and (19) [combo 415], preferably said immunological active component comprises a live modified form, a killed form, or an immunological active part of said swine pathogens (9); (17); and (19) [combo 416].

According to a further embodiment the immunological active component of [combo 1] is effective for the treatment and/or prophylaxis of infections caused by the swine pathogens (9); (17); and (29), in particular (29a) [combo 417], preferably said immunological active component comprises a live modified form, a killed form, or an immunological active part of said swine pathogens (9); (17); and (29), in particular (29a) [combo 418].

According to a further embodiment the immunological active component of [combo 1] is effective for the treatment and/or prophylaxis of infections caused by the swine pathogens (9); (18); and (19) [combo 419], preferably said immunological active component comprises a live modified form, a killed form, or an immunological active part of said swine pathogens (9); (18); and (19) [combo 420].

According to a further embodiment the immunological active component of [combo 1] is effective for the treatment and/or prophylaxis of infections caused by the swine pathogens (9); (18); and (29), in particular (29a) [combo 421], preferably said immunological active component comprises a live modified form, a killed form, or an immunological active part of said swine pathogens (9); (18); and (29), in particular (29a) [combo 422].

According to a further embodiment the immunological active component of [combo 1] is effective for the treatment and/or prophylaxis of infections caused by the swine pathogens (9); (19); and (29), in particular (29a) [combo 423], preferably said immunological active component comprises a live modified form, a killed form, or an immunological active part of said swine pathogens (9); (19); and (29), in particular (29a) [combo 424].

According to a further embodiment the immunological active component of [combo 1] is effective for the treatment and/or prophylaxis of infections caused by the swine pathogens (11); (10); and (12) [combo 425], preferably said immunological active component comprises a live modified form, a killed form, or an immunological active part of said swine pathogens (11); (10); and (12) [combo 426].

According to a further embodiment the immunological active component of [combo 1] is effective for the treatment and/or prophylaxis of infections caused by the swine pathogens (11); (10); and (13), in particular (13a) [combo 427], preferably said immunological active component comprises a live modified form, a killed form, or an immunological active part of said swine pathogens (11); (10); and (13), in particular (13a) [combo 428].

According to a further embodiment the immunological active component of [combo 1] is effective for the treatment and/or prophylaxis of infections caused by the swine pathogens (11); (10); and (14), in particular (14a) and/or (14b) [combo 429], preferably said immunological active component comprises a live modified form, a killed form, or an immunological active part of said swine pathogens (11); (10); and (14), in particular (14a) and/or (14b) [combo 430].

According to a further embodiment the immunological active component of [combo 1] is effective for the treatment and/or prophylaxis of infections caused by the swine pathogens (11); (10); and (15) [combo 431], preferably said immunological active component comprises a live modified form, a killed form, or an immunological active part of said swine pathogens (11); (10); and (15) [combo 432].

According to a further embodiment the immunological active component of [combo 1] is effective for the treatment and/or prophylaxis of infections caused by the swine pathogens (11); (10); and (16) [combo 433], preferably said immunological active component comprises a live modified form, a killed form, or an immunological active part of said swine pathogens (11); (10); and (16) [combo 434].

According to a further embodiment the immunological active component of [combo 1] is effective for the treatment and/or prophylaxis of infections caused by the swine pathogens (11); (10); and (17) [combo 435], preferably said immunological active component comprises a live modified form, a killed form, or an immunological active part of said swine pathogens (11); (10); and (17) [combo 436].

According to a further embodiment the immunological active component of [combo 1] is effective for the treatment and/or prophylaxis of infections caused by the swine pathogens (11); (10); and (18) [combo 437], preferably said immunological active component comprises a live modified form, a killed form, or an immunological active part of said swine pathogens (11); (10); and (18) [combo 438].

According to a further embodiment the immunological active component of [combo 1] is effective for the treatment and/or prophylaxis of infections caused by the swine pathogens (11); (10); and (19) [combo 439], preferably said immunological active component comprises a live modified form, a killed form, or an immunological active part of said swine pathogens (11); (10); and (19) [combo 440].

According to a further embodiment the immunological active component of [combo 1] is effective for the treatment and/or prophylaxis of infections caused by the swine pathogens (11); (10); and (29), in particular (29a) [combo 441], preferably said immunological active component comprises a live modified form, a killed form, or an immunological active part of said swine pathogens (11); (10); and (29), in particular (29a) [combo 442].

According to a further embodiment the immunological active component of [combo 1] is effective for the treatment and/or prophylaxis of infections caused by the swine pathogens (11); (12); and (13), in particular (13a) [combo 443], preferably said immunological active component comprises a live modified form, a killed form, or an immunological active part of said swine pathogens (11); (12); and (13), in particular (13a) [combo 444].

According to a further embodiment the immunological active component of [combo 1] is effective for the treatment and/or prophylaxis of infections caused by the swine pathogens (11); (12); and (14), in particular (14a) and/or (14b) [combo 445], preferably said immunological active component comprises a live modified form, a killed form, or an immunological active part of said swine pathogens (11); (12); and (14), in particular (14a) and/or (14b) [combo 446].

According to a further embodiment the immunological active component of [combo 1] is effective for the treatment and/or prophylaxis of infections caused by the swine pathogens (11); (12); and (15) [combo 447], preferably said immunological active component comprises a live modified form, a killed form, or an immunological active part of said swine pathogen (11); (12); and (15) [combo 448].

According to a further embodiment the immunological active component of [combo 1] is effective for the treatment and/or prophylaxis of infections caused by the swine pathogens (11); (12); and (16) [combo 449], preferably said immunological active component comprises a live modified form, a killed form, or an immunological active part of said swine pathogens (11); (12); and (16) [combo 450].

According to a further embodiment the immunological active component of [combo 1] is effective for the treatment and/or prophylaxis of infections caused by the swine pathogens (11); (12); and (17) [combo 451], preferably said immunological active component comprises a live modified form, a killed form, or an immunological active part of said swine pathogens (11); (12); and (17) [combo 452].

According to a further embodiment the immunological active component of [combo 1] is effective for the treatment and/or prophylaxis of infections caused by the swine pathogens (11); (12); and (18) [combo 453], preferably said immunological active component comprises a live modified form, a killed form, or an immunological active part of said swine pathogens (11); (12); and (18) [combo 454].

According to a further embodiment the immunological active component of [combo 1] is effective for the treatment and/or prophylaxis of infections caused by the swine pathogens (11); (12); and (19) [combo 455], preferably said immunological active component comprises a live modified form, a killed form, or an immunological active part of said swine pathogens (11); (12); and (19) [combo 456].

According to a further embodiment the immunological active component of [combo 1] is effective for the treatment and/or prophylaxis of infections caused by the swine pathogens (11); (12); and (29), in particular (29a) [combo 457], preferably said immunological active component comprises a live modified form, a killed form, or an immunological active part of said swine pathogens (11); (12); and (29), in particular (29a) [combo 458].

According to a further embodiment the immunological active component of [combo 1] is effective for the treatment and/or prophylaxis of infections caused by the swine pathogens (11); (13), in particular (13a); and (14), in particular (14a) and/or (14b) [combo 459], preferably said immunological active component comprises a live modified form, a killed form, or an immunological active part of said swine pathogens (11); (13), in particular (13a); and (14), in particular (14a) and/or (14b) [combo 460].

According to a further embodiment the immunological active component of [combo 1] is effective for the treatment and/or prophylaxis of infections caused by the swine pathogens (11), (13), in particular (13a); and (15) [combo 461], preferably said immunological active component comprises a live modified form, a killed form, or an immunological active part of said swine pathogen (11); (13), in particular (13a); and (15) [combo 462].

According to a further embodiment the immunological active component of [combo 1] is effective for the treatment and/or prophylaxis of infections caused by the swine pathogens (11); (13), in particular (13a); and (16) [combo 463], preferably said immunological active component comprises a live modified form, a killed form, or an immunological active part of said swine pathogens (11); (13), in particular (13a); and (16) [combo 464].

According to a further embodiment the immunological active component of [combo 1] is effective for the treatment and/or prophylaxis of infections caused by the swine pathogens (11); (13), in particular (13a); and (17) [combo 465], preferably said immunological active component comprises a live modified form, a killed form, or an immunological active part of said swine pathogens (11); (13), in particular (13a); and (17) [combo 466].

According to a further embodiment the immunological active component of [combo 1] is effective for the treatment and/or prophylaxis of infections caused by the swine pathogens (11); (13), in particular (13a); and (18) [combo 467], preferably said immunological active component comprises a live modified form, a killed form, or an immunological active part of said swine pathogens (11); (13), in particular (13a); and (18) [combo 468].

According to a further embodiment the immunological active component of [combo 1] is effective for the treatment and/or prophylaxis of infections caused by the swine pathogens (11); (13), in particular (13a); and (19) [combo 469], preferably said immunological active component comprises a live modified form, a killed form, or an immunological active part of said swine pathogens (11); (13), in particular (13a); and (19) [combo 470].

According to a further embodiment the immunological active component of [combo 1] is effective for the treatment and/or prophylaxis of infections caused by the swine pathogens (11); (13), in particular (13a); and (29), in particular (29a) [combo 471], preferably said immunological active component comprises a live modified form, a killed form, or an immunological active part of said swine pathogens (11), in particular (13a); and (29), in particular (29a) [combo 472].

According to a further embodiment the immunological active component of [combo 1] is effective for the treatment and/or prophylaxis of infections caused by the swine pathogens (11); (14), in particular (14a); and (15) [combo 473], preferably said immunological active component comprises a live modified form, a killed form, or an immunological active part of said swine pathogen (11); (14), in particular (14a); and (15) [combo 474].

According to a further embodiment the immunological active component of [combo 1] is effective for the treatment and/or prophylaxis of infections caused by the swine pathogens (11); (14), in particular (14a); and (16) [combo 475], preferably said immunological active component comprises a live modified form, a killed form, or an immunological active part of said swine pathogens (11); (14), in particular (14a); and (16) [combo 476].

According to a further embodiment the immunological active component of [combo 1] is effective for the treatment and/or prophylaxis of infections caused by the swine pathogens (11); (14), in particular (14a); and (17) [combo 477], preferably said immunological active component comprises a live modified form, a killed form, or an immunological active part of said swine pathogens (11); (14), in particular (14a); and (17) [combo 478].

According to a further embodiment the immunological active component of [combo 1] is effective for the treatment and/or prophylaxis of infections caused by the swine pathogens (11); (14), in particular (14a); and (18) [combo 479], preferably said immunological active component comprises a live modified form, a killed form, or an immunological active part of said swine pathogens (11); (14), in particular (14a); and (18) [combo 480].

According to a further embodiment the immunological active component of [combo 1] is effective for the treatment and/or prophylaxis of infections caused by the swine pathogens (11); (14), in particular (14a); and (19) [combo 481], preferably said lo immunological active component comprises a live modified form, a killed form, or an immunological active part of said swine pathogens (11); (14), in particular (14a); and (19) [combo 482].

According to a further embodiment the immunological active component of [combo 1] is effective for the treatment and/or prophylaxis of infections caused by the swine pathogens (11); (14), in particular (14a); and (29), in particular (29a) [combo 483], preferably said immunological active component comprises a live modified form, a killed form, or an immunological active part of said swine pathogens (11); (14), in particular (14a); and (29), in particular (29a) [combo 484].

According to a further embodiment the immunological active component of [combo 1] is effective for the treatment and/or prophylaxis of infections caused by the swine pathogens (11); (15); and (16) [combo 485], preferably said immunological active component comprises a live modified form, a killed form, or an immunological active part of said swine pathogens (11); (15); and (16) [combo 486].

According to a further embodiment the immunological active component of [combo 1] is effective for the treatment and/or prophylaxis of infections caused by the swine pathogens (11); (15); and (17) [combo 487], preferably said immunological active component comprises a live modified form, a killed form, or an immunological active part of said swine pathogens (11); (15); and (17) [combo 488].

According to a further embodiment the immunological active component of [combo 1] is effective for the treatment and/or prophylaxis of infections caused by the swine pathogens (11); (15); and (18) [combo 489], preferably said immunological active component comprises a live modified form, a killed form, or an immunological active part of said swine pathogens (11); (15); and (18) [combo 490].

According to a further embodiment the immunological active component of [combo 1] is effective for the treatment and/or prophylaxis of infections caused by the swine pathogens (11); (15); and (19) [combo 491], preferably said immunological active component comprises a live modified form, a killed form, or an immunological active part of said swine pathogens (11); (15); and (19) [combo 492].

According to a further embodiment the immunological active component of [combo 1] is effective for the treatment and/or prophylaxis of infections caused by the swine pathogens (11); (15); and (29), in particular (29a) [combo 493], preferably said immunological active component comprises a live modified form, a killed form, or an immunological active part of said swine pathogens (11); (15); and (29), in particular (29a) [combo 494].

According to a further embodiment the immunological active component of [combo 1] is effective for the treatment and/or prophylaxis of infections caused by the swine pathogens (11); (16); and (17) [combo 495], preferably said immunological active component comprises a live modified form, a killed form, or an immunological active part of said swine pathogens (11); (15); and (17) [combo 496].

According to a further embodiment the immunological active component of [combo 1] is effective for the treatment and/or prophylaxis of infections caused by the swine pathogens (11); (16); and (18) [combo 497], preferably said immunological active component comprises a live modified form, a killed form, or an immunological active part of said swine pathogens (11); (16); and (18) [combo 498].

According to a further embodiment the immunological active component of [combo 1] is effective for the treatment and/or prophylaxis of infections caused by the swine pathogens (11); (16); and (19) [combo 499], preferably said immunological active component comprises a live modified form, a killed form, or an immunological active part of said swine pathogens (11); (16); and (19) [combo 500].

According to a further embodiment the immunological active component of [combo 1] is effective for the treatment and/or prophylaxis of infections caused by the swine pathogens (11); (16); and (29), in particular (29a) [combo 501], preferably said immunological active component comprises a live modified form, a killed form, or an immunological active part of said swine pathogens (11); (16); and (29), in particular (29a) [combo 502].

According to a further embodiment the immunological active component of [combo 1] is effective for the treatment and/or prophylaxis of infections caused by the swine pathogens (11); (17); and (18) [combo 503], preferably said immunological active component comprises a live modified form, a killed form, or an immunological active part of said swine pathogens (11); (17); and (18) [combo 504].

According to a further embodiment the immunological active component of [combo 1] is effective for the treatment and/or prophylaxis of infections caused by the swine pathogens (11); (17); and (19) [combo 505], preferably said immunological active component comprises a live modified form, a killed form, or an immunological active part of said swine pathogens (11); (17); and (19) [combo 506].

According to a further embodiment the immunological active component of [combo 1] is effective for the treatment and/or prophylaxis of infections caused by the swine pathogens (11); (17); and (29), in particular (29a) [combo 507], preferably said immunological active component comprises a live modified form, a killed form, or an immunological active part of said swine pathogens (11); (17); and (29), in particular (29a) [combo 508].

According to a further embodiment the immunological active component of [combo 1] is effective for the treatment and/or prophylaxis of infections caused by the swine pathogens (11); (18); and (19) [combo 509], preferably said immunological active component comprises a live modified form, a killed form, or an immunological active part of said swine pathogens (11); (18); and (19) [combo 510].

According to a further embodiment the immunological active component of [combo 1] is effective for the treatment and/or prophylaxis of infections caused by the swine pathogens (11); (18); and (29), in particular (29a) [combo 511], preferably said immunological active component comprises a live modified form, a killed form, or an immunological active part of said swine pathogens (11); (18); and (29), in particular (29a) [combo 512].

According to a further embodiment the immunological active component of [combo 1] is effective for the treatment and/or prophylaxis of infections caused by the swine pathogens (11); (19); and (29), in particular (29a) [combo 513], preferably said immunological active component comprises a live modified form, a killed form, or an immunological active part of said swine pathogens (11); (19); and (29), in particular (29a) [combo 514].

According to a further embodiment the immunological active component of [combo 1] is effective for the treatment and/or prophylaxis of infections caused by the swine pathogens (12); (10); and (13), in particular (13a) [combo 515], preferably said immunological active component comprises a live modified form, a killed form, or an immunological active part of said swine pathogens (12); (10); and (13), in particular (13a) [combo 516].

According to a further embodiment the immunological active component of [combo 1] is effective for the treatment and/or prophylaxis of infections caused by the swine pathogens (12); (10); and (14), in particular (14a) and/or (14b) [combo 517], preferably said immunological active component comprises a live modified form, a killed form, or an immunological active part of said swine pathogens (12); (10); and (14), in particular (14a) and/or (14b) [combo 518].

According to a further embodiment the immunological active component of [combo 1] is effective for the treatment and/or prophylaxis of infections caused by the swine pathogens (12); (10); and (15) [combo 519], preferably said immunological active component comprises a live modified form, a killed form, or an immunological active part of said swine pathogens (12); (10); and (15) [combo 520].

According to a further embodiment the immunological active component of [combo 1] is effective for the treatment and/or prophylaxis of infections caused by the swine pathogens (12); (10); and (16) [combo 521], preferably said immunological active component comprises a live modified form, a killed form, or an immunological active part of said swine pathogens (12); (10); and (16) [combo 522].

According to a further embodiment the immunological active component of [combo 1] is effective for the treatment and/or prophylaxis of infections caused by the swine pathogens (12); (10); and (17) [combo 523], preferably said immunological active component comprises a live modified form, a killed form, or an immunological active part of said swine pathogens (12); (10); and (17) [combo 524].

According to a further embodiment the immunological active component of [combo 1] is effective for the treatment and/or prophylaxis of infections caused by the swine pathogens (12); (10); and (18) [combo 525], preferably said immunological active component comprises a live modified form, a killed form, or an immunological active part of said swine pathogens (12); (10); and (18) [combo 526].

According to a further embodiment the immunological active component of [combo 1] is effective for the treatment and/or prophylaxis of infections caused by the swine pathogens (12); (10); and (19) [combo 527], preferably said immunological active component comprises a live modified form, a killed form, or an immunological active part of said swine pathogens (12); (10); and (19) [combo 528].

According to a further embodiment the immunological active component of [combo 1] is effective for the treatment and/or prophylaxis of infections caused by the swine pathogens (12); (10); and (29), in particular (29a) [combo 529], preferably said immunological active component comprises a live modified form, a killed form, or an immunological active part of said swine pathogens (12); (10); and (29), in particular (29a) [combo 530].

According to a further embodiment the immunological active component of [combo 1] is effective for the treatment and/or prophylaxis of infections caused by the swine pathogens (12); (13), in particular (13a); and (14), in particular (14a) and/or (14b) [combo 531], preferably said immunological active component comprises a live modified form, a killed form, or an immunological active part of said swine pathogens (12); (13), in particular (13a); and (14), in particular (14a) and/or (14b) [combo 532].

According to a further embodiment the immunological active component of [combo 1] is effective for the treatment and/or prophylaxis of infections caused by the swine pathogens (12), (13), in particular (13a); and (15) [combo 533], preferably said immunological active component comprises a live modified form, a killed form, or an immunological active part of said swine pathogen (12); (13), in particular (13a); and (15) [combo 534].

According to a further embodiment the immunological active component of [combo 1] is effective for the treatment and/or prophylaxis of infections caused by the swine pathogens (12); (13), in particular (13a); and (16) [combo 535], preferably said immunological active component comprises a live modified form, a killed form, or an immunological active part of said swine pathogens (12); (13), in particular (13a); and (16) [combo 536].

According to a further embodiment the immunological active component of [combo 1] is effective for the treatment and/or prophylaxis of infections caused by the swine pathogens (12); (13), in particular (13a); and (17) [combo 537], preferably said immunological active component comprises a live modified form, a killed form, or an immunological active part of said swine pathogens (12); (13), in particular (13a); and (17) [combo 538].

According to a further embodiment the immunological active component of [combo 1] is effective for the treatment and/or prophylaxis of infections caused by the swine pathogens (12); (13), in particular (13a); and (18) [combo 539], preferably said immunological active component comprises a live modified form, a killed form, or an immunological active part of said swine pathogens (12); (13), in particular (13a); and (18) [combo 540].

According to a further embodiment the immunological active component of [combo 1] is effective for the treatment and/or prophylaxis of infections caused by the swine pathogens (12); (13), in particular (13a); and (19) [combo 541], preferably said immunological active component comprises a live modified form, a killed form, or an immunological active part of said swine pathogens (12); (13), in particular (13a); and (19) [combo 542].

According to a further embodiment the immunological active component of [combo 1] is effective for the treatment and/or prophylaxis of infections caused by the swine pathogens (12); (13), in particular (13a); and (29), in particular (29a) [combo 543], preferably said immunological active component comprises a live modified form, a killed form, or an immunological active part of said swine pathogens (12), in particular (13a); and (29), in particular (29a) [combo 544].

According to a further embodiment the immunological active component of [combo 1] is effective for the treatment and/or prophylaxis of infections caused by the swine pathogens (12); (14), in particular (14a); and (15) [combo 545], preferably said immunological active component comprises a live modified form, a killed form, or an immunological active part of said swine pathogen (12); (14), in particular (14a); and (15) [combo 546].

According to a further embodiment the immunological active component of [combo 1] is effective for the treatment and/or prophylaxis of infections caused by the swine pathogens (12); (14), in particular (14a); and (16) [combo 547], preferably said immunological active component comprises a live modified form, a killed form, or an immunological active part of said swine pathogens (12); (14), in particular (14a); and (16) [combo 548].

According to a further embodiment the immunological active component of [combo 1] is effective for the treatment and/or prophylaxis of infections caused by the swine pathogens (12); (14), in particular (14a); and (17) [combo 549], preferably said immunological active component comprises a live modified form, a killed form, or an immunological active part of said swine pathogens (12); (14), in particular (14a); and (17) [combo 550].

According to a further embodiment the immunological active component of [combo 1] is effective for the treatment and/or prophylaxis of infections caused by the swine pathogens (12); (14), in particular (14a); and (18) [combo 551], preferably said immunological active component comprises a live modified form, a killed form, or an immunological active part of said swine pathogens (12); (14), in particular (14a); and (18) [combo 552].

According to a further embodiment the immunological active component of [combo 1] is effective for the treatment and/or prophylaxis of infections caused by the swine pathogens (12); (14), in particular (14a); and (19) [combo 553], preferably said immunological active component comprises a live modified form, a killed form, or an immunological active part of said swine pathogens (12); (14), in particular (14a); and (19) [combo 554].

According to a further embodiment the immunological active component of [combo 1] is effective for the treatment and/or prophylaxis of infections caused by the swine pathogens (12); (14), in particular (14a); and (29), in particular (29a) [combo 555], preferably said immunological active component comprises a live modified form, a killed form, or an immunological active part of said swine pathogens (12); (14), in particular (14a); and (29), in particular (29a) [combo 556].

According to a further embodiment the immunological active component of [combo 1] is effective for the treatment and/or prophylaxis of infections caused by the swine pathogens (12); (15); and (16) [combo 557], preferably said immunological active component comprises a live modified form, a killed form, or an immunological active part of said swine pathogens (12); (15); and (16) [combo 558].

According to a further embodiment the immunological active component of [combo 1] is effective for the treatment and/or prophylaxis of infections caused by the swine pathogens (12); (15); and (17) [combo 559], preferably said immunological active component comprises a live modified form, a killed form, or an immunological active part of said swine pathogens (12); (15); and (17) [combo 560].

According to a further embodiment the immunological active component of [combo 1] is effective for the treatment and/or prophylaxis of infections caused by the swine pathogens (12); (15); and (18) [combo 561], preferably said immunological active component comprises a live modified form, a killed form, or an immunological active part of said swine pathogens (12); (15); and (18) [combo 562].

According to a further embodiment the immunological active component of [combo 1] is effective for the treatment and/or prophylaxis of infections caused by the swine pathogens (12); (15); and (19) [combo 563], preferably said immunological active component comprises a live modified form, a killed form, or an immunological active part of said swine pathogens (12); (15); and (19) [combo 564].

According to a further embodiment the immunological active component of [combo 1] is effective for the treatment and/or prophylaxis of infections caused by the swine pathogens (12); (15); and (29), in particular (29a) [combo 565], preferably said immunological active component comprises a live modified form, a killed form, or an immunological active part of said swine pathogens (12); (15); and (29), in particular (29a) [combo 566].

According to a further embodiment the immunological active component of [combo 1] is effective for the treatment and/or prophylaxis of infections caused by the swine pathogens (12); (16); and (17) [combo 567], preferably said immunological active component comprises a live modified form, a killed form, or an immunological active part of said swine pathogens (12); (15); and (17) [combo 568].

According to a further embodiment the immunological active component of [combo 1] is effective for the treatment and/or prophylaxis of infections caused by the swine pathogens (12); (16); and (18) [combo 569], preferably said immunological active component comprises a live modified form, a killed form, or an immunological active part of said swine pathogens (12); (16); and (18) [combo 570].

According to a further embodiment the immunological active component of [combo 1] is effective for the treatment and/or prophylaxis of infections caused by the swine pathogens (12); (16); and (19) [combo 571], preferably said immunological active component comprises a live modified form, a killed form, or an immunological active part of said swine pathogens (12); (16); and (19) [combo 572].

According to a further embodiment the immunological active component of [combo 1] is effective for the treatment and/or prophylaxis of infections caused by the swine pathogens (12); (16); and (29), in particular (29a) [combo 573], preferably said immunological active component comprises a live modified form, a killed form, or an immunological active part of said swine pathogens (12); (16); and (29), in particular (29a) [combo 574].

According to a further embodiment the immunological active component of [combo 1] is effective for the treatment and/or prophylaxis of infections caused by the swine pathogens (12); (17); and (18) [combo 575], preferably said immunological active component comprises a live modified form, a killed form, or an immunological active part of said swine pathogens (12); (17); and (18) [combo 576].

According to a further embodiment the immunological active component of [combo 1] is effective for the treatment and/or prophylaxis of infections caused by the swine pathogens (12); (17); and (19) [combo 577], preferably said immunological active component comprises a live modified form, a killed form, or an immunological active part of said swine pathogens (12); (17); and (19) [combo 578].

According to a further embodiment the immunological active component of [combo 1] is effective for the treatment and/or prophylaxis of infections caused by the swine pathogens (12); (17); and (29), in particular (29a) [combo 579], preferably said immunological active component comprises a live modified form, a killed form, or an immunological active part of said swine pathogens (12); (17); and (29), in particular (29a) [combo 580].

According to a further embodiment the immunological active component of [combo 1] is effective for the treatment and/or prophylaxis of infections caused by the swine pathogens (12); (18); and (19) [combo 581], preferably said immunological active component comprises a live modified form, a killed form, or an immunological active part of said swine pathogens (12); (18); and (19) [combo 582].

According to a further embodiment the immunological active component of [combo 1] is effective for the treatment and/or prophylaxis of infections caused by the swine pathogens (12); (18); and (29), in particular (29a) [combo 583], preferably said immunological active component comprises a live modified form, a killed form, or an immunological active part of said swine pathogens (12); (18); and (29), in particular (29a) [combo 584].

According to a further embodiment the immunological active component of [combo 1] is effective for the treatment and/or prophylaxis of infections caused by the swine pathogens (12); (19); and (29), in particular (29a) [combo 585], preferably said immunological active component comprises a live modified form, a killed form, or an immunological active part of said swine pathogens (12); (19); and (29), in particular (29a) [combo 586].

According to a further embodiment the immunological active component of [combo 1] is effective for the treatment and/or prophylaxis of infections caused by the swine pathogens (13), in particular (13a); (10); and (14), in particular (14a) and/or (14b) [combo 587], preferably said immunological active component comprises a live modified form, a killed form, or an immunological active part of said swine pathogens (13), in particular (13a); (10); and (14), in particular (14a) and/or (14b) [combo 588].

According to a further embodiment the immunological active component of [combo 1] is effective for the treatment and/or prophylaxis of infections caused by the swine pathogens (13), in particular (13a); (10); and (15) [combo 589], preferably said immunological active component comprises a live modified form, a killed form, or an immunological active part of said swine pathogens (13), in particular (13a); (10); and (15) [combo 590].

According to a further embodiment the immunological active component of [combo 1] is effective for the treatment and/or prophylaxis of infections caused by the swine pathogens (13), in particular (13a); (10); and (16) [combo 591], preferably said immunological active component comprises a live modified form, a killed form, or an immunological active part of said swine pathogens (13), in particular (13a); (10); and (16) [combo 592].

According to a further embodiment the immunological active component of [combo 1] is effective for the treatment and/or prophylaxis of infections caused by the swine pathogens (13), in particular (13a); (10); and (17) [combo 593], preferably said immunological active component comprises a live modified form, a killed form, or an immunological active part of said swine pathogens (13), in particular (13a); (10); and (17) [combo 594].

According to a further embodiment the immunological active component of [combo 1] is effective for the treatment and/or prophylaxis of infections caused by the swine pathogens (13), in particular (13a); (10); and (18) [combo 595], preferably said immunological active component comprises a live modified form, a killed form, or an immunological active part of said swine pathogens (13), in particular (13a); (10); and (18) [combo 596].

According to a further embodiment the immunological active component of [combo 1] is effective for the treatment and/or prophylaxis of infections caused by the swine pathogens (13), in particular (13a); (10); and (19) [combo 597], preferably said immunological active component comprises a live modified form, a killed form, or an immunological active part of said swine pathogens (13), in particular (13a); (10); and (19) [combo 598].

According to a further embodiment the immunological active component of [combo 1] is effective for the treatment and/or prophylaxis of infections caused by the swine pathogens (13), in particular (13a); (10); and (29), in particular (29a) [combo 599], preferably said immunological active component comprises a live modified form, a killed form, or an immunological active part of said swine pathogens (13), in particular (13a); (10); and (29), in particular (29a) [combo 600].

According to a further embodiment the immunological active component of [combo 1] is effective for the treatment and/or prophylaxis of infections caused by the swine pathogens (13), in particular (13a); (14), in particular (14a); and (15) [combo 601], preferably said immunological active component comprises a live modified form, a killed form, or an immunological active part of said swine pathogen (13), in particular (13a); (14), in particular (14a); and (15) [combo 602].

According to a further embodiment the immunological active component of [combo 1] is effective for the treatment and/or prophylaxis of infections caused by the swine pathogens (13), in particular (13a); (14), in particular (14a); and (16) [combo 603], preferably said immunological active component comprises a live modified form, a killed form, or an immunological active part of said swine pathogens (13), in particular (13a); (14), in particular (14a); and (16) [combo 604].

According to a further embodiment the immunological active component of [combo 1] is effective for the treatment and/or prophylaxis of infections caused by the swine pathogens (13), in particular (13a); (14), in particular (14a); and (17) [combo 605], preferably said immunological active component comprises a live modified form, a killed form, or an immunological active part of said swine pathogens (13), in particular (13a); (14), in particular (14a); and (17) [combo 606].

According to a further embodiment the immunological active component of [combo 1] is effective for the treatment and/or prophylaxis of infections caused by the swine pathogens (13), in particular (13a); (14), in particular (14a); and (18) [combo 607], preferably said immunological active component comprises a live modified form, a killed form, or an immunological active part of said swine pathogens (13), in particular (13a); (14), in particular (14a); and (18) [combo 608].

According to a further embodiment the immunological active component of [combo 1] is effective for the treatment and/or prophylaxis of infections caused by the swine pathogens (13), in particular (13a); (14), in particular (14a); and (19) [combo 609], preferably said immunological active component comprises a live modified form, a killed form, or an immunological active part of said swine pathogens (13), in particular (13a); (14), in particular (14a); and (19) [combo 610].

According to a further embodiment the immunological active component of [combo 1] is effective for the treatment and/or prophylaxis of infections caused by the swine pathogens (13), in particular (13a); (14), in particular (14a); and (29), in particular (29a) [combo 611], preferably said immunological active component comprises a live modified form, a killed form, or an immunological active part of said swine pathogens (13), in particular (13a); (14), in particular (14a); and (29), in particular (29a) [combo 612].

According to a further embodiment the immunological active component of [combo 1] is effective for the treatment and/or prophylaxis of infections caused by the swine pathogens (13), in particular (13a); (15); and (16) [combo 613], preferably said immunological active component comprises a live modified form, a killed form, or an immunological active part of said swine pathogens (13), in particular (13a); (15); and (16) [combo 614].

According to a further embodiment the immunological active component of [combo 1] is effective for the treatment and/or prophylaxis of infections caused by the swine pathogens (13), in particular (13a); (15); and (17) [combo 615], preferably said immunological active component comprises a live modified form, a killed form, or an immunological active part of said swine pathogens (13), in particular (13a); (15); and (17) [combo 616].

According to a further embodiment the immunological active component of [combo 1] is effective for the treatment and/or prophylaxis of infections caused by the swine pathogens (13), in particular (13a); (15); and (18) [combo 617], preferably said immunological active component comprises a live modified form, a killed form, or an immunological active part of said swine pathogens (13), in particular (13a); (15); and (18) [combo 618].

According to a further embodiment the immunological active component of [combo 1] is effective for the treatment and/or prophylaxis of infections caused by the swine pathogens (13), in particular (13a); (15); and (19) [combo 619], preferably said immunological active component comprises a live modified form, a killed form, or an immunological active part of said swine pathogens (13), in particular (13a); (15); and (19) [combo 620].

According to a further embodiment the immunological active component of [combo 1] is effective for the treatment and/or prophylaxis of infections caused by the swine pathogens (13), in particular (13a); (15); and (29), in particular (29a) [combo 621], preferably said immunological active component comprises a live modified form, a killed form, or an immunological active part of said swine pathogens (13), in particular (13a); (15); and (29), in particular (29a) [combo 622].

According to a further embodiment the immunological active component of [combo 1] is effective for the treatment and/or prophylaxis of infections caused by the swine pathogens (13), in particular (13a); (16); and (17) [combo 623], preferably said immunological active component comprises a live modified form, a killed form, or an immunological active part of said swine pathogens (13), in particular (13a); (15); and (17) [combo 624].

According to a further embodiment the immunological active component of [combo 1] is effective for the treatment and/or prophylaxis of infections caused by the swine pathogens (13), in particular (13a); (16); and (18) [combo 625], preferably said immunological active component comprises a live modified form, a killed form, or an immunological active part of said swine pathogens (13), in particular (13a); (16); and (18) [combo 626].

According to a further embodiment the immunological active component of [combo 1] is effective for the treatment and/or prophylaxis of infections caused by the swine pathogens (13), in particular (13a); (16); and (19) [combo 627], preferably said immunological active component comprises a live modified form, a killed form, or an immunological active part of said swine pathogens (13), in particular (13a); (16); and (19) [combo 628].

According to a further embodiment the immunological active component of [combo 1] is effective for the treatment and/or prophylaxis of infections caused by the swine pathogens (13), in particular (13a); (16); and (29), in particular (29a) [combo 629], preferably said immunological active component comprises a live modified form, a killed form, or an immunological active part of said swine pathogens (13), in particular (13a); (16); and (29), in particular (29a) [combo 630].

According to a further embodiment the immunological active component of [combo 1] is effective for the treatment and/or prophylaxis of infections caused by the swine pathogens (13), in particular (13a); (17); and (18) [combo 631], preferably said immunological active component comprises a live modified form, a killed form, or an immunological active part of said swine pathogens (13), in particular (13a); (17); and (18) [combo 632].

According to a further embodiment the immunological active component of [combo 1] is effective for the treatment and/or prophylaxis of infections caused by the swine pathogens (13), in particular (13a); (17); and (19) [combo 633], preferably said immunological active component comprises a live modified form, a killed form, or an immunological active part of said swine pathogens (13), in particular (13a); (17); and (19) [combo 634].

According to a further embodiment the immunological active component of [combo 1] is effective for the treatment and/or prophylaxis of infections caused by the swine pathogens (13), in particular (13a); (17); and (29), in particular (29a) [combo 635], preferably said immunological active component comprises a live modified form, a killed form, or an immunological active part of said swine pathogens (13), in particular (13a); (17); and (29), in particular (29a) [combo 636].

According to a further embodiment the immunological active component of [combo 1] is effective for the treatment and/or prophylaxis of infections caused by the swine pathogens (13), in particular (13a); (18); and (19) [combo 637], preferably said immunological active component comprises a live modified form, a killed form, or an immunological active part of said swine pathogens (13), in particular (13a); (18); and (19) [combo 638].

According to a further embodiment the immunological active component of [combo 1] is effective for the treatment and/or prophylaxis of infections caused by the swine pathogens (13), in particular (13a); (18); and (29), in particular (29a) [combo 639], preferably said immunological active component comprises a live modified form, a killed form, or an immunological active part of said swine pathogens (13), in particular (13a); (18); and (29), in particular (29a) [combo 640].

According to a further embodiment the immunological active component of [combo 1] is effective for the treatment and/or prophylaxis of infections caused by the swine pathogens (13), in particular (13a); (19); and (29), in particular (29a) [combo 641], preferably said immunological active component comprises a live modified form, a killed form, or an immunological active part of said swine pathogens (13), in particular (13a); (19); and (29), in particular (29a) [combo 642].

According to a further embodiment the immunological active component of [combo 1] is effective for the treatment and/or prophylaxis of infections caused by the swine pathogens (14), in particular (14a) and/or (14b); (10); and (15) [combo 643], preferably said immunological active component comprises a live modified form, a killed form, or an immunological active part of said swine pathogens (14), in particular (14a) and/or (14b); (10); and (15) [combo 644].

According to a further embodiment the immunological active component of [combo 1] is effective for the treatment and/or prophylaxis of infections caused by the swine pathogens (14), in particular (14a) and/or (14b); (10); and (16) [combo 645], preferably said immunological active component comprises a live modified form, a killed form, or an immunological active part of said swine pathogens (14), in particular (14a) and/or (14b); (10); and (16) [combo 646].

According to a further embodiment the immunological active component of [combo 1] is effective for the treatment and/or prophylaxis of infections caused by the swine pathogens (14), in particular (14a) and/or (14b); (10); and (17) [combo 647], preferably said immunological active component comprises a live modified form, a killed form, or an immunological active part of said swine pathogens (14), in particular (14a) and/or (14b); (10); and (17) [combo 648].

According to a further embodiment the immunological active component of [combo 1] is effective for the treatment and/or prophylaxis of infections caused by the swine pathogens (14), in particular (14a) and/or (14b); (10); and (18) [combo 649], preferably said immunological active component comprises a live modified form, a killed form, or an immunological active part of said swine pathogens (14), in particular (14a) and/or (14b); (10); and (18) [combo 650].

According to a further embodiment the immunological active component of [combo 1] is effective for the treatment and/or prophylaxis of infections caused by the swine pathogens (14), in particular (14a) and/or (14b); (10); and (19) [combo 651], preferably said immunological active component comprises a live modified form, a killed form, or an immunological active part of said swine pathogens (14), in particular (14a) and/or (14b); (10); and (19) [combo 652].

According to a further embodiment the immunological active component of [combo 1] is effective for the treatment and/or prophylaxis of infections caused by the swine pathogens (14), in particular (14a) and/or (14b); (10); and (29), in particular (29a) [combo 653], preferably said immunological active component comprises a live modified form, a killed form, or an immunological active part of said swine pathogens (14), in particular (14a) and/or (14b); (10); and (29), in particular (29a) [combo 654].

According to a further embodiment the immunological active component of [combo 1] is effective for the treatment and/or prophylaxis of infections caused by the swine pathogens (14), in particular (14a) and/or (14b); (15); and (16) [combo 655], preferably said immunological active component comprises a live modified form, a killed form, or an immunological active part of said swine pathogens (14), in particular (14a) and/or (14b); (15); and (16) [combo 656].

According to a further embodiment the immunological active component of [combo 1] is effective for the treatment and/or prophylaxis of infections caused by the swine pathogens (14), in particular (14a) and/or (14b); (15); and (17) [combo 657], preferably said immunological active component comprises a live modified form, a killed form, or an immunological active part of said swine pathogens (14), in particular (14a) and/or (14b); (15); and (17) [combo 658].

According to a further embodiment the immunological active component of [combo 1] is effective for the treatment and/or prophylaxis of infections caused by the swine pathogens (14), in particular (14a) and/or (14b); (15); and (18) [combo 659], preferably said immunological active component comprises a live modified form, a killed form, or an immunological active part of said swine pathogens (14), in particular (14a) and/or (14b); (15); and (18) [combo 660].

According to a further embodiment the immunological active component of [combo 1] is effective for the treatment and/or prophylaxis of infections caused by the swine pathogens (14), in particular (14a) and/or (14b); (15); and (19) [combo 661], preferably said immunological active component comprises a live modified form, a killed form, or an immunological active part of said swine pathogens (14), in particular (14a) and/or (14b); (15); and (19) [combo 662].

According to a further embodiment the immunological active component of [combo 1] is effective for the treatment and/or prophylaxis of infections caused by the swine pathogens (14), in particular (14a) and/or (14b); (15); and (29), in particular (29a) [combo 663], preferably said immunological active component comprises a live modified form, a killed form, or an immunological active part of said swine pathogens (14), in particular (14a) and/or (14b); (15); and (29), in particular (29a) [combo 664].

According to a further embodiment the immunological active component of [combo 1] is effective for the treatment and/or prophylaxis of infections caused by the swine pathogens (14), in particular (14a) and/or (14b); (16); and (17) [combo 665], preferably said immunological active component comprises a live modified form, a killed form, or an immunological active part of said swine pathogens (14), in particular (14a) and/or (14b); (15); and (17) [combo 666].

According to a further embodiment the immunological active component of [combo 1] is effective for the treatment and/or prophylaxis of infections caused by the swine pathogens (14), in particular (14a) and/or (14b); (16); and (18) [combo 667], preferably said immunological active component comprises a live modified form, a killed form, or an immunological active part of said swine pathogens (14), in particular (14a) and/or (14b); (16); and (18) [combo 668].

According to a further embodiment the immunological active component of [combo 1] is effective for the treatment and/or prophylaxis of infections caused by the swine pathogens (14), in particular (14a) and/or (14b); (16); and (19) [combo 669], preferably said immunological active component comprises a live modified form, a killed form, or an immunological active part of said swine pathogens (14), in particular (14a) and/or (14b); (16); and (19) [combo 670].

According to a further embodiment the immunological active component of [combo 1] is effective for the treatment and/or prophylaxis of infections caused by the swine pathogens (14), in particular (14a) and/or (14b); (16); and (29), in particular (29a) [combo 671], preferably said immunological active component comprises a live modified form, a killed form, or an immunological active part of said swine pathogens (14), in particular (14a) and/or (14b); (16); and (29), in particular (29a) [combo 672].

According to a further embodiment the immunological active component of [combo 1] is effective for the treatment and/or prophylaxis of infections caused by the swine pathogens (14), in particular (14a) and/or (14b); (17); and (18) [combo 673], preferably said immunological active component comprises a live modified form, a killed form, or an immunological active part of said swine pathogens (14), in particular (14a) and/or (14b); (17); and (18) [combo 674].

According to a further embodiment the immunological active component of [combo 1] is effective for the treatment and/or prophylaxis of infections caused by the swine pathogens (14), in particular (14a) and/or (14b); (17); and (19) [combo 675], preferably said immunological active component comprises a live modified form, a killed form, or an immunological active part of said swine pathogens (14), in particular (14a) and/or (14b); (17); and (19) [combo 676].

According to a further embodiment the immunological active component of [combo 1] is effective for the treatment and/or prophylaxis of infections caused by the swine pathogens (14), in particular (14a) and/or (14b); (17); and (29), in particular (29a) [combo 677], preferably said immunological active component comprises a live modified form, a killed form, or an immunological active part of said swine pathogens (14), in particular (14a) and/or (14b); (17); and (29), in particular (29a) [combo 678].

According to a further embodiment the immunological active component of [combo 1] is effective for the treatment and/or prophylaxis of infections caused by the swine pathogens (14), in particular (14a) and/or (14b); (18); and (19) [combo 679], preferably said immunological active component comprises a live modified form, a killed form, or an immunological active part of said swine pathogens (14), in particular (14a) and/or (14b); (18); and (19) [combo 680].

According to a further embodiment the immunological active component of [combo 1] is effective for the treatment and/or prophylaxis of infections caused by the swine pathogens (14), in particular (14a) and/or (14b); (18); and (29), in particular (29a) [combo 681], preferably said immunological active component comprises a live modified form, a killed form, or an immunological active part of said swine pathogens (14), in particular (14a) and/or (14b); (18); and (29), in particular (29a) [combo 682].

According to a further embodiment the immunological active component of [combo 1] is effective for the treatment and/or prophylaxis of infections caused by the swine pathogens (14), in particular (14a) and/or (14b); (19); and (29), in particular (29a) [combo 683], preferably said immunological active component comprises a live modified form, a killed form, or an immunological active part of said swine pathogens (14), in particular (14a) and/or (14b); (19); and (29), in particular (29a) [combo 684].

According to a further embodiment the immunological active component of [combo 1] is effective for the treatment and/or prophylaxis of infections caused by the swine pathogens (16); (10); and (15) [combo 685], preferably said immunological active component comprises a live modified form, a killed form, or an immunological active part of said swine pathogens (16); (10); and (15) [combo 686].

According to a further embodiment the immunological active component of [combo 1] is effective for the treatment and/or prophylaxis of infections caused by the swine pathogens (16); (10); and (17) [combo 687], preferably said immunological active component comprises a live modified form, a killed form, or an immunological active part of said swine pathogens (16); (10); and (17) [combo 688].

According to a further embodiment the immunological active component of [combo 1] is effective for the treatment and/or prophylaxis of infections caused by the swine pathogens (16); (10); and (18) [combo 689], preferably said immunological active component comprises a live modified form, a killed form, or an immunological active part of said swine pathogens (16); (10); and (18) [combo 690].

According to a further embodiment the immunological active component of [combo 1] is effective for the treatment and/or prophylaxis of infections caused by the swine pathogens (16); (10); and (19) [combo 691], preferably said immunological active component comprises a live modified form, a killed form, or an immunological active part of said swine pathogens (16); (10); and (19) [combo 692].

According to a further embodiment the immunological active component of [combo 1] is effective for the treatment and/or prophylaxis of infections caused by the swine pathogens (16); (10); and (29), in particular (29a) [combo 693], preferably said immunological active component comprises a live modified form, a killed form, or an immunological active part of said swine pathogens (16); (10); and (29), in particular (29a) [combo 694].

According to a further embodiment the immunological active component of [combo 1] is effective for the treatment and/or prophylaxis of infections caused by the swine pathogens (16);; (15); and (17) [combo 695], preferably said immunological active component comprises a live modified form, a killed form, or an immunological active part of said swine pathogens (16); (15); and (17) [combo 696].

According to a further embodiment the immunological active component of [combo 1] is effective for the treatment and/or prophylaxis of infections caused by the swine pathogens (16); (15); and (18) [combo 697], preferably said immunological active component comprises a live modified form, a killed form, or an immunological active part of said swine pathogens (16); (15); and (18) [combo 698].

According to a further embodiment the immunological active component of [combo 1] is effective for the treatment and/or prophylaxis of infections caused by the swine pathogens (16); (15); and (19) [combo 699], preferably said immunological active component comprises a live modified form, a killed form, or an immunological active part of said swine pathogens (16); (15); and (19) [combo 700].

According to a further embodiment the immunological active component of [combo 1] is effective for the treatment and/or prophylaxis of infections caused by the swine pathogens (16); (15); and (29), in particular (29a) [combo 701], preferably said immunological active component comprises a live modified form, a killed form, or an immunological active part of said swine pathogens (16); (15); and (29), in particular (29a) [combo 702].

According to a further embodiment the immunological active component of [combo 1] is effective for the treatment and/or prophylaxis of infections caused by the swine pathogens (16); (17); and (18) [combo 703], preferably said immunological active component comprises a live modified form, a killed form, or an immunological active part of said swine pathogens (16); (17); and (18) [combo 704].

According to a further embodiment the immunological active component of [combo 1] is effective for the treatment and/or prophylaxis of infections caused by the swine pathogens (16); (17); and (19) [combo 705], preferably said immunological active component comprises a live modified form, a killed form, or an immunological active part of said swine pathogens (16); (17); and (19) [combo 706].

According to a further embodiment the immunological active component of [combo 1] is effective for the treatment and/or prophylaxis of infections caused by the swine pathogens (16); (17); and (29), in particular (29a) [combo 707], preferably said immunological active component comprises a live modified form, a killed form, or an immunological active part of said swine pathogens (16); (17); and (29), in particular (29a) [combo 708].

According to a further embodiment the immunological active component of [combo 1] is effective for the treatment and/or prophylaxis of infections caused by the swine pathogens (16); (18); and (19) [combo 709], preferably said immunological active component comprises a live modified form, a killed form, or an immunological active part of said swine pathogens (16); (18); and (19) [combo 710].

According to a ftther embodiment the immunological active component of [combo 1] is effective for the treatment and/or prophylaxis of infections caused by the swine pathogens (16); (18); and (29), in particular (29a) [combo 711], preferably said immunological active component comprises a live modified form, a killed form, or an immunological active part of said swine pathogens (16); (18); and (29), in particular (29a) [combo 712].

According to a further embodiment the immunological active component of [combo 1] is effective for the treatment and/or prophylaxis of infections caused by the swine pathogens (16); (19); and (29), in particular (29a) [combo 713], preferably said immunological active component comprises a live modified form, a killed form, or an immunological active part of said swine pathogens (16); (19); and (29), in particular (29a) [combo 714].

According to a further embodiment the immunological active component of [combo 1] is effective for the treatment and/or prophylaxis of infections caused by the swine pathogens (14), in particular (14a), (16); (17); and (11) [combo 715], preferably said immunological active component comprises a live modified form, a killed form, or an immunological active part of said swine pathogens (14), in particular (14a), (16); (17); and (11) [combo 716].

According to a further embodiment the immunological active component of [combo 1] is effective for the treatment and/or prophylaxis of infections caused by the swine pathogens (14), in particular (14a), (16); (17); and (9) [combo 717], preferably said immunological active component comprises a live modified form, a killed form, or an immunological active part of said swine pathogens (14), in particular (14a), (16); (17); and (9) [combo 718].

According to a further embodiment the immunological active component of [combo 1] is effective for the treatment and/or prophylaxis of infections caused by the swine pathogens (14), in particular (14a), (16); (17); and (10) [combo 719], preferably said immunological active component comprises a live modified form, a killed form, or an immunological active part of said swine pathogens (14), in particular (14a), (16); (17); and (10) [combo 720].

According to a further embodiment the immunological active component of [combo 1] is effective for the treatment and/or prophylaxis of infections caused by the swine pathogens (14), in particular (14a), (16); (17); and (12) [combo 721], preferably said immunological active component comprises a live modified form, a killed form, or an immunological active part of said swine pathogens (14), in particular (14a), (16); (17); and (12) [combo 722].

According to a further embodiment the immunological active component of [combo 1] is effective for the treatment and/or prophylaxis of infections caused by the swine pathogen (13), in particular (13a) [combo 723], preferably said immunological active component comprises a live modified form, a killed form, or an immunological active part of said swine pathogens (14), in particular (14a), (16); (17); and (13), in particular (13a) [combo 724].

According to a further embodiment the immunological active component of [combo 1] is effective for the treatment and/or prophylaxis of infections caused by the swine pathogens (14), in particular (14a), (16); (17); and (15) [combo 725], preferably said immunological active component comprises a live modified form, a killed form, or an immunological active part of said swine pathogens (14), in particular (14a), (16); (17); and (15) [combo 726].

According to a further embodiment the immunological active component of [combo 1] is effective for the treatment and/or prophylaxis of infections caused by the swine pathogens (14), in particular (14a), (16); (17); and (18) [combo 727], preferably said immunological active component comprises a live modified form, a killed form, or an immunological active part of said swine pathogens (14), in particular (14a), (16); (17); and (18) [combo 728].

According to a further embodiment the immunological active component of [combo 1] is effective for the treatment and/or prophylaxis of infections caused by the swine pathogens (14), in particular (14a), (16); (17); and (19) [combo 729], preferably said immunological active component comprises a live modified form, a killed form, or an immunological active part of said swine pathogens (14), in particular (14a), (16); (17); and (19) [combo 730].

According to a fiuther embodiment the immunological active component of [combo 1] is effective for the treatment and/or prophylaxis of infections caused by the swine pathogens (14), in particular (14a), (16); (17); and (29), in particular (29a) [combo 731], preferably said immunological active component comprises a live modified form, a killed form, or an immunological active part of said swine pathogens (14), in particular (14a), (16); (17); and (29), in particular (29a) [combo 732].

According to a further embodiment the immunological active component of [combo 1] is effective for the treatment and/or prophylaxis of infections caused by the swine pathogens (9), (11); (12); (14), in particular (14a); (16); and (17) [combo 733], preferably said immunological active component comprises a live modified form, a killed form, or an immunological active part of said swine pathogens (9); (11); (12); (14), in particular (14a), (16); and (17) [combo 734].

According to a further embodiment, the present invention relates to a combination vaccine according to [combo 733 or 734], that further comprises an immunological active component effective for the treatment and/or prophylaxis of infections caused by infections caused by swine pathogen (13), in particular (13a); [combo 735], or preferably, wherein said further immunological active component comprises a live modified form, a killed form, or an immunological active part of said swine pathogen (13), in particular (13a) [combo 736].

According to a further embodiment, the present invention relates to a combination vaccine according to any one of [combo 733, 734, 735 or 736], that further comprises an immunological active component effective for the treatment and/or prophylaxis of infections caused by infections caused by swine pathogen (10) [combo 737], or preferably, wherein said further immunological active component comprises a live modified form, a killed form, or an immunological active part of said swine pathogen (10), [combo 738].

According to a further embodiment, the present invention relates to a combination vaccine according to any one of [combo 733, 734, 735, 736, 737 or 738], that further comprises an immunological active component effective for the treatment and/or prophylaxis of infections caused by infections caused by swine pathogen (1), in particular (1a) and /or (1b) [combo 739], or preferably, wherein said further immunological active component comprises a live modified form, a killed form, or an immunological active part of said swine pathogen (1), in particular (1a) and /or (1b) [combo 740].

According to a further embodiment, the present invention relates to a combination vaccine according to any one of [combo 733, 734, 735, 736, 737, 738, 739 or 740], that further comprises an immunological active component effective for the treatment and/or prophylaxis of infections caused by infections caused by swine pathogen (29), in particular (29a) [combo 741], or preferably, wherein said further immunological active component lo comprises a live modified form, a killed form, or an immunological active part of said swine pathogen (29), in particular (29a) [combo 742].

According to a further embodiment, the present invention relates to a combination vaccine according to any one of [combo 733, 734, 735, 736, 737, 738, 739, 740, 741 or 742], that further comprises an immunological active component effective for the treatment 15 and/or prophylaxis of infections caused by infections caused by swine pathogen (15) [combo 743], or preferably, wherein said further immunological active component comprises a live modified form, a killed form, or an immunological active part of said swine pathogen (15) [combo 744].

According to a further embodiment, the present invention relates to a combination 20 vaccine according to any one of [combo 733, 734, 735, 736, 737, 738, 739, 740, 741, 742, 743 or 744], that further comprises an immunological active component effective for the treatment and/or prophylaxis of infections caused by infections caused by swine pathogen (18) [combo 745], or preferably, wherein said further immunological active component comprises a live modified form, a killed form, or an immunological active part of said swine pathogen (18) [combo 746].

According to a further embodiment, the present invention relates to a combination vaccine according to any one of [combo 733, 734, 735, 736, 737, 738, 739, 740, 741, 742, 743, 744, 745 or 746], that further comprises an immunological active component effective for the treatment and/or prophylaxis of infections caused by infections caused by swine pathogen (19) [combo 747], or preferably, wherein said further immunological active component comprises a live modified form, a killed form, or an immunological active part of said swine pathogen (19) [combo 748].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747 or 748], that further comprises an immunological active component effective for the treatment and/or prophylaxis of infections caused by infections caused by swine pathogen (2) [combo 749], or preferably, wherein said further immunological active component comprises a live modified form, a killed form, or an immunological active part of said swine pathogen (2) [combo 750].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749 or 750], that further comprises an immunological active component effective for the treatment and/or prophylaxis of infections caused by infections caused by swine pathogen (3) [combo 751], or preferably, wherein said further immunological active component comprises a live modified form, a killed form, or an immunological active part of said swine pathogen (3) [combo 752].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751 or 752], that further comprises an immunological active component effective for the treatment and/or prophylaxis of infections caused by infections caused by swine pathogen (4) [combo 753], or preferably, wherein said further immunological active component comprises a live modified form, a killed form, or an immunological active part of said swine pathogen (4) [combo 754].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753 or 754], that further comprises an immunological active component effective for the treatment and/or prophylaxis of infections caused by infections caused by swine pathogen (5), in particular (5a) and/or (5b) [combo 755], or preferably, wherein said further immunological active component comprises a live modified form, a killed form, or an immunological active part of said swine pathogen (5), in particular (5a) and/or (5b) [combo 756].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755 or 756], that further comprises an immunological active component effective for the treatment and/or prophylaxis of infections caused by infections caused by swine pathogen (6), in particular (6a), (6b), (6c), (6d) and/or (6e) [combo 757], or preferably, wherein said further immunological active component comprises a live modified form, a killed form, or an immunological active part of said swine pathogen (6), in particular (6a), (6b), (6c), (6d) and/or (6e) [combo 758].

According to a further embodiment, the present invention relates to a combination vaccine according to any one of (combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757 or 758], that fiuther comprises an immunological active component effective for the treatment and/or prophylaxis of infections caused by infections caused by swine pathogen (20) [combo 759], or preferably, wherein said further immunological active component comprises a live modified form, a killed form, or an immunological active part of said swine pathogen (20) [combo 760].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759 or 760], that further comprises an immunological active component effective for the treatment and/or prophylaxis of infections caused by infections caused by swine pathogen (21), in particular (21a), (21b) and/or (21c) [combo 761], or preferably, wherein said further immunological active component comprises a live modified form, a killed form, or an immunological active part of said swine pathogen (21), in particular (21a), (21b) and/or (21c) [combo 762].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761 or 762], that further comprises an immunological active component effective for the treatment and/or prophylaxis of infections caused by infections caused by swine pathogen (22) [combo 763], or preferably, wherein said further immunological active component comprises a live modified form, a killed form, or an immunological active part of said swine pathogen (22) [combo 764].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763 or 764], that further comprises an immunological active component effective for the treatment and/or prophylaxis of infections caused by infections caused by swine pathogens (29b) and/or (29c), in particular (29c1) [combo 765], or preferably, wherein said further immunological active component comprises a live modified form, a killed form, or an immunological active part of said swine pathogens (29b) and/or (29c), in particular (29c1) [combo 766].

According to a further embodiment, the present invention relates to a combination vaccme according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765 or 766], that further comprises an immunological active component effective for the treatment and/or prophylaxis of infections caused by infections caused by swine pathogen (30) [combo 767], or preferably, wherein said further immunological active component comprises a live modified form, a killed form, or an immunological active part of said swine pathogen (30) [combo 768].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767 or 768], that further comprises an immunological active component effective for the treatment and/or prophylaxis of infections caused by infections caused by swine pathogen (31), in particular (31a), (31b), (31c), (31d), (31e), (31f), (31g), (31h) and/or (31i) [combo 769], or preferably, wherein said further immunological active component comprises a live modified form, a killed form, or an immunological active part of said swine pathogen (31), in particular (31a), (31b), (31c), (31d), (31e), (31f), (31g), (31h) and/or 770].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767 768, 769 or 770], that further comprises an immunological active component effective for the treatment and/or prophylaxis of infections caused by infections caused by swine pathogens (7), (8), (23), (24), (25), (26), (27), (28) (32), (33), (34), (35), (36), (37), (38), (39), (40), (41), (42), (43) and/or (44) [combo 771], or preferably, wherein said further immunological active component comprises a live modified form, a killed form, or an immunological active part of said swine pathogen (7), (8), (23), (24), (25), (26), (27), (28) (32), (33), (34), (35), (36), (37), (38), (39), (40), (41), (42), (43) and/or (44), [combo 772].

In one further embodiment, the combination vaccine comprises *L. intracellularis* and at least one immunological active component comprises a live modified form, a killed form, or an immunological active part of one or more swine pathogens selected from the group consisting of: (1b); (11); (4); (6), in particular (6a), (6b), (6c), (6d) and/or (6e); and (44) [combo 773].

In another embodiment, the combination vaccine comprises *L. intracellularis* and at least one immunological active component comprises a live modified form, a killed form, or an immunological active part of one or more swine pathogens selected from the group consisting of: *Clostridium* spp. (e.g., *Clostridium tetani*), equine influenza virus (EIV) (e.g., EIV-1, EIV-2), equine herpes virus (EHV) (e.g., EHV-1, EHV-2, EHV-3, EHV-4, EHV-5, EHV-6, EHV-7, ), alphavirus (e.g., eastern encephalitis virus, western encephalitis virus, Venezuelan encephalitis virus), or West Nile virus [combo 774].

According to further aspect, the *L. intracellularis* antigen can also combined with the antigen(s), or with the final vaccine formulation listed below [combo 775]:ENTERISOL® SC-54; ENTERISOL® SC-54 FF; ENTERISOL® Coli 3Plus; ENTERISOL® Coli-Clost; INGELVAC® Aujeszky MLV; INGELVAC® APP ALC; INGELVAC® APP ALC; INGELVAC® AR4; INGELVAC® ERY-ALC; INGELVAC® Flu; HP-1INGELVAC® HP-1; INGELVAC®M. HYO; INGELVAC® PRRS ATP; INGELVAC®PRRS MLV; INGELVAC® PRRS KV; INGELVACGPRV-G1; REPROCYC® PRRS-PLE; TETGUARD™; TOXIVAC® AD+E; TOXIVAC® PLUS PARASUIS (Boehringer Ingelheim); ARGUS® SC/ST; E-BAC®; END-FLUENCE®; END-FLUENCE®2; MAGESTIC®7 with SPUR®; MYCO SILENCER® BPM; MYCO SILENCER® BPME; MYCO SILENCER® M; MYCO SILENCER® MEH; MYCO SILENCER® Once; PORCILIS® APP; PORCILIS® AR-T; PORCILIS® Begonia; PORCILIS® Glässer; PORCILIS® PRRS; PROSYSTEM® CE; PROSYSTEM® Pilimune; PROSYSTEM® RCE; PROSYSTEM® TGE; PROSYSTEM® TGE/Rota; PROSYSTEM® TREC; RHINOGEN® BPE; RHINOGEN® CTE 5000; SOW BAC® CE II; SOW BAC® E II; SOW BAC® TREC; STREP BAC® with Imugen® II; SUPER-TET® with HAVLOGEN (Intervet Inc.); BratiVac-6; ER BAC® PLUS/LEPTOFERM-5®; ER BAC PLUS; FARROWSURE® PLUS; FARROWSURE® PLUS B; FLUSURE™; FLUSURE™ RTU; FLUSURE™/IER BAC® PLUS; FLUSURE™/RESPISURE®; FLUSURE™/ RESPISURE ONE®; FLUSURE™/RESPISURE® RTU; FLUSURE™/RESPISURE-ONE®/ER BAC® PLUS; LITTERGUARD®; LITTERGUARD® LT; LITTERGUARD® LT-C; PARVO-VAC®/LEPTOFERM-5®; RESPISURE®; RESPISURE/ER® Bac Plus®; RESPISURE-ONE®; RESPISURE-ONE/ER BAC PLUS (Pfizer Inc.); HYORESP®; NEOCOLIPOR®; PROGRESSIS® (Merial LTD); M+PAC®, MAXIVAC® XL3, SS PAC®, PNEU PAC®, PARAPAC®; PNEU PAC®–ER; AR-PARAPAC®+ER; PNEU PARAPAC®+ER; AR-Pac-P®+ER; SCOURMUNE®; PRV/Marker Gold®; PRV/MARKER GOLD®; MAXIVAC-FLU® (Schering Plough Animal Health Corporation); SUVAXYN® RESPIFEND® MH; SUVAXYN® MH-one; SUVAXYN® RESPIFEND® MH/HPS; SUVAXYN® RESPIFEND® HPS; SUVAXYN® RESPIFEND® APP; SUVAXYN® SIV/MH-one; SUVAXYN® SIV (H1N1 and H3N2); SUVAXYN®P; SUVAXYN® PLE; SUVAXYN® PLE+B; SUVAXYN® LE+B; SUVAXYN® PLE/PRVgpI⁻; SUVAXYN® PLE+B/PRVgpI; SUVAXYN® PRVgpI⁻; SUVAXYN® EC-4; SUVAXYN® E; SUVAXYN® E-oral (Fort Dodge Animal Health); ENDOVAC-PORCI® (Immvac, Inc.); ANTITOX TET™; DENAGARD®; MYCO SHIELD™; PARVO SHIELD® L5E; PNEUMOSTAR® Myco; PNEUMOSTAR® SIV; PORCINE PILI SHIELD™+C; PREFARROW SHIELD™9; RHINICELL® FD; RHINI SHIELD™ TX4; SALMO SHIELD® Live (Novartis Animal Health); Breed Sow 6; Breed Sow 7; E Colicin S 3; E Colicin S 3+C; Erysipelas Bacterin; Lepto 5; Swine Master M Plus (AgriLabs).

A further aspect relates to a container that comprises at least one dose of the *L. intracellularis* antigen and at least one dose of the further immunological active component of one or more of other swine pathogens as listed above. Preferably that container comprises at least one dose of the *L. intracellularis* antigen and at least one dose of the immunological active components according to any one of [combo 1] to [combo 775] as described above. Preferably, said container comprises 1 to 250 doses each of the *L. intracellularis* antigen and the immunological active components according to any one of [combo 1] to [combo 775] as described above. Preferably it contains 1, 10, 25, 50, 100, 150, 200, or 250 doses each of the *L. intracellularis* antigen and the immunological active components according to any one of [combo 1] to [combo 775]. Preferably, each of the containers further comprises an antimicrobiological active agent. Those agents are for example antibiotics including Gentamicin and Merthiolate and the like.

The present invention also relates to a kit, that comprises *L. intracellularis* antigen and the further immunological active components of one or more of the other swine pathogens as listed. Preferably the kit comprises *L. intracellularis* antigen and the further immunological active components according to any one of [combo 1] to [combo 775].

The present invention also relates to a kit, that comprises *L. intracellularis* antigen and the further immunological active components of one or more of the other swine pathogens as listed in one container. Preferably, the kit comprises *L. intracellularis* antigen and the further immunological active components according to any one of [combo 1] to [combo 775] in one container. According to a further aspect, the present invention also relates to a kit that comprises *L. intracellularis* antigen and the further immunological active components of one or more of the other swine pathogens as listed in two or more containers. Preferably, the kit comprises *L. intracellularis* antigen and the further immunological active components according to any one of [combo 1] to [combo 775] in two or more containers. For example, *L. intracellularis* antigen may be provided in one container, and the further immunological active components, preferably any one of [combo 1] to [combo 775] may be provide in a separate container. Both containers are part of the kit. It is within the meaning of the present invention, that each container may include a mixture of *L. intracellularis* antigen, a mixture of at least of one but not all of the further immunological active components, preferably any one of [combo 1] to [combo 775], or a mixture of *L. intracellularis* antigen and at least of one but not all of the further immunological active components, preferably any one of [combo 1] to [combo 775]. The missing immunological active component(s) of that combination vaccine is then provided in one or more separate containers, which all are part of the kit. Thus, the combination vaccines as provided herewith can be provided as a multivalent vaccine that comprises all antigenic components in a single container, or in parts of a kit in form of separate containers, that comprise the *L. intracellularis* antigen and the immunological active components of any further swine pathogen as listed above, preferably according to any one of [combo 1] to [combo 775], in at least to separate containers.

A further aspect of the present invention relates to a kit, that comprises any of the containers described above, and an instruction manual, including the information for the administration of the *L. intracellularis* antigen and at least one dose of the immunological active components according to any one of [combo 1] to [combo 775] as described above. Moreover, according to a further aspect, said instruction manual comprises the information of a repeatable administration of at least one dose of said combination vaccines. According to a further aspect, said instruction manual also includes the information, to administer an immune stimulant prior to or simultaneously with the combination vaccine. This is preferably desirable when the combination vaccine consists of killed microorganisms, or parts of microorganisms, or a combination thereof. Preferably, said immune stimulant shall be given at least twice. A preferred immune stimulant is for example is keyhole limpet hemocyanin (KLH), still preferably emulsified with incomplete Freund's adjuvant (KLH/ICFA). However, it is herewith understood, that any other immune stimulant known to a person skilled in the art can also be used. "Immune stimulant" as used herein, means any agent or composition that can trigger the immune response, preferably without initiating or increasing a specific immune response, for example the immune response against a specific pathogen. It is further instructed to administer the immune stimulant in a suitable dose. According to a further aspect, the instruction manual comprises the information that all feed or otherwise administered antimicrobials shall be withheld around the time of vaccination, preferably at least 3 to 4 days prior to vaccination through 7 to 14 days post-vaccination. If the immunological active components, including the *L. intracellularis* antigen of the vaccines are dehydrated, e.g. by lyophilization, the container further comprises a suitable reconstituent, preferably in form of a physiologically acceptable solution. Preferably, it further comprises means, e.g. a syringe for reconstitution and/or administration.

Formulations

A further important aspect of the present invention is the preparation of the combination vaccine(s). The skilled person knows additional components which may be comprised in said composition (see also Remington's Pharmaceutical Sciences. (1990). 18th ed. Mack Publ., Easton). The expert may use known injectable, physiologically acceptable sterile solutions. For preparing a ready-to-use solution for parenteral injection or infusion, aqueous isotonic solutions, such as e.g. saline or corresponding plasma protein solutions are readily available. The pharmaceutical compositions may be present as lyophylisates or dry preparations, which can be reconstituted with a known injectable solution directly before use under sterile conditions, e.g. as a kit of parts.

In addition, the immunogenic and vaccine compositions of the present invention can include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like.

"Diluents" can include water, saline, dextrose, ethanol, glycerol, and the like. Isotonic agents can include sodium chloride, dextrose, mannitol, sorbitol, and lactose, among others. Stabilizers include albumin and alkalisalts of ethylendiamintetracetic acid, among others.

Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene ; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997). (The teachings and content of which are hereby incorporated by reference.)

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book. (The teachings and content of which are hereby incorporated by reference.)

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, Jun. 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Cabopol 971P. Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide among many others.

Preferably, the adjuvant is added in an amount of about 100 µg to about 10 mg per dose. Even more preferably, the adjuvant is added in an amount of about 100 µg to about 10 mg per dose. Even more preferred the adjuvant is added in an amount of about 500 µg to about 5 mg per dose. Even more preferred the adjuvant is added in an amount of about 750 µg to about 2.5 mg per dose. Most preferred the adjuvant is added in an amount of about 1 mg per dose.

The vaccine composition can further include one or more other immunomodulatory agents such as, e.g., interleukins, interferons, or other cytokines. The vaccine compositions can also include Gentamicin and Merthiolate. While the amounts and concentrations of adjuvants and additives useful in the context of the present invention can readily be determined by the skilled artisan, the present invention contemplates compositions comprising from about 50 ug to about 2000 ug of adjuvant and preferably about 250 ug/ml dose of the vaccine composition. In another preferred embodiment, the present invention contemplates vaccine compositions comprising from about 1 ug/ml to about 60 ug/ml of antibiotics, and more preferably less than about 30 ug/ml of antibiotics.

According to a further embodiment the combination vaccine is first dehydrated. If the composition is first lyophilized or dehydrated by other methods, then, prior to vaccination, said composition is rehydrated in aqueous (e.g. saline, PBS (phosphate buffered saline)) or non-aqueous solutions (e.g. oil emulsion (mineral oil, or vegetable/metabolizable oil based/single or double emulsion based), aluminum-based, carbomer based adjuvant).

As described above, the *L. intracellularis* antigen and any further immunological active components according to any one of [combo 1] to [combo 774] can be formulated as mono or multivalent formulations, whereas multivalent formulations are preferred. In the event, several mono and or multivalent formulations are prepared, it is preferred to package all components of the combination vaccine in one kit.

Dosage and Administration

According to the present invention, an effective amount of a combination vaccine administered to pigs provides effective immunity against microbiological infections or a decreased incidence of or severity of clinical signs caused by *L. intracellularis* and at least one further pathogen as listed above. Preferred combinations of antigens for the treatment and prophylaxis of microbiological diseases in pigs are listed above.

The combination vaccines according to the invention are generally administered to susceptible animals, preferably swine, in one or more doses. Live or killed vaccine may be administered 1 or 2 times at 2 to 4 week intervals. For the attenuated, live vaccines, one dose is preferred. Preferably, the first or single administration is performed when the animal is about 2 to 3 weeks to about 8 weeks of age. If a second administration is desirable or necessary, the second administration is performed about 1 to about 4 weeks after the first administration of the vaccine. According to a further aspect, revaccination is performed in an interval of 3 to 12 month after administration of any previous vaccination. Administration of subsequent vaccine doses is preferably done on an 6 month to an annual basis. In another preferred aspect, animals vaccinated before the age of about 2 to 3 weeks should be revaccinated. Administration of subsequent vaccine doses is preferably done on an annual basis.

The amount of combination vaccine that is effective depends on the ingredients of the vaccine and the schedule of administration. Typically, when an inactivated virus or a modified live virus preparation is used in the combination vaccine, an amount of the vaccine contains about $10^2$ to about $10^9$ TCID50 per dose, preferably about $10^3$ to about $10^8$ TCID50 per dose, more preferably, about $10^4$ to about $10^8$ TCID50 per dose. In general, inactivated antigen is normally used in higher amounts than live modified viruses.

Typically, when bacterial antigen is used in the combination vaccine, the vaccine contains an amount of about $10^3$ to about $10^9$ colony forming units (CFU) per dose, preferably, about $10^4$ to about $10^8$ (CFU) per dose, more preferably about $10^5$ to about $10^6$ (CFU) per dose.

In particular, when modified live *L. intracellularis* bacteria are used in the combination vaccines, e.g. the bacteria isolates designated isolate B3903, ATCC accession No. PTA-4926 and designated isolate N34NP40wk, ATCC accession No. 55783 (both described in WO 96/39629 and WO 05/011731), the recommended dose to be administered to the susceptible animal is preferably about 3.0 $TCID_{50}$ (tissue culture infective dose 50% end point)/dose to about 6.0 $TCID_{50}$/dose and more preferably about 4.0 $TCID_{50}$/dose to about 5.0 $TCID_{50}$/dose. In a preferred embodiment, the titer of the vaccine is about 4.9 $TCID_{50}$ /dose as determined by Tissue Culture Infective Dose 50% endpoint dilution assay ($TCID_{50}$). In general, the quantity of immunogen will be between 5 and 5000 micrograms, and between $10^{2.0}$ and $10^{9.0}$ $TCID_{50}$, preferably between $10^{3.0}$ and $10^{6.0}$ $TCID_{50}$, more preferably between $10^{4.0}$ and $10^{5.0}$ $TCID_{50}$, when purified bacteria are used.

In particular, when *Erysipelothirx rhusiopathiae* is used in the combination vaccines, e.g. in form of INGELVAC® Ery-ALC, the recommended dose to be administered to the susceptible animal is preferably about $1\times10^{8.0}$ CFU (colony form units)/dose to about $1\times10^{10.5}$ CFU /dose and more preferably about $1\times10^{9.0}$ CFU/dose to about $9\times10^{9.0}$ CFU/dose.

In particular, when *Sallmonella* spp., in particular avirulent *S. cholerasius* is used in The combination vaccines, e.g. in form of ENTERISOL® SC54FF, the recommended dose to be administered to the susceptible animal is preferably about $1\times10^{7.0}$ CFU (colony form units)/dose to about $1\times10^{9.0}$ CFU /dose and more preferably about $1\times10^{8.0}$ CFU/dose to about $6\times10^{8.0}$ CFU/dose.

Sub-unit vaccines are normally administered with an antigen inclusion level of at least 0.2 µg antigen per dose, preferably with about 0.2 to about 400 µg/dose, still more preferably with about 0.3 to about 200 µg/dose, even more preferably with about 0.35 to about 100 µg/dose, still more preferably with about 0.4 to about 50 µg/dose, still more preferably with about 0.45 to about 30 µg/dose, still more preferably with about 0.6 to about 15 µg/dose, even more preferably with about 0.75 to about 8 µg/dose, even more preferably with about 1.0 to about 6 µg/dose, still more preferably with about 1.3 to about 3.0 µg/dose.

The composition according to the invention may be applied intradermally, intratracheally, or intravaginally. The composition preferably may be applied intramuscularly or intranasally. In an animal body, it can prove advantageous to apply the pharmaceutical compositions as described above via an intravenous or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the compositions according to the invention may be administered once or several times, also intermittently, for instance on a daily basis for several days, weeks or months and in different dosages.

The vaccine compositions as provided herein are intended to be used as an immunogen in antimicrobial vaccines for pigs. However, where applicable, the vaccine compositions provided herewith can also be used for the treatment and prophylaxis of other animals, including birds, fish, and mammals such as cattle, horses, and primates.

Methods for Treatment

Yet another important aspect of the invention is a method for the prophylaxis or treatment of diseases and/or lessening of the clinical signs caused by *L. intracellularis,* and one or more other swine pathogenic microorganism(s), wherein *L. intracellularis* antigen is administered to a non-human animal in need thereof together with a further immunological active components effective for the treatment and/or prophylaxis of the infection caused by said other swine pathogenic microorganism. Relevant swine pathogenic microorganisms as well as preferred combination vaccines that can be used are those described above. According to a further aspect, the *L. intracellularis* antigen and at least one further immunological active component effective for the treatment and/or prophylaxis and/or a lessening of the clinical signs of the infection caused by another swine pathogenic microorganism other than *L. intracellularis* are administered in form of a single vial mixed formulation. Most preferred, all antigenic components, including the *L. intracellularis* antigen of those vaccines are mixed together in form of a single vial mixture. However, according to a further aspect of the method of treatment, the *L. intracellularis* antigen and one or more of the additional immunological active components effective for the treatment and/or prophylaxis of infection(s) caused by one or more other swine pathogenic microorganisms other than *L. intracellularis* are administered in the form of separate single vial formulations, that are administered separately at least within one week, preferably within 2 to 5 days, more preferably at 1 day, even more preferably within 12 hours, even more preferably within 6 hours, even more preferably within 3 hours, most preferably within 1 hour.

All publications and patents cited herein are incorporated by reference in their entireties.

The present invention is further described in the following examples which are provided for illustrative purposes only and are not to be construed as limiting. Indeed, other variants of the invention will be readily apparent to one of ordinary skill in the art.

EXAMPLES

Efficacy of a Combination Vaccine Comprising *Lawsonia intracellularis, Etysipelothrix rhusiopathiae* and *Salmonella cholerasuis* Antigen Test Substance(s):

*Lawsonia intracellularis* Vaccine, Avirulent Live Culture, trade name ENTERISOL® Ileitis FF, Product Code 10L1.00; *Lawsonia intracellularis* Vaccine, Avirulent Live Culture, trade name ENTERISOL® Ileitis Lyophilized, Product Code 10L1.01; *Erysipelothrix rhuisiopathiae* Vaccine, Live Culture, trade name INGELVAC® Ery-ALC, Product Code 1541.00; *Salmonella cholerasuis* Vaccine, Avirulent Live Culture, trade name ENTERISOL® SC-54FF, Product Code 19A1.00. All products are registered for Boehringer Ingelheim Vetmedica, Inc., St. Joseph, Mo., U.S.

Formulation

The test articles were combination vaccines consisting of 1 ml v/v each of ENTERISOL® Ileitis (FF or LYO)-ENTERISOL® SC-54, FF-Ingelvac® ERY-ALC FF. Three vials of each vaccine component were pooled individually. The ERY component was used in the vaccine formulations undiluted. The *L. intracellularis*, FF and LYO, and SC-54 components were diluted as shown below before addition to the final vaccine formulation.

*L. intracellularis*, FF dilution: 2.5 ml bacterin in 97.5 ml growth medium (1:40)

*L. intracellularis*, LYO dilution: 31.6 ml bacterin in 68.4 ml growth medium (1:3.2)

SC-54 dilution: 50 ml bacterin in 250 ml PBS (1:6)

The final vaccines were formulated with equal volumes of the three components

A. Efficacy of the *L. intracellularis* Component

The objectives of the study were to demonstrate the efficacy of the lyophilized and frozen forms of the *Lawsonia intracellularis* antigen in young pigs when given in combination with *Erysipelothrix rhusiopathiae* antigen and *Salmonella cholerasuis* antigen and lack of interference by the *Erysipelothrix rhusiopathiae* antigen and *Salmonella cholerasuis* antigen on the efficacy of the *Lawsonia intracellularis* antigen.

Experimental Design:

The study consisted of 4 treatment groups of weaned 3 week old (+/−5 days) *L. intracellularis*-negative test pigs. All vaccinations were given on day 0 of the study. Treatment group 1 (n=20) will receive a target dose of $1\times10^{4.9}$ TCID$_{50}$/dose of ENTERISOL® Ileitis (FF) in combination with INGELVAC® ERY-ALC ($9\times10^9$ cfu/dose) and ENTERISOL® SC-54 (FF) ($4\times10^8$ cfu/dose) via oral drench. Treatment group 2 (n=20) will receive a target dose of $1\times10^{4.9}$ TCID$_{50}$/dose of ENTERISOL® Ileitis lyophilized in combination with INGELVAC® ERY-ALC ($9\times10^9$ cfu/dose) and ENTERISOL® SC-54 (FF) ($4\times10^8$ cfu/dose) via oral drench. Treatment group 3 (n=20) are designated as study "challenge controls" and did not receive a vaccination but were given an equivalent volume of placebo via oral drench.

Treatment group 4 (n=10) are designated as study "Strict Controls" and did not receive a vaccine or placebo treatment or challenge.

On day 23 of the study, treatment groups 1, 2 and 3 (20 pigs each) received a target dose of greater than $1\times10^{7.0}$ TCID$_{50}$ of heterologous virulent low passage pure culture challenge material (*L. intracellularis*) by gavage. Three weeks after challenge administration (day 43), all treatment groups (1 through 4) were euthanized and necropsied for gross and microscopic analysis for lesions from PPE.

Results:

Gross Lesions

At necropsy, a section of the intestinal tract approximately 1 meter long containing segments of the ileum, cecum and colon was removed from each pig and examined for gross lesions. The lesions were scored by severity and the ilealcecal junction was removed for immunohistochemistry (IHC) staining. Table 1, below shows the average lesion scores for treatment group by lesion site and the number of animals with a positive score per group. Treatment group 4, strict controls are included in this table because 2 of the 10 animals did have mild lesion scores characterized by redness and slight swelling in the colon.

TABLE 1

Average gross lesion scores by treatment group and number of animals with a positive score within groups.

| Group ID | Treatment | Ileum score | Cecum score | Colon score | Overall group score | # '+'/ group total |
|---|---|---|---|---|---|---|
| 1 | FF-combo | 0.2 | 0 | 0.1 | 0.3$^a$ | 5/20$^a$ |
| 2 | Lyo-combo | 0.3 | 0 | 0 | 0.3$^a$ | 4/20$^a$ |
| 3 | Controls | 1.2 | 0.4 | 0.3 | 1.9$^b$ | 13/18$^b$ |
| 4 | Strict controls | 0 | 0 | 0.2 | 0.2 | 2/10 |

$^{a,b}$Scores with different letters denote statistically significant differences (p ≤ 0.05). Strict controls were not part of the statistical analysis.

Statistical analyses were run on individual site scores, overall scores and positive animals per treatment group. There was a statistically significant difference between vaccinates in treatment groups 1 and 2 versus the controls for gross lesion scores overall and by treatment group (p<0.0001). There was also a significant difference between vaccinates versus controls in number of positive animals (p<0.0001). There was no significant difference between treatment groups 1 and 2.

Microscopic Lesions

Table 2, below, shows the microscopic lesion data by treatment group. Note that treatment group 4 had no samples positive for *L. intracellularis*.

TABLE 2

Average IHC scores for microscopic lesions by treatment group.

| Group ID | Treatment | Small intestine sites | Small intestine lesions | Small intestine IHC positive | Large intestine sites | Large intestine lesions | Large intestine IHC positive | # '+'/ group total |
|---|---|---|---|---|---|---|---|---|
| 1 | FF-combo | 0.4 | 0.3 | 0.35 | 0.1 | 0.05 | 0.05 | 5/20 |
| 2 | Lyo-combo | 0.45 | 0.40 | 0.30 | 0.25 | 0.15 | 0.15 | 6/20 |
| 3 | Controls | 0.56 | 0.39 | 0.39 | 0.22 | 0.22 | 0.28 | 6/18 |
| 4 | Strict controls | 0 | 0 | 0 | 0 | 0 | 0 | 0/10 |

The control group did show higher microscopic lesion scores with more positive animals than either vaccinate group but the differences noted were not statistically significant (p>0.05).

Conclusion

The results of this study demonstrate that the combination of INGELVAC® ERY-ALC, ENTERISOL® SC-54 with ENERISOL® Ileitis, ALC does not cause interference with the Lawsonia fraction of the vaccine. Both the frozen and lyophilized forms of the vaccine significantly reduced intestinal lesions caused by Lawsonia intracellularis in this vaccination/challenge study. No interference by the *Erysipelothrix* and *Salmonella* vaccines on the efficacy of the Lawsonia vaccine was observed in this study.

B. Efficacy of the *Erysipelothrix rhusiopathiae* Component

The objectives of the study were to demonstrate the efficacy of the lyophilized and frozen forms of the *Erysipelothrix rhusiopathiae* antigen in young pigs when given in combination with *Lawsonia intracellularis* antigen and *Salmonella cholerasuis* antigen and lack of interference by the *Lawsonia intracellularis* antigen and *Salmonella cholerasuis* antigen on the efficacy of the *Erysipelothrix rhusiopathiae* antigen.

Experimental Design:

This study consisted of four groups with 15 animals in each of groups 1, 2, and 3, and five animals in group 4. Group 1 was vaccinated with the INGELVAC® Ery-ALC ($9 \times 10^9$ cfu/dose), ENTERISOL® SC-54 $6.9 \times 10^8$ cfu/dose) and ENTERISOL® Ileitis $1 \times 10^{6.1}$ TCID$_{50}$/dose), combination via oral drench on day 0. Group 2 was vaccinated with INGELVAC® Ery-ALC ($9 \times 10^9$ cfu/dose) only via oral drench on day 0. Groups 3 and 4 served as challenge controls and strict controls, respectively.

Pigs in groups 1, 2, and 3 were challenged with virulent *E. rhusiopathiae*, strain E-1-6 on day 21 by intramuscular injection in the ham muscle ($4 \times 10^4$ cfu/dose.). Animals were observed daily for clinical signs, lesions, or elevated temperatures associated with Erysipelas. All animals were euthanized seven days post challenge. Pigs that displayed clinical signs and/or elevated temperatures were necropsied. Kidney and spleen samples were collected in an attempt to determine if the cause of the clinical lesions and/or elevated temperatures was due to an Erysipelas infection.

Results:

Clinical Observations:

Daily clinical observations were made from Trial Day 19 (−2 DPC) through Trial Day 28 (7 DPC). There were no clinical symptoms seen in the group given the Combination vaccine. Only one of fifteen (6.7%) animals that received INGELVAC® Ery-ALC only became lethargic and had a lesion that was red and raised. In contrast, all of the challenge control animals were affected by the challenge, with symptoms including rapid respiration, lethargy, red and raised lesions, and lameness. There was also a 33% mortality rate in the challenge control group with death occurring in 5 of 15 animals.

TABLE 3

Clinical Signs

| Treatment Group | # of animals affected | Bacterial Isolation (% Positive) | Mortality |
| --- | --- | --- | --- |
| Ery/SC-54/Ileitis | 0/15 (0%) | N/A | 0/15 (0%) |
| INGELVAC ® Ery-ALC | 1/15 (6.7%) | 1/1 (100%) | 0/15 (0%) |
| Challenge Controls | 15/15 (100%) | 13/15 (86.7%) | 5/15 (33.3%) |
| Strict Controls | 0/5 (0%) | N/A | 0/5 (0%) |

Post Challenge Organ Culture:

At study termination, the animals were euthanized, and those affected with clinical signs of erysipelas were necropsied, and the kidney and spleen were cultured for the presence of *Erysipelothrix*. *E. rhusiopathiae* was recovered from 13 of 15 of the animals in the challenge control group, and from the one animal in the INGELVAC® Ery-ALC group.

TABLE 4

Results of the post challlange organ culture

| Parameters | SC-54/Ery Ileitis | INGELVAC ® Ery-ALC | Challenge Controls | Strict Controls |
| --- | --- | --- | --- | --- |
| Clin Score (% affected) | 0 | 6.7 | 100 | 0 |
| % Mortality | 0 | 0 | 33.3 | 0 |
| Bacterial Isolation (% Pos) | N/A | 6.7 | 86.7 | N/A |
| Avg. Temps (F.) | 103.7 | 103.5 | 104.7 | 103.2 |

Conclusion:

The combination of INGELVAC® Ery-ALC, ENTERISOL® SC-54, and ENTERISOL® Ileitis, ALC proved to be efficacious against an *E. rhusiopathiae* challenge and, therefore proves that there is no interference from the ENTERISOL SC-54 and ENTERISOL Ileitis vaccines.

C. Efficacy of the *Salmonella cholerasuis* Component

The objectives of the study were to demonstrate the efficacy of the lyophilized and frozen forms of the *Salmonella cholerasuis* antigen in young pigs when given in combination with *Lawsonia intracellularis* antigen and *Erysipelothrix rhusiopathiae* antigen and lack of interference by the *Lawsonia intracellularis* antigen and *Erysipelothrix rhusiopathiae* antigen on the efficacy of the *Salmonella cholerasuis* antigen.

Experimental Design:

This study consisted of four groups with 15 animals in groups 1, 2, and 3, and five animals in group 4. Pigs in group 1 were vaccinated with the INGELVAC® Ery-ALC ($3.3 \times 10^{10}$ logs/dose), ENTERISOL® SC-54 ($2.8 \times 10^8$ logs/dose) and ENTERISOL® Ileitis (6.1 logs/dose) combination via oral drench on day 0. Pigs in group 2 were vaccinated with ENTERISOL® SC-54 only via oral drench on day 0. Pigs in groups 3 and 4 did not receive vaccine treatment and served as challenge and strict controls, respectively.

Pigs in groups 1, 2, and 3 were challenged with virulent *Salmonella cholerasuis*, Strain 38, intranasally on day 28 ($2.93 \times 10^9$ cfu/dose). Fecal swabs were collected daily following challenge and cultured for *Salmonella* sp. Animals were weighed at the time of vaccination, challenge, and necropsy. Body temperatures were monitored for two days prior to challenge and daily following challenge. The clinical health of each animal was monitored daily for the duration of the study. At the termination of the study (day 41), pigs were euthanized and organs (tonsil, lung, liver, spleen, mesenteric lymph node (MLN), ileum, and colon) were collected and cultured for the presence of *Salmonella* sp.

Results:

INGELVAC® Ery-ALC and ENTERISOL® Ileitis vaccines were used according to label recommended dosage, and the ENTERISOL® SC-54 vaccine was diluted to the minimum immunizing dose, $2.8 \times 10^8$ cfu/mL, prior to administration. General observations were made from vaccination to challenge. Clinically, both vaccinated groups (combination and ENTERISOL® SC-54 only) performed well against the virulent *Salmonella cholerasuis* challenge, with significant ($P<0.05$) reductions in rectal temperatures, clinical symptoms, and increased weight gains in comparison to the challenge controls. There were notable differences between vaccinated and challenge control groups in the culture results.

Both vaccinated groups had reduced amounts of fecal shedding (8.1%-combo, 11.4%-SC-54) as compared to the challenge controls (24%), with significant (P<0.05) reductions of the number of animals shedding the bacteria in the last 5 days of the 13-day observation period. *Salmonella cholerasuis* was recovered from all tissues in the ENTERISOL® SC-54 vaccinate and challenge control groups, but only from four of the seven tissues in each vaccinate of the combination vaccinate group. In addition, there was a significant (P<0.05) reduction in the recovery of bacteria from the MLN and colon from pigs in both vaccinated groups compared to the challenge control group.

TABLE 5

Results Summary Table

| Parameters | Salm/Ery Lawsonia | Salmonella Only | Challenge Controls | Strict Controls |
|---|---|---|---|---|
| Mean Clinical Scores | 10.26 | 10.34 | 10.28 | 10.02 |
| # days significantly (P < 0.05) different from Challenge Controls (post-Controls) | 3 days (31, 39, & 40) | 2 days (39 and 40) | N/A | 2 days (31 and 39) |
| Mean Rectal Temps (° F.) | 103.7 | 103.9 | 104.5 | 103.2 |
| # days significantly (P < 0.05) different from Challenge Controls (post-challenge) | 10 days (31-41) | 8 days (32-39) | N/A | 10 days (29-38) |
| Average Daily Weight Gain (lbs/day post-challenge) | 0.84$^{a,b}$ | 1.00$^a$ | 0.60$^b$ | 1.54$^c$ |
| Fecal Culture (% Pos) | 8.1 | 11.4 | 24 | 1.7 |
| Tissue Culture (% Pos) | 9.5 | 17.1 | 35.7 | 0 |

$^{a,b}$= Like letters are not statistically (P < 0.05) different.

Conclusion:

The combination of INGELVAC® Ery-ALC, ENTERISOL® SC-54, and ENTERISOL® Ileitis proved to be efficacious against a virulent *Salmonella cholerasuis* challenge. Therefore, this study demonstrates that there is no interference of the Ery-ALC and Ileitis-ALC vaccines to the SC-54 vaccine.

What is claimed:

1. A method for the treatment or reduction in the incidence or severity of clinical signs caused by *Lawsonia intracellularis, Salmonella choleraesuis*, and *Erysipelothrix rhusiopathiae*, said method comprising the steps of:
administering a composition containing antigenic components, wherein the antigenic components consist essentially of attenuated modified live *Lawsonia intracellularis*, an immunological active component of *Salmonella choleraesuis*, and an immunological active component of *Erysipelothrix rhusiopathiae*, to a non-human animal in need thereof, wherein said administration results in the treatment or reduction of clinical signs of *Lawsonia intracellularis, Salmonella choleraesuis*, and *Erysipelothrix rhusiopathiae*.

2. The method of claim 1, wherein said attenuated modified live *Lawsonia intracellularis*, said immunological active component of *Salmonella choleraesuis*, and said immunological active component of *Erysipelothrix rhusiopathiae* are administered on the same day.

3. The method of claim 1, wherein said attenuated modified live *Lawsonia intracellularis*, said immunological active component of *Salmonella choleraesuis*, and said immunological active component of *Erysipelothrix rhusiopathiae* are administered at the same time.

4. The method of claim 1, wherein at least two of said attenuated modified live *Lawsonia intracellularis*, said immunological active component of *Salmonella choleraesuis*, and said immunological active component of *Erysipelothrix rhusiopathiae* are combined together prior to administration thereof.

5. The method of claim 1, wherein said clinical signs include lesions caused by *Lawsonia intracellularis*, lesions caused by *Erysipelothrix rhusiopathiae*, and clinical signs caused by virulent *Salmonella cholaraesuis*.

6. The method of claim 1, wherein said attenuated modified live *Lawsonia intracellularis* is effective for reducing the incidence of or lessening the severity of porcine proliferative enteropathy caused by *Lawsonia intracellularis*.

7. The method of claim 1, wherein said immunological active component of Salmonella choleraesuis further comprises attenuated *Salmonella choleraesuis* and wherein said attenuated *Salmonella choleraesuis* is effective for reducing the incidence of or lessening the severity of infections caused by *Salmonella choleraesuis*.

8. The method of claim 1, wherein said immunological active component of *Erysipelothrix rhusiopathiae* further comprises attenuated *Erysipelothrix rhusiopathiae* and wherein said attenuated *Erysipelothrix rhusiopathiae* is effective for reducing the incidence of or lessening the severity of infections caused by *Erysipelothrix rhusiopathiae*.

9. The method of claim 1, wherein said composition further comprises a veterinary-acceptable carrier.

10. The method of claim 9, wherein said veterinary-acceptable carrier is selected from the group consisting of solvents, dispersion media, coatings, adjuvants, stabilizing agents, diluents, preservatives, antibacterial and antifungal agents, isotonic agents, adsorption delaying agents, and combinations thereof.

11. A method for treating or reducing the incidence or severity of clinical signs of diseases caused by *Lawsonia intracellularis* and two or more further swine pathogenic microorganisms, said two or more further swine pathogenic microorganisms including *Salmonella choleraesuis* and *Erysipelothrix rhusiopathiae*, said method comprising the steps of:
administering a composition containing antigenic components, where the antigenic components consist essentially of avirulent modified live *Lawsonia intracellularis* to a non-human animal in need thereof together with an immunological active component of *Salmonella choleraesuis* and an immunological active component of *Erysipelothrix rhusiopathiae*, to an animal in need thereof, wherein said administration results in the treatment or reduction in the incidence or severity of clinical signs of *Lawsonia intracellularis, Salmonella choleraesuis*, and *Erysipelothrix rhusiopathiae*.

12. The method of claim 11, wherein said administration of said avirulent modified live *Lawsonia intracellularis*, said immunological active component of *Salmonella choleraesuis* and said immunological active component of *Erysipelothrix rhusiopathiae* occurs on the same day.

13. The method of claim 11, wherein said administration of said avirulent modified live *Lawsonia intracellularis*, said immunological active component of *Salmonella choleraesuis* and said immunological active component of *Erysipelothrix rhusiopathiae* occurs at the same time.

14. The method of claim 11, wherein at least two of said avirulent modified live *Lawsonia intracellularis*, said immunological active component of *Salmonella choleraesuis* and said immunological active component of *Erysipelothrix rhusiopathiae* are combined together prior to said administration.

15. The method of claim 11, wherein said clinical signs include lesions caused by *Lawsonia intracellularis*, lesions caused by *Erysipelothrix rhusiopathiae*, and clinical signs caused by virulent *Salmonella cholaraesuis*.

16. The method of claim 11, wherein said avirulent modified live *Lawsonia intracellularis* is effective for reducing the incidence of or lessening the severity of porcine proliferative enteropathy caused by *L. intracellularis*.

17. The method of claim 11, wherein said immunological active component of *Salmonella choleraesuis* further comprises attenuated *Salmonella choleraesuis* and wherein said attenuated *Salmonella choleraesuis* is effective for reducing the incidence of or lessening the severity of infections caused by *Salmonella choleraesuis*.

18. The method of claim 11, wherein said immunological active component of *Erysipelothrix rhusiopathiae* further comprises attenuated *Erysipelothrix rhusiopathiae* and wherein said attenuated *Erysipelothrix rhusiopathiae* is effective for reducing the incidence of or lessening the severity of infections caused by *Erysipelothrix rhusiopathiae*.

19. The method of claim 11, wherein said composition further comprises a veterinary-acceptable carrier.

20. The method of claim 1, wherein said veterinary-acceptable carrier is selected from the group consisting of solvents, dispersion media, coatings, adjuvants, stabilizing agents, diluents, preservatives, antibacterial and antifungal agents, isotonic agents, adsorption delaying agents, and combinations thereof.

21. A method for the treatment or reduction in the incidence or severity of clinical signs caused by *Lawsonia intracellularis, Salmonella choleraesuis*, and *Erysipelothrix rhusiopathiae*, said method consisting essentially of the steps of:

administering a composition containing antigenic components, wherein the antigenic components consist essentially of attenuated modified live *Lawsonia intracellularis*, an immunological active component of *Salmonella choleraesuis*, and an immunological active component of *Erysipelothrix rhusiopathiae* to a non-human animal in need thereof, wherein said administration results in the treatment or reduction of clinical signs of *Lawsonia intracellularis, Salmonella choleraesuis*, and *Erysipelothrix rhusiopathiae*.

* * * * *